United States Patent
Sciascia

(10) Patent No.: US 10,238,646 B2
(45) Date of Patent: *Mar. 26, 2019

(54) METHODS FOR TREATING PRURITUS

(71) Applicant: TREVI THERAPEUTICS, INC., New Haven, CT (US)

(72) Inventor: Thomas Sciascia, Belmont, MA (US)

(73) Assignee: Trevi Therapeutics Inc., New Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/984,249

(22) Filed: Dec. 30, 2015

(65) Prior Publication Data

US 2016/0346273 A1   Dec. 1, 2016

Related U.S. Application Data

(63) Continuation of application No. 14/106,677, filed on Dec. 13, 2013, now abandoned, and a continuation-in-part of application No. 13/715,625, filed on Dec. 14, 2012, now Pat. No. 8,637,538.

(60) Provisional application No. 61/737,488, filed on Dec. 14, 2012.

(51) Int. Cl.
| A61K 9/00 | (2006.01) |
| A61K 9/20 | (2006.01) |
| A61K 45/06 | (2006.01) |
| A61K 31/485 | (2006.01) |

(52) U.S. Cl.
CPC .......... *A61K 31/485* (2013.01); *A61K 9/0053* (2013.01); *A61K 9/205* (2013.01); *A61K 9/2009* (2013.01); *A61K 9/2013* (2013.01); *A61K 9/2054* (2013.01); *A61K 45/06* (2013.01)

(58) Field of Classification Search
CPC .................................................... A61K 31/198
USPC ....................................................... 514/279
See application file for complete search history.

(56) References Cited

U.S. PATENT DOCUMENTS

| 4,443,442 | A | 4/1984 | Skillern |
| 4,720,384 | A | 1/1988 | Di Lucco et al. |
| 5,760,023 | A | 6/1998 | Farrar et al. |
| 6,156,769 | A | 12/2000 | Farrar et al. |
| 6,174,891 | B1 | 1/2001 | Nagase et al. |
| 6,316,461 | B1 | 11/2001 | Nagase et al. |
| 6,451,806 | B2 | 9/2002 | Farrar |
| 6,787,149 | B1 | 9/2004 | El Khoury et al. |
| 6,984,493 | B1 | 1/2006 | Kumagai et al. |
| 7,056,500 | B2 | 6/2006 | Bentley et al. |
| 7,563,899 | B2 | 7/2009 | Boyd et al. |
| 7,884,102 | B2 | 2/2011 | Dolle et al. |
| 8,105,590 | B2 | 1/2012 | Yao et al. |
| 8,309,596 | B2 | 11/2012 | Flohr et al. |
| 8,394,812 | B2 | 3/2013 | Baichwal et al. |
| 8,476,318 | B2 | 7/2013 | Schmaus et al. |
| 8,637,538 | B1 | 1/2014 | Sciascia |
| 8,940,753 | B1 | 1/2015 | Sciascia |
| 8,987,289 | B2 | 3/2015 | Sciascia |
| 2001/0006967 | A1 | 7/2001 | Crain et al. |
| 2001/0047005 | A1 | 11/2001 | Farrar |
| 2002/0013296 | A1 | 1/2002 | Zhang et al. |
| 2003/0054030 | A1 | 3/2003 | Gordon |
| 2003/0191147 | A1 | 10/2003 | Sherman et al. |
| 2004/0157913 | A1 | 8/2004 | Jacob et al. |
| 2004/0171631 | A1 | 9/2004 | Hu et al. |
| 2004/0266806 | A1 | 12/2004 | Sanghvi et al. |
| 2005/0182258 | A1 | 8/2005 | Schmidhammer et al. |
| 2006/0063792 | A1 | 3/2006 | Dolle et al. |
| 2006/0194826 | A1 | 8/2006 | Oshlack et al. |
| 2007/0048376 | A1 | 3/2007 | Baichwal et al. |
| 2007/0060501 | A1 | 3/2007 | Jhamandas et al. |
| 2007/0099946 | A1 | 5/2007 | Doshan et al. |
| 2008/0176884 | A1 | 7/2008 | Perez et al. |
| 2008/0207669 | A1 | 8/2008 | Perez et al. |
| 2008/0234306 | A1 | 9/2008 | Perez et al. |
| 2008/0242720 | A1 | 10/2008 | Mangel et al. |
| 2008/0275074 | A1 | 11/2008 | Izumimoto et al. |
| 2009/0030026 | A1 | 1/2009 | Baichwal et al. |
| 2009/0093509 | A1 | 4/2009 | Nazir et al. |
| 2009/0131466 | A1 | 5/2009 | Liang et al. |
| 2009/0209569 | A1 | 8/2009 | Arnelle et al. |
| 2009/0247635 | A1 | 10/2009 | Ehrenpreis |
| 2009/0312359 | A1 | 12/2009 | Foss et al. |
| 2010/0150854 | A1 | 6/2010 | Schmaus et al. |
| 2010/0227876 | A1 | 9/2010 | Rech |
| 2010/0261746 | A1 | 10/2010 | Sanghvi et al. |
| 2011/0190331 | A1 | 8/2011 | Avey et al. |
| 2012/0040009 | A1 | 2/2012 | Hermann |
| 2012/0077803 | A1 | 3/2012 | Stuetz et al. |
| 2014/0171459 | A1 | 6/2014 | Sciascia |
| 2014/0179727 | A1 | 6/2014 | Sciascia |
| 2014/0350042 | A1 | 11/2014 | Sciascia |
| 2015/0197545 | A1 | 7/2015 | Schteingart et al. |
| 2015/0359789 | A1 | 12/2015 | Sciascia |

(Continued)

FOREIGN PATENT DOCUMENTS

| JP | 2001-163784 | 6/2001 |
| JP | 2008-109898 | 5/2008 |

(Continued)

OTHER PUBLICATIONS

International Search Report and Written Opinion in International Application No. PCT/US2013/075096, dated Apr. 14, 2014, 8 pages.

(Continued)

*Primary Examiner* — Layla Soroush

(74) *Attorney, Agent, or Firm* — Cooley LLP

(57) ABSTRACT

The present invention relates to methods for treating pruritus with anti-pruritic compositions.

23 Claims, 1 Drawing Sheet

(56) References Cited

U.S. PATENT DOCUMENTS

| | | |
|---|---|---|
| 2017/0000782 A1 | 1/2017 | Sciascia |
| 2017/0216277 A1 | 8/2017 | Sciascia |

FOREIGN PATENT DOCUMENTS

| | | |
|---|---|---|
| WO | WO 84/00889 A1 | 3/1984 |
| WO | WO 02/087582 A1 | 11/2002 |
| WO | WO 2004/091623 A1 | 10/2004 |
| WO | WO-2005/117871 | 12/2005 |
| WO | WO 2007/025005 A2 | 3/2007 |
| WO | WO 2008/024490 A2 | 2/2008 |
| WO | WO 2008/129000 A1 | 10/2008 |
| WO | WO 2009/047562 A1 | 4/2009 |
| WO | WO 2009/070733 A1 | 6/2009 |
| WO | WO 2009/132313 A2 | 10/2009 |
| WO | WO 2010/107457 A1 | 9/2010 |
| WO | WO 2011/117306 A1 | 9/2011 |
| WO | WO 2012/022919 A2 | 2/2012 |
| WO | WO 2012/052169 A2 | 4/2012 |
| WO | WO 2014/093871 A1 | 6/2014 |
| WO | WO 2015/192071 A1 | 12/2015 |

OTHER PUBLICATIONS

Bernstein, J. et al., "Butorphanol-induced pruritis antagonized by naloxone," J Am Acad Dermatol, 5(2):227-228 (1981).
Bigliardi et al., "Peripheral Opiate Receptor System in Human Epidermis and Itch," Itch Basic Mechanism and Therapy, 10:97-106 (2004).
Bruni, E. et al., "Phototherapy of generalized prurigo nodularis," Journal compilation, British Association of Dermatologists, Clinical and Experimental Dermatology, 35, 549-550 (2009).
Butelman et al., "Kappa-Opioid Receptor Binding Populations in Rhesus Monkey Brain: Relationship to an Assay of Thermal Antinociception," J. Pharmacol. Exp. Ther., 285(2):595-601 (1998).
Carstens et al., "Animal Models of Itch: Scratching Away at the Problem," Itch: Basic Mechanisms and Therapy, Yosipovitch et al., Eds., Marcel Dekker Inc, New York, pp. 35-50 (2004).
Cohen et al., "Nalbuphine is better than naloxone for treatment of side effects after epidural morphine," Anesth Analg., 75(5):747-52 (1992).
Davies et al., "A Blinded Study Using Nalbuphine for Prevention of Pruritus Induced by Epidural Fentanyl," Anesthesiology, 69(5): 763-765 (1998).
Dawn et al., "Butorphanol for treatment of intractable pruritus," J Am Acad Dermatol., 54(3):527-531 (2006).
Dworkin et al., "Phamacologic management of neuropathic pain: Evidence-based recommendations," International Assoc for the Study of Pain, pp. 237-251 (2007).
European Medecines Agency (2010) "Public summary of opinion on orphan designation (−)-17-(cyclopropylmethyl)-3,14 β-dihydroxy-4,5 α-epoxy-6β-[N-methyl-trans-3-(3-furyl) acrylamido] morphinan hydrochloride (intravenous use) for the treatment of uremic pruritus," http://www.ema.europa.eu/docs/en_GB/document_library/Orphan_designation/2009/10/WC500005585.pdf.
Filho, J. W. et al., "Prurigo Nodularis of Hyde—An Update," Journal of the European Academy of Dermatology and Venereology, 14(2):75-82 (2000).
Fujii et al., "Essential structure of opioid κ receptor agonist nalfurafine for binding to the κ receptor 3: Synthesis of decahydro(iminoethano)phenanthrene derivatives with an oxygen functionality at the 3-position and their pharmacologies," Bioorg. Med. Chem. Lett., 22:7711-7714 (2012).
Gerak et al., "Antinociceptive and Respiratory Effects of Nalpuphine in Rhesus Monkeys," J. Pharmacol. Exp. Ther., 271(2):993-999 (1994).
Gharagozlou et al., "Activity of opioid ligands in cells expressing cloned μ opioid receptors," BMC Pharmacol. 3:1 (2003).
Gharagozlou et al., "Pharmacological profiles of opioid ligands at Kappa opioid receptors," BMC Pharmacol., 6:3 (2006).

Gutstein et al., "Chapter 23: Opioid Analgesics" in: Goodman & Gilman's The Pharmacologic Basis of Therapeutics. 10th Ed., Hardman et al., Eds., McGraw Hill, pp. 569-619 (2001).
Jung, S., II et al., "Efficacy of Naltrexone in the Treatment of Chronic Refractory Itching in Burn Patients: Preliminary Report of an Open Trial," J. of Burn Care & Research, 30(2):257-260 (2009).
Kanavy, H. et al., "Treatment of Refractory Prurigo Nodularis With Lenalidomide," The Cutting Edge: Challenges in Medical and Surgical Therapies, Archives of Dermatology, 148(7):794-796 (2012).
Keithi-Reddy et al., "Uremic Pruritus," Kidney International, 72:373-377 (2007).
Kendrick et al., "Naloxone versus nalbuphine infusion for prophylaxis of epidural morphine-induced pruritus," Anesth. Analg., 82(3):641-7 (1996).
Kfoury et al., "Uremic pruritus," J. Nephrol., 25(5):644-652 (2011).
Kjellberg et al, "Pharmacological control of opiod-induced pruritus: a quantitative systematic review of randomized trials," European J. of Anaesthesiology, pp. 346-357, (2001).
Kumagai et al., "Prospects for a novel kappa-opioid receptor agonist, TRK-820 in uremic pruritus," in: Itch, Basic Mechanisms and Therapy, Yosipovitch et al., Eds., Marcel Dekker Inc, New York, pp. 279-286 (2004).
Lawnhorn et al., "Epidural Morphine With Butorphanol for Postoperative Analgesia After Cesarean Delivery," Anesth. Analg., 72:53-57 (1991).
Lee et al., "Effects of Butorphanol on Morphine-induced Itch and Analgesia in Primates," Anesthesiology, 107(3):478-485 (2007).
Lee, M. R. et al., "Prurigo nodularis: A review," Australasian J. of Dermatology, 46:211-220 (2005).
Malgorzata et al., "Understanding Pruritus in Systemic Disease," Journal of Pain and Symptom Management, 21(2):151-168 (2001).
Metze, D. et al., "Efficacy and safety of naltrexone, an oral opiate receptor antagonist, in the treatment of pruritus in internal and dermatological diseases," J .Am Acad Dermatol, 41(4):533-539 (1999).
Montgomery, Clinical Trial: "Nalbuphine for the Treatment of Opioid Induced Pruritus in Children," [Online], http://clinicaltrials.gov/show/NCT00323154 (Dec. 20, 2013), 3 pages.
Nagase et al., "Essential structure of opioid κ receptor agonist nalfurafine for binding to the κ receptor 2: Synthesis of decahydro(iminoethano)phenanthrene derivatives and their pharmacologies," Bioorg. Med. Chem. Lett., 22:5071-5074 (2012).
Naini et al., G., "A Promising Drug for the Treatment of Uremic Pruritus," Saudi J. Kidney Dis. Transpl., 18:378-381(2007).
Pan, "μ-Opposing actions of the k-opioid receptor," Trends in Pharmacological Sciences, 19:94-98 (1998).
Patel et al., "An update on pruritus associated with CKD," Am J Kidney Dis., 50:11-20 (2007).
Pauli-Magnus et al., "Naltrexone Does Not Relieve Uremic Pruritus: Results of a Randomized, Double-Blind, Placebo-Controlled Crossover Study," J. Am. Soc. Nephrol., 11:514-519 (2000).
Peer et al, "Randomised crossover trial of naltrexone in uraemic pruritus," The Lancet, 348(9041):1552-1554 (1996).
Peng et al., "Pharmacological Properties of Bivalent Ligands Containing Butorphan Linked to Nalbuphine, Naltrexone and Naloxone at μ, δ and κ Opiod Receptors," J. Med. Chem., 50(9):2254-2258 (2007).
Penning et al., "Reversal of epidural morphine-induced respiratory depression and pruritus with nalbuphine," Canadian Journal of Anesthesia, 35(6): 599-604 (1988).
Phan et al., "Antipruritic treatment with systemic μ-opioid receptor antagonists: A review," Journal of the American Academy of Dermatology, 63(4):680-688 (2010).
Phan et al., "Systemic Kappa Opioid Receptor Agonists in the Treatment of Chronic Pruritus: A Literature Review," Acta Dermato-Venereologica, 92: 555-560 (2012).
Rose et al, "Gabapentin: pharmacology and it use in pain management," Anaesthesia, pp. 451-462 (2002).
Schmelz, "Itch-mediators and mechanisms," J. of Dermatological Science, 28:91-96 (2002).
Schmidt et. al., "Nalbuphine," Drugs and Alcohol Dependence, 14:339-362 (1985).

(56) References Cited

OTHER PUBLICATIONS

Schwacha, M. G., "Opiates and the Development of Post-Injury Complications: a Review," Int. J. Clin. Exp. Med., 1:42-49 (2008).
Spring, P. et al., "Prurigo nodularis: retrospective study of 13 cases managed with methotrexate," Clinical and Experimental Dermatology, 39:468-473 (2014).
Stander, S. et al. "Treatment of Pruritus in Internal and Dermatological Diseases with Opiod Receptor Antagonists," Itch, Basic Mechanisms and Therapy, Michael Dekker, Inc., New York, pp. 259-277 (2004).
Stander, S. et al., "Targeting the Neurokinin Receptor 1 with Aprepitant: A Novel Antipruritic Strategy," 5(6):1-5 (2010) www.plosone.org.
Steinhoff, M. et al. "Modern Aspects of Cutaneous Neurogenic Inflammation," downloaded from http://archderm.jamanetwork.com on Oct. 28, 2013, 10 pages.
Umechi et al., "Involvement of central mu-opioid system in the scratching behavior in mice, and the suppression of it by the activation of kappa-opioid system," Eur. J. Pharmacol., 477(1):29-35 (2003).
Wang et al., "Comparison of intravenous nalbuphine infusion versus saline as an adjuvant for epidural morphine," Reg. Anesth., 21(3):214-8 (1996).
Wang et al., "Comparison of Pharmacological Activities of Three Distinct κ Ligands (Salvinorin A, TRK-820 and 3FLB) on κ Opioid Receptors in Vitro and Their Antipruritic and Antinociceptive Activities in Vivo," J. Pharmacol. Exp. Ther., 312(1):220-230 (2005).
Wittels et al., "Opioid Antagonist Adjuncts to Epidural Morphine for Postcesarean Analgesia: Maternal Outcomes," Anesth. Analg., 77:925-32 (1993).
Yokoyama et al. "Treatment of epidural morphine induced pruritus with butorphanol," English Abstract, Masui, 8(2):178-82 (2009).
Yosipovitch, "Chronic Pruritus: a Paraneoplastic Sign," Dermatol. Ther., 23(6):590-596 (2010).
Yosipovitch, G. t al., "Chronic Pruritus," N. Eng. J. Med., 368(17):1625-1634 (2013).
Supplementary European Search Report for European Application No. 13863494.4, dated Apr. 12, 2016, 7 pages.
Liao, C-C et al., "Efficacy of intramuscular nalbuphine versus diphenhydramine for the prevention of epidural morphine-induced pruritus after cesarean delivery," Chang Gung Medical Journal, 34:172-178 (Mar. 2011).
Somrat, C. et al., "Optimal dose of nalbuphine for treatment of intrathecal-morphine induced pruritus after Caesarean Section," J. Obstet. Gynaecol. Res., 25(3):209-213 (Jan. 1999).
International Preliminary Report on Patentability in International Application No. PCT/US2013/075096, dated Jun. 16, 2015, 6 pages.
International Search Report and Written Opinion in International Application No. PCT/US2015/035650, dated Sep. 4, 2015, 9 pages.
International Preliminary Report on Patentability for International Application No. PCT/US2015/035650, dated Dec. 15, 2016, 6 pages.
International Search Report and Written Opinion in International Application No. PCT/US2017/012530, dated Mar. 20, 2017, 19 pages.
International Search Report and Written Opinion in International Application No. PCT/US2017/023398, dated May 25, 2017, 12 pages.
Bakker, et al., "Bullous pemphigoid as pruritus in the elderly a common presentation." JAMA Dermatology, Aug. 2013 vol. 149, No. 8, pp. 950-953 (abstract), 2 pages.
Gharagozlou, P. et al., "Activation profiles of opioid ligands in HEK cells expressing delta opioid receptors," BMC Neurosci., 2002, 3:19.
U.S. Appl. No. 14/738,550, filed Jun. 12, 2015 (pending).
U.S. Appl. No. 15/016,831, filed Feb. 5, 2016 (pending).
U.S. Appl. No. 15/400,486, filed Jan. 6, 2017 (pending).
U.S. Appl. No. 15/465,158, filed Mar. 21, 2017 (pending).
U.S. Appl. No. 15/635,932, filed Jun. 28, 2017 (pending).
U.S. Appl. No. 14/106,677, filed Dec. 13, 2013 (abandoned).
U.S. Appl. No. 14/139,697, filed Dec. 23, 2013 (abandoned).

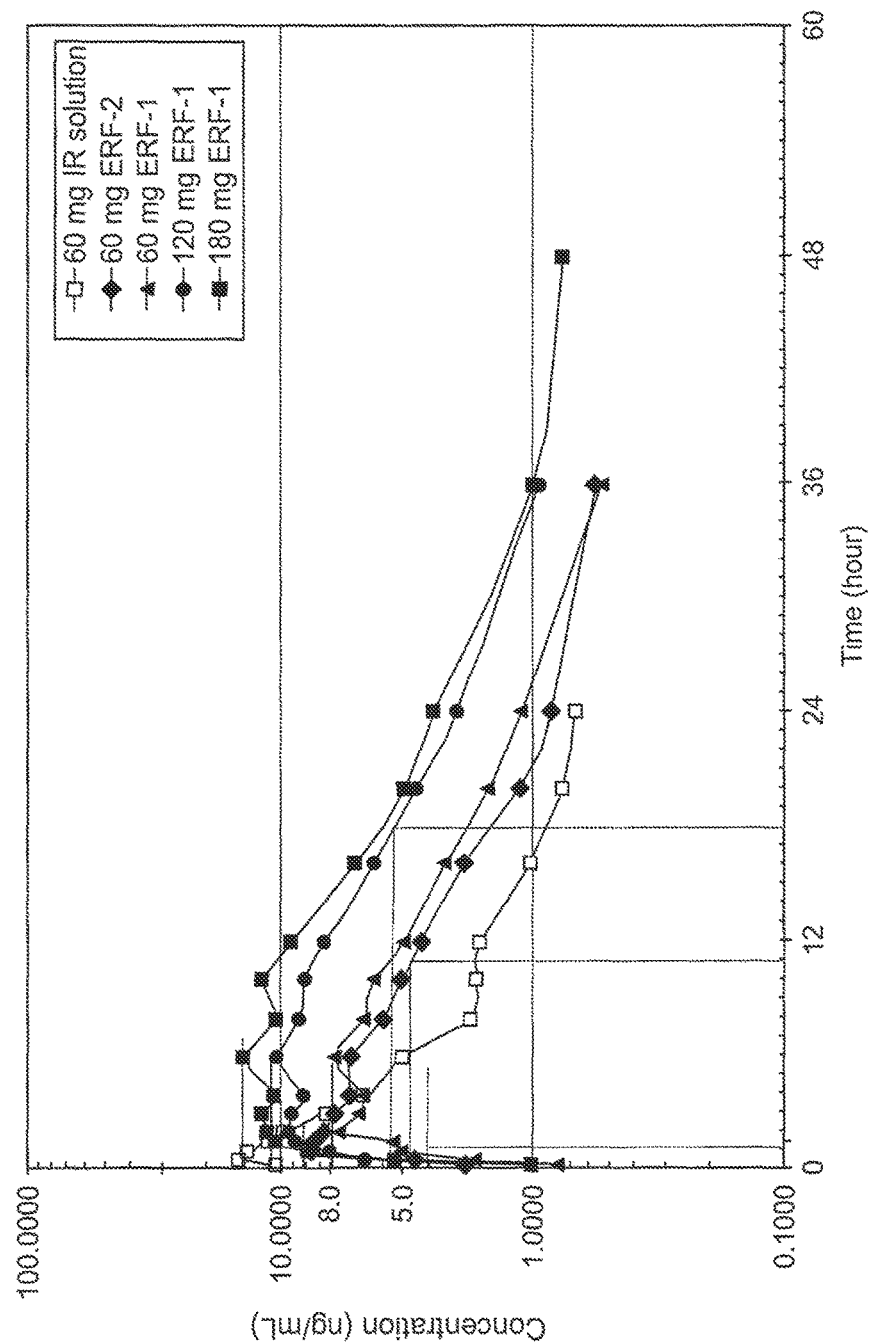

METHODS FOR TREATING PRURITUS

RELATED APPLICATIONS

This application is a continuation of U.S. application Ser. No. 14/106,677, filed on Dec. 13, 2013, which claims priority to U.S. Provisional Application Ser. No. 61/737,488, filed Dec. 14, 2012 and U.S. application Ser. No. 13/715,625, filed Dec. 14, 2012, all of which are herein incorporated by reference in their entireties.

FIELD OF THE INVENTION

The present invention relates to methods for treating pruritus with anti-pruritic compositions.

BACKGROUND

Pruritus, or itch, is a sensation that stimulates the desire or reflex to scratch, which can be either generalized or localized. The cause of pruritus is not fully understood. Proposed contributors to the pathogenesis of pruritus may include anemia or other manifestation of erythropoietin deficiency, histamine release from skin mast cells, skin dryness, secondary hyperparathyroidism, hyperphosphatemia with increased calcium phosphate deposition in the skin and alterations in the endogenous opioidergic system with overexpression of opioid μ-receptors.

SUMMARY OF THE INVENTION

The present invention provides methods for treating various pruritic conditions using nalbuphine or a pharmaceutically acceptable salt or ester thereof. In one embodiment, the present invention provides methods of treating pruritus comprising administering an effective amount of an anti-pruritus agent to a subject in need of such treatment, wherein the anti-pruritus agent is nalbuphine or a pharmaceutically acceptable salt or ester thereof.

In one embodiment, the subject is suffering from a pruritic condition, and said pruritic condition comprises atopic dermatitis, nervous dermatitis, contact dermatitis, seborrheic dermatitis, autosensitization dermatitis, caterpillar dermatitis, asteatosis, senile pruritus cutaneous, insect sting, photosensitive dermatosis, urticaria, prurigo, herpes, impetigo, eczema, tinea, lichen, psoriasis, scabies and acne vulgaris, or visceral diseases complicated with pruritus.

In another embodiment, the subject is suffering from a skin change comprising pruritus secondary to inflamed skin, pruritus arising from conditions of non-diseased skin, pruritus associated with chronic secondary scratch, or skin lesions resulting from an underlying medical condition.

In yet another embodiment, the subject has uremic pruritus or prurigo nodularis.

In some embodiments, the anti-pruritus agent is administered at an initial oral dose of from about 15 mg to about 30 mg once or twice a day and then titrated to an effective dose.

In some other embodiments, the anti-pruritus agent is administered at an initial dose of from about 15 mg to about 30 mg twice a day or once a day for about 2-3 days and then titrated to an effective dose at about 15 mg to about 30 mg increment.

In yet some other embodiments, the maximum dose of the anti-pruritus agent is about 480 mg when said agent is administered to a subject twice a day or about 240 mg when said agent is administered to a subject once a day.

In some embodiments, the anti-pruritus agent is administered with an AM dosage and a PM dosage and wherein the PM dosage is higher than the AM dosage, or vice versa.

In some other embodiments, the anti-pruritus agent is administered at a dose of about 60 mg or about 120 mg twice a day to a subject with uremic pruritus or renal impairment or about 90 mg or about 180 mg twice a day to a subject without a renal impairment condition.

In some embodiments, the anti-pruritus agent is in an extended release oral dosage form and the administration provides in the subject a mean $C_{max}$ of from about 1 ng/mL to about 90 ng/mL, from about 5 ng/mL to about 85 ng/mL, from about 5 ng/ml to about 45 ng/ml, from about 25 ng/mL to about 72 ng/mL, or from about 13 ng/mL to about 28 ng/mL.

In some other embodiments, the anti-pruritus agent is in an extended release oral dosage form and the administration provides in the subject an $AUC_{(0-\infty)}$ of from about 40 ng·hr/mL to about 3000 ng·hr/mL, 40 ng·hr/mL to about 800 ng·hr/mL or 30 ng·hr/mL to about 360 ng·hr/mL.

In some embodiments, the anti-pruritus agent is in an extended release oral dosage form.

In some other embodiments, the administration provides in the subject a pK release profile with the characteristics of a) a mean $C_{max}$ from about 1.5 ng/mL to about 195 ng/mL, and b) $AUC_{(0-\infty)}$ from about 20 ng·hr/mL to about 4100 ng·hr/mL.

In yet some other embodiments, the administration provides in the subject a pK release profile with the characteristics of a) a mean $C_{max}$ from about 1.5 ng/mL to about 60 ng/mL, and b) $AUC_{(0-\infty)}$ from about 20 ng·hr/mL to about 700 ng·hr/mL.

The present methods, and advantages thereof, are further illustrated by the following non-limiting detailed description and Examples.

BRIEF DESCRIPTION OF THE DRAWINGS

FIG. 1 is a graphical representation of the log of the mean nalbuphine plasma concentration versus time for several nalbuphine compositions.

DETAILED DESCRIPTION

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The terms "administer," "administering" or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term "subject" includes, without limitation, a human or an animal. Exemplary animals include, but are not limited to, mammals such as mouse, rat, guinea pig, dog, cat, horse, cow, pig, monkey, chimpanzee, baboon, or rhesus monkey.

The term "treating" as used herein with regard to a subject, refers to improving at least one symptom of the subject's disorder. Treating can be curing, improving, or at least partially ameliorating a disorder.

Nalbuphine

Nalbuphine HCl (17-(cyclobutylmethyl)-4,5α-epoxymorphinian-3, 6α, 14-triol, hydrochloride) is currently available only as a generic medication in an injectable form. An injectable form of nalbuphine has been available as an approved drug formulation since 1978. Nubain® was the innovator brand injectable form of nalbuphine on which the presently sold generic bioequivalent injectable formulations are based. The injectable formulation is currently approved for use in the relief of moderate to severe pain, a supplement to balanced anesthesia, for pre-operative and post-operative analgesia and obstetrical analgesia during labor and delivery.

Opioid Receptors

There are three classical types of opioid receptors that have been investigated as the mediators of opiate effects. These opioid receptors are classified as mu ("μ"), kappa ("κ") and delta ("δ"). Nalbuphine is a derivative of 14-hydroxymorphine and is structurally related to the opioid μ-receptor agonist oxymorphone and the opioid μ-receptor antagonist naloxone. Gutstein et al. (Chapter 23: Opioid Analgesics, *Goodman & Gilman's The Pharmacologic Basis of Therapeutics,* 10th Ed., McGraw Hill 2001, pp 569-619) report that nalbuphine exerts its clinical pharmacologic action by competitively antagonizing the opioid μ-receptor and simultaneously acting as an agonist at the opioid κ-receptor, and thus is a member of the "opioid agonist-antagonist" class of drugs that mechanistically work through this dual pharmacologic process. Subsequent in vitro work by Gharagozlou et al. (*Neurosci.* 2002 3:19) showed that nalbuphine is in addition a δ opioid receptor antagonist. Gutstein et al. (supra) state that the stimulus for the development opioid agonist-antagonist drugs was to identify a drug with analgesic properties with less respiratory depression and addiction potential.

Nalbuphine in the Treatment of Pruritus

In a first aspect, the present invention provides a method of treating pruritus comprising administering an effective amount of an anti-pruritus agent to a subject in need of such treatment, wherein the anti-pruritus agent is nalbuphine or a pharmaceutically acceptable salt or ester thereof.

"Nalbuphine" includes nalbuphine free base, metabolites thereof, derivatives thereof, solvates thereof (e.g., hydrates, alcoholates, etc.) and/or pharmaceutically acceptable salts or esters thereof. Metabolites of nalbuphine include, for example the glucuronide conjugate metabolite and metabolites resulting from methylation, oxidation/dehydrogenation, hydroxylation, double hydroxylation, triple hydroxylation, oxidative methylation, glucoside conjugation, glucuronide conjugation, and hydroxyl-glucuronide conjugation of nalbuphine. Exemplary metabolites can include nornalbuphine, 6-ketonalbuphine, nalbuphine 3-glucuronide. In one embodiment, metabolites include triple hydroxylated nalbuphine, mono-hydroxylated nalbuphine, and mono-glucuronidated nalbuphine. Isomers include the C-6β-epimer of nalbuphine (Mallinckrodt, Nalbuphine hydrochloride Technical Package August 2003). Derivatives of nalbuphine can include pharmaceutically acceptable ester prodrugs thereof (including alkoxy esters such as methoxy and ethoxy esters) which can be hydrolyzed in vivo to provide nalbuphine, as well as ether or other compounds prepared by, e.g. reacting the hydroxyl groups of nalbuphine with suitable protecting agents.

In one embodiment, nalbuphine suitable for use in the present methods is in the form of any pharmaceutically acceptable salt or ester known in the art. Exemplary pharmaceutically acceptable salts include without limitation hydrochloric, sulfuric, nitric, phosphoric, hydrobromic, maleic, malic, ascorbic, citric, tartaric, pamoic, lauric, stearic, palmitic, oleic, myristic, lauryl sulfuric, napthalinesulfonic, linoleic, linolenic acid, and the like. In one embodiment the anti-pruritus agent is the hydrochloride salt of nalbuphine.

The present invention also includes pharmaceutically acceptable esters of the anti-pruritic agent. The term "ester" denotes a derivative of the anti-pruritic agent containing an ester functional group (as described herein), which is capable of releasing the anti-pruritic agent when the ester form is administered to a subject. Release of the active ingredient occurs in vivo. Pharmaceutically acceptable esters can be prepared by techniques known to one skilled in the art. These techniques generally modify appropriate functional groups in a given compound. These modified functional groups however regenerate original functional groups by metabolism of the compound in vivo. Esters include compounds wherein a hydroxy, amino, carboxylic, or a similar group is modified.

Suitable pharmaceutically acceptable esters for a hydroxyl group include inorganic esters such as phosphate esters and α-acyloxyalkyl ethers and related compounds which, as a result of in vivo hydrolysis of the ester, provide the parent hydroxy group. In vivo hydrolyzable ester forming groups for hydroxy include alkanoyl (e.g., $C_{1-10}$ linear, branched or cyclic alkyl), benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxy acetyl.

Nalbuphine as employed in the present methods can form a part of a pharmaceutical composition by combining nalbuphine, or a pharmaceutically acceptable salt or ester thereof, with a pharmaceutically acceptable carrier. Additionally, the compositions can include an additive selected from the group consisting of adjuvants, excipients, diluents, release-modifying agents and stabilizers. The composition can be an immediate release formulation, a delayed release formulation, a sustained release formulation or an extended release formulation.

Pruritic Conditions

According to the present invention, pruritus includes any itchy or pruritic condition, e.g., a sensation that causes the desire or reflex to scratch. In some embodiments, methods of the present invention are used for the treatment of a subject suffering from a pruritic condition selected from the group consisting of atopic dermatitis, nervous dermatitis, contact dermatitis, seborrheic dermatitis, autosensitization dermatitis, caterpillar dermatitis, asteatosis, senile pruritus cutaneous, insect sting, photosensitive dermatosis, urticarial, prurigo, herpes, impetigo, eczema, tinea, lichen, psoriasis, scabies and acne vulgaris, visceral diseases complicated with pruritus such as malignant tumors, diabetes mellitus, hepatic diseases, renal failure, hemodialysis, peritoneal dialysis, and pregnancy.

In some embodiments, methods of the present invention are used for the treatment of a subject suffering from a pruritic condition associated with a skin change. For example, such pruritic condition can be selected from the group consisting of pruritus secondary to inflamed skin (e.g., atopic dermatitis, psoriasis, burns) pruritus arising from conditions of non-diseased skin (e.g., uremic pruritus, cholestatic pruritus, cancers, hydroxyethyl starch induced pruritus), and pruritus associated with chronic secondary scratch or other types of skin lesions that may or may not be the result of an underlying medical condition (e.g., prurigo nodularis) and the underlying disease is categorized based on histological, radiological or other investigations as being of an origin selected from the group consisting of dermatologic origin, systemic disease origin, neurologic origin, psychogenic origin, mixed origin, or other origin.

In some embodiments, methods of the present invention are used for the treatment of a subject suffering from a pruritic condition associated with neurogenic inflammation of the skin, e.g., prurigo nodularis, atopic dermatitis, burn pruritus, burn, wound healing, etc. In some other embodiments, methods of the present invention are used for the treatment of a subject suffering from a pruritic condition associated with neurogenic inflammation with elevated substance P level. In still some other embodiments, methods of the present invention are used for the treatment of a subject suffering from a pruritic condition associated with elevated substance P level.

In some embodiments, methods of the present invention are used for the treatment of a subject suffering from a pruritic condition associated with one or more related or unrelated conditions. For example, the pruritic condition can be associated with a dermatologic condition including aquagenic pruritus, atopic dermatitis, idiopathic pruritus, Lichen simplex chronicus, prurigo nodularis, psoriasis, and scabies. In another example, the pruritic condition can be associated with a hematological or oncological condition including cancer related pruritus, chemotherapy induced pruritus, HIV protease inhibitor induced pruritus, Hodgkin's lymphoma associated pruritus, polycythemia vera, etc. In another example, the pruritic condition can be associated with a metabolic condition including cholestatic pruritus, uremic pruritus, etc. In still another example, the pruritic condition can be associated with a condition of pain or neurological condition including brachioradial pruritus, burn induced pruritus, neuropathic pruritus, morphine induced pruritus, multiple sclerosis associated pruritus, post herpetic pruritus, pruritus associated with psychiatric causes, etc.

In one embodiment, methods of the present invention are used for the treatment of uremic pruritus. In another embodiment, methods of the present invention are used for the treatment of prurigo nodularis. In yet another embodiment, methods of the present invention are used to treat human beings. In still another embodiment, methods of the present invention are used to treat animals other than human beings.

Formulations

The methods of the present invention can employ various formulations for administration to subjects, e.g., humans and animals in unit dosage forms, such as tablets, capsules, pills, powders, granules, sterile parenteral solutions or suspensions, and oral solutions or suspensions, and oil-water emulsions containing suitable quantities of an anti-pruritic agent, e.g., nalbuphine, or pharmaceutically acceptable salts or esters thereof.

Oral pharmaceutical dosage forms can be either solid or liquid. The solid dosage forms can be tablets, capsules, granules, and bulk powders. Types of oral tablets include compressed, chewable lozenges and tablets which can be enteric-coated, sugar-coated or film-coated. Capsules can be hard or soft gelatin capsules, while granules and powders can be provided in non-effervescent or effervescent form with the combination of other ingredients known to those skilled in the art. In other embodiments, the oral dosage form may be an osmotic-controlled release oral delivery system (OROS). In other embodiments, the oral dosage form may include matrix-embedded dosage forms or related devices. In some embodiments, the present oral dosage forms may include orally-disintegrating tablets.

Pharmaceutically acceptable carriers utilized in tablets include binders, lubricants, diluents, disintegrating agents, coloring agents, flavoring agents, and wetting agents.

Liquid oral dosage forms include aqueous solutions, emulsions, suspensions, solutions and/or suspensions reconstituted from non-effervescent granules and effervescent preparations reconstituted from effervescent granules.

Aqueous solutions include, for example, elixirs and syrups. Emulsions can be either oil-in water or water-in-oil. Elixirs are clear, sweetened, hydroalcoholic preparations. Pharmaceutically acceptable carriers used in elixirs include solvents. Syrups can be concentrated aqueous solutions of a sugar, for example, sucrose, and can contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions can use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, can include organic acids and a source of carbon dioxide. Coloring and flavoring agents can be used in all of the above dosage forms.

Parenteral administration of the formulations of the present invention includes intravenous, subcutaneous and intramuscular administrations. of immediate, sustained (e.g., depot), extended, and/or modified release formulations (e.g., as described herein). Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

The concentration of the pharmaceutically active compound can be adjusted so that an injection provides an effective amount to produce the desired pharmacological effect. The exact dose depends on the age, weight and condition of the patient or animal, as is known in the art. The unit-dose parenteral preparations are packaged in an ampoule or a syringe with a needle. All preparations for parenteral administration must be sterile, as is known and practiced in the art. Illustratively, intravenous or intraarterial infusion of a sterile aqueous solution containing an anti-pruritic agent is an effective mode of administration.

Pharmaceutical dosage forms for rectal administration can be rectal suppositories, capsules and tablets for systemic effect. Rectal suppositories as used herein mean solid bodies for insertion into the rectum which melt or soften at body temperature releasing the pharmacologically and/or therapeutically active ingredients contained in the composition of this invention. Pharmaceutically acceptable substances utilized in rectal suppositories are bases or vehicles and agents to raise the melting point. Examples of bases include cocoa butter (theobroma oil), glycerin-gelatin, carbowax, polyoxyethylene glycol and mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

The compositions can be suspended in micronized or other suitable form or can be derivatized to produce a more soluble active product. The form of the resulting composition depends upon a number of factors, including the intended mode of administration and the solubility of the anti-pruritic agent in the selected carrier or vehicle. The effective concentration is sufficient for treating or alleviating pruritus, and can be empirically determined. The concentration is generally greater than the concentration for systemic administration of the compound.

The resulting mixture can be a solution, suspension, emulsion or the like, and can be formulated as a cream, gel, ointment, emulsion, solution, elixir, lotion, suspension, tincture, paste, foam, aerosol, irrigation, spray, suppository, bandage, or any other formulation suitable for topical or local administration. Modes of administration can include topical application to the skin, scalp, eyes, and/or nasal, buccal or sublingual mucosa.

Pharmaceutical and cosmetic carriers or vehicles suitable for administration of the compositions include any such carriers known to those skilled in the art to be suitable for the particular mode of administration. The anti-pruritic agent can be included in the carriers in amounts sufficient to exert a therapeutically useful effect without serious toxic effects on the treated individual.

To formulate these compositions, a weight fraction of an anti-pruritic agent is dissolved, suspended, dispersed or otherwise mixed in a selected vehicle at an effective concentration such that the pruritic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream (USP), and hydrophilic ointment (USP).

The compositions employed in the present methods can relieve pruritus when applied to the skin. The composition can be administered topically to the affected area up to eight times per day, as needed, to provide reduction in and relief from itching. Relief can be temporary or permanent, and can even be evident after a single dose of the composition. When the composition is administered in a form other than a topical preparation, it should be administered in an amount sufficient to provide relief from pruritus that is within safety guidelines established by the FDA. Determining the appropriate amount to administer to a patient is within the skill of the person of ordinary skill in the art in association with teachings provided by the present invention.

Solutions of the compositions of this invention intended for topical administration contain an amount of the composition effective to deliver an anti-pruritic amount, typically at a concentration of between about 0.01% w/w to about 5% w/w. The balance of the solution is water, a suitable organic solvent or other suitable solvent or buffer. These compositions that are formulated as solutions or suspensions can be applied to the skin, or can be formulated as an aerosol or foam and applied to the skin as a spray-on. The aerosol compositions typically contain from 25% to 80% w/w, preferably from 30% to 50% w/w, of a suitable propellant. Gel compositions can be formulated by simply admixing a suitable thickening agent to the solution or suspension.

Solutions and suspensions can also be topically applied to the eyes and mucosa. Solutions, particularly those intended for ophthalmic use, can be formulated as 0.01%-10% w/w isotonic solutions, pH about 5-7, with appropriate salts, and preferably containing one or more of the compositions herein at a concentration of about 0.1% w/w, up to about 5% w/w or more. Suitable ophthalmic solutions are known in the art.

Compositions of solid forms intended for topical application can be formulated as stick-type compositions intended for application to the lips or other parts of the body. Such compositions contain an effective amount of an anti-pruritic agent, e.g. nalbuphine or a pharmaceutically acceptable salt or ester thereof. The amount of the anti-pruritic agent present is typically from about 0.01% w/w to about 5% w/w. The solids also contain from about 40% to 98% w/w, preferably from about 50% to 90% w/w, of emollients. This composition can further contain from 1% to 20% w/w, preferably from 5% to 15% w/w, of a suitable thickening agent, and, if desired or needed, emulsifiers and water or buffers.

In addition, the compositions, and preparations containing the compositions, can also be coated on bandages, mixed with bioadhesives, or included in dressings. Thus, combinations of bandages, bioadhesives, dressings and other such materials and the compositions formulated as described herein are provided.

Sustained Release Formulations

Nalbuphine formulations which can be employed in the present methods include oral sustained release nalbuphine formulations as described in U.S. Provisional Pat. Appl. Nos. 60/772,466 and 60/710,772; and U.S. patent application Ser. Nos. 11/509,347 and 12/154,496 (published as U.S. Patent Publications 2007/0048376 and 2009/0030026, respectively), each of which is incorporated herein by reference in their entireties.

In some embodiments, the present methods can employ oral sustained release formulations of nalbuphine including an anti-pruritic effective amount of nalbuphine or a pharmaceutically acceptable salt or ester thereof. The oral sustained release formulations can provide a controlled release of the drug over a longer period than observed for bolus injections or immediate release oral formulations (e.g., at least about 8-12 hours). Reducing the frequency of dosing provides the potential for enhanced patient convenience and compliance with the present methods. The lower dosing frequency also has the potential to provide reduced side effects because the patient may be exposed to lower peak concentrations of drug over time.

The present methods can employ compositions including nalbuphine or a pharmaceutically acceptable salt or ester thereof and a sustained release delivery system. The sustained release delivery system includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent. Alternatively, in other embodiments, the present methods can employ compositions including nalbuphine or a pharmaceutically acceptable salt or ester thereof and a sustained release delivery system, which may employ a hydrophobic compound in a sustained release system.

The nalbuphine can be homogeneously dispersed in the sustained release delivery system. In some embodiments, the nalbuphine or pharmaceutically acceptable salt or ester thereof is present in the composition in an amount of about 1 mg to about 240 mg; about 1 mg to about 150 mg; about 1 mg to about 125 mg; or about 1 mg to about 100 mg. In some embodiments, the nalbuphine or pharmaceutically acceptable salt or ester thereof is present in the composition in an amount of about 5 mg to about 80 mg; about 10 mg to about 70 mg; about 15 mg to about 60 mg; about 40 mg to about 80 mg; about 50 mg to about 70 mg; or about 45 mg to about 60 mg. In one embodiment, the nalbuphine or pharmaceutically acceptable salt or ester thereof is present in the composition in an amount of about 15 mg, about 20 mg, about 25 mg, about 30 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, or about 240 mg. In another embodiment, the nalbuphine or pharmaceutically acceptable salt thereof is present in the composition in an amount of about 30 mg, about 45 mg, about 60 mg, about 120 mg, or about 180 mg. In yet another embodiment, the nalbuphine or pharmaceutically acceptable salt thereof is present in the composition in an amount of about 15 mg, 30 mg, 90 mg, 120 mg or 180 mg.

In yet another embodiment, the nalbuphine or pharmaceutically acceptable salt thereof, e.g., HCL is present in the composition in an amount of about 15 mg, about 30 mg, about 90 mg, about 120 mg, or about 180 mg.

In some embodiments, the sustained release delivery system is present in the composition in an amount from about 10 mg to about 420 mg; from about 25 mg to about 225 mg; from about 21 mg to about 198 mg; or from about 80 mg to about 200 mg; from about 80 mg to about 220 mg; from about 90 mg to about 210 mg; from about 100 mg to about 200 mg; from about 110 mg to about 190 mg; from about 120 mg to about 180 mg; from about 130 mg to about 170 mg; from about 140 mg to about 160 mg; from about 30 mg to about 60 mg; from about 60 mg to about 180 mg; from about 30 mg to about 180 mg, from about 75 mg to about 150 mg, from about 80 mg to about 160 mg, from about 90 mg to about 150 mg, from about 100 mg to about 140 mg, from about 110 mg to about 130 mg, from about 100 mg to about 300 mg, from about 200 mg to about 300 mg or from about 200 mg to about 250 mg. In one embodiment, the sustained release delivery system is present in the composition in an amount from about 75 mg to about 150 mg.

In some embodiments, the sustained release delivery system is present in the composition in an amount of about 30 mg, about 60 mg, about 75 mg, about 80 mg, about 90 mg, about 100 mg, about 110 mg, about 112 mg, about 115 mg, about 117 mg, about 120 mg, about 125 mg, about 130 mg, about 135 mg, about 140 mg, about 145 mg, about 150 mg, about 160 mg, about 170 mg, about 180 mg, about 190 mg, about 200 mg, about 210 mg, about 220 mg, about 225 mg, about 230 mg, about 240 mg, about 250 mg, about 260 mg, about 270 mg, about 280 mg, about 300 mg, about 320 mg, about 340 mg, about 360 mg, about 380 mg, about 400 mg or about 420 mg. In another embodiment, the sustained release delivery system is present in the composition in an amount of about 112 mg.

The ratio of nalbuphine or pharmaceutically acceptable salt or ester thereof in the compositions to the sustained release delivery system is generally from about 4:1 to about 1:25. In some embodiments, the ratio of nalbuphine or pharmaceutically acceptable salt or ester thereof to the sustained release delivery system is generally from about 2.5:1 to about 1:4. In some embodiments, the ratio of nalbuphine or pharmaceutically acceptable salt or ester thereof to the sustained release delivery system is generally from about 5:1 to about 1:5, about 4:1 to about 1:4, about 3:1 to about 1:3, about 2:1 to about 1:2, about 1:1 to about 1:5, about 1:1 to about 1:4, about 1:1 to about 1:3, about 1:1 to about 1.2, and about 1:2 to about 1:3. In some embodiments, the ratio of nalbuphine or pharmaceutically acceptable salt or ester thereof to the sustained release delivery system is about 1:1, about 1:2, about 1:2.5, about 1:3, about 1:4, or about 1:5.

In one embodiment, at least one hydrophilic compound is present in the sustained release delivery system in an amount of about 5% to about 80% by weight; the at least one cross-linking agent is present in the sustained release delivery system in an amount of about 0.5% to about 80% by weight; and the at least one pharmaceutical diluent is present in the sustained release delivery system in an amount of about 20% to about 80% by weight. In another embodiment, the at least one hydrophilic compound is present in the sustained release delivery system in an amount of about 8% to about 31% by weight; the at least one cross-linking agent is present in the sustained release delivery system in an amount of about 12% to about 47% by weight; and the at least one pharmaceutical diluent is present in the sustained release delivery system in an amount of about 20% to about 78% by weight. In another embodiment, the at least one hydrophilic compound is present in the sustained release delivery system in an amount of about 10% to about 20% by weight; the at least one cross-linking agent is present in the sustained release delivery system in an amount of about 15% to about 25% by weight; and the at least one pharmaceutical diluent is present in the sustained release delivery system in an amount of about 50% to about 85% by weight. In some embodiments, the at least one hydrophilic compound is present in the sustained release delivery system in an amount of about 8%, about 9%, about 10%, about 11%, about 12%, about 13%, about 14%, about 15%, about 16%, about 17%, about 18%, about 19%, about 20%, about 22%, about 24%, about 26%, about 28%, about 30%, about 32%, about 34%, or about 36% by weight; the at least one cross-linking agent is present in the sustained release delivery system in an amount of about 10%, about 11%, about 12%, about 13%, about 14%, about 15%, about 16%, about 17%, about 18%, about 19%, about 20%, about 22%, about 24%, about 26%, about 28%, about 30%, about 32%, about 33%, about 34%, or about 35% by weight; and the at least one pharmaceutical diluent is present in the sustained release delivery system in an amount of about 40%, about 45%, about 50%, about 55%, about 60%, about 65%, about 70%, about 80%, or about 85% by weight.

In some embodiments, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cross-linking agent is present in the sustained release delivery system in an amount of about 15%, about 16%, about 17%, about 18%, about 19%, about 20%, or about 22% by weight; and the at least one pharmaceutical diluent is present in the sustained release delivery system in an amount of about 55%, about 60%, about 65%, about 70%, about 80%, or about 85% by weight. In one embodiment, the at least one hydrophilic compound is present in the sustained release delivery system in an amount of about 8%, about 12%, or about 20% by weight; the at least one cross-linking agent is present in the sustained release delivery system in an amount of about 12%, about 18%, or about 30% by weight; and the at least one pharmaceutical diluent is present in the sustained release delivery system in an amount of about 40%, about 60%, or about 70% by weight.

In one embodiment, nalbuphine is in the form of any pharmaceutically acceptable salt known in the art. Exemplary pharmaceutically acceptable salts include without limitation hydrochloric, sulfuric, nitric, phosphoric, hydrobromic, maleric, malic, ascorbic, citric, tartaric, pamoic, lauric, stearic, palmitic, oleic, myristic, lauryl sulfuric, napthalinesulfonic, linoleic, linolenic acid, and the like. One embodiment includes the hydrochloride salt of nalbuphine.

The sustained release delivery system includes at least one hydrophilic compound. The hydrophilic compound preferably forms a gel matrix that releases the nalbuphine or the pharmaceutically acceptable salt or ester thereof at a sustained rate upon exposure to liquids. The rate of release of the nalbuphine or the pharmaceutically acceptable salt or ester thereof from the gel matrix depends on the drug's partition coefficient between the components of the gel matrix and the aqueous phase within the gastrointestinal tract. The weight ratio of nalbuphine to hydrophilic compound is generally in the range of about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, and about 2:1 to about 1:2. In some embodiments, the weight ratio of nalbuphine to hydrophilic compound is in the range of about 10:1 to about 1:1, about 10:1 to about 2:1, about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, and about 2:1 to about 1:1. In some embodiments, the weight ratio of nalbuphine to hydrophilic compound is in the range of about 6:1 to about 1:1, about 5:1 to about 2:1, about 4:1 to about 3:1, about 4:1 to about 2:1, and about 5:1 to about 2:1. In some embodiments, the weight ratio of nalbuphine to hydrophilic compound is about 1:5, about 1:4.5, about 1:4.4, about 1:4, about 1:3.5, about 1:3.3, about 1:3, about 1:2.5, about 1:2, about 1:1, and about 1:1.5.

The sustained release delivery system generally includes the hydrophilic compound in an amount of about 5% to about 80% by weight. In some embodiments, the sustained release delivery system generally includes the hydrophilic compound in an amount of about 5% to about 30%, about 8% to about 31%, about 10% to about 20%, about 20% to about 60%, or about 40% to about 60% by weight. In one embodiment, the sustained release delivery system includes the hydrophilic compound in an amount of about 8% to about 31% by weight. In one embodiment, the sustained release delivery system includes the hydrophilic compound in an amount of about 10% to about 20% by weight. In some embodiments, the sustained release delivery system includes the hydrophilic compound in an amount of about 10%, about 11%, about 12%, about 13%, about 14%, about 15%, about 16%, about 17%, about 18%, about 19%, or about 20% by weight. In one embodiment, the sustained release delivery system includes the hydrophilic compound in an amount of about 12% by weight. In one embodiment, the sustained release delivery system includes the hydrophilic compound in an amount of about 8% by weight. In one embodiment, the sustained release delivery system includes the hydrophilic compound in an amount of about 20% by weight. In one embodiment, the sustained release delivery system includes the hydrophilic compound in an amount of about 28% by weight.

The hydrophilic compound is any compound known in the art to be hydrophilic. Exemplary hydrophilic compounds include without limitation gums, cellulose ethers, polyvinyl pyrrolidone, protein-derived compounds, and mixtures thereof. Exemplary gums include without limitation heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include without limitation hydroxyalkyl celluloses and carboxyalkyl celluloses. In some embodiments, cellulose ethers include hydroxyethyl celluloses, hydroxypropyl celluloses, hydroxypropylmethyl-celluloses, carboxy methylcelluloses, and mixtures thereof. In some embodiments, the hydrophilic compound is a gum. In other embodiments, the hydrophilic compound is a heteropolysaccharide gum. In further embodiments, the hydrophilic compound is a xanthan gum or derivative thereof. Derivatives of xanthan gum include without limitation, for example, deacylated xanthan gum, the carboxymethyl esters of xanthan gum, and the propylene glycol esters of xanthan gum.

In another aspect, the sustained release delivery system further includes at least one cross-linking agent. In one embodiment, the cross-linking agent is a compound that is capable of cross-linking the hydrophilic compound to form a gel matrix in the presence of liquids. As used herein, "liquids" includes, for example, gastrointestinal fluids and aqueous solutions, such as those used for in vitro dissolution testing. The sustained release delivery system generally includes the cross-linking agent in an amount of about 0.5% to about 80% by weight. In one embodiment, the sustained release delivery system generally includes the cross-linking agent in an amount of about 12% to about 47% by weight. In another embodiment, the sustained release delivery system generally includes the cross-linking agent in an amount of about 20% to about 30% by weight. In one embodiment, the sustained release delivery system generally includes the cross-linking agent in an amount of about 15% to about 25% by weight. In some embodiments, the at least one cross-linking agent is present in the sustained release delivery system in an amount of about 15%, about 16%, about 17%, about 18%, about 19%, about 20%, about 21%, about 22%, about 23%, about 24%, or about 25% by weight. In one embodiment, the sustained release delivery system includes the cross-linking agent in an amount of about 18% by weight. In one embodiment, the sustained release delivery system includes the cross-linking agent in an amount of about 12% by weight. In one embodiment, the sustained release delivery system includes the cross-linking agent in an amount of about 30% by weight. In one embodiment, the sustained release delivery system includes the cross-linking agent in an amount of about 42% by weight.

Exemplary cross-linking agents include homopolysaccharides. Exemplary homopolysaccharides include without limitation galactomannan gums, such as guar gum, hydroxypropyl guar gum, and locust bean gum. In some embodiments, the cross-linking agent is a locust bean gum or a guar gum. In other embodiments, the cross-linking agent is an alginic acid derivative or hydrocolloid.

In some embodiments, when the sustained release delivery system includes at least one hydrophilic compound and at least one cross-linking agent, the weight ratio of hydrophilic compound to cross-linking agent is from about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, or about 1:2 to about 2:1. In some embodiments, the weight ratio of hydrophilic compound to cross-linking agent is about 1:5, about 1:4.5, about 1:4, about 1:3.5, about 1:3, about 1:2.5, about 1:2, about 1:1.5, and about 1:1.

When the sustained release delivery system includes at least one hydrophilic compound and at least one cross-linking agent, the weight ratio of the nalbuphine or pharmaceutically acceptable salt or ester thereof to the sum of the at least one hydrophilic compound and the at least one cross-linking agent is from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, or from about 2:1 to about 1:2. In some embodiments, the weight ratio of the nalbuphine or pharmaceutically acceptable salt or ester thereof to the sum of the at least one hydrophilic compound and the at least one cross-linking agent is from about 4:1 to about 1:1, from about 4:1 to about 1:1.5, from about 3:1 to about 1:1, or from about 2:1 to about 1:1. In one embodiment, the ratio of the nalbuphine or pharmaceutically acceptable salt or ester thereof to the sum of the at least one hydrophilic compound and the at least one cross-linking agent is about 5:1, about 4:1 (i.e., 1:0.25), about 3.5:1, about 3:1, about 2.5:1, about 2:1 (i.e., 1:0.5), about 1.9:1, about 1.8:1, about 1.7:1, about 1.6:1, about 1.5:1, about 1.4:1, about 1.3:1, about 1.2:1, about 1.1:1, about 1:1, about 1:1.5, about 1:2, about 1:3, about 1:4, and about 1:5.

The sustained release delivery system further includes one or more pharmaceutical diluents known in the art. Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Nonlimiting examples of water-soluble pharmaceutical diluents include lactose, dextrose, sucrose, or mixtures thereof. The weight ratio of pharmaceutical diluent to hydrophilic compound is generally from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In some embodiments, the weight ratio of pharmaceutical diluent to hydrophilic compound is generally from about 9:1 to about 1:1.5. In some embodiments, the weight ratio of pharmaceutical diluent to hydrophilic compound is about 9:1, about 8.75:1, about 8.5:1, about 8.25:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, or about 1:1.

The sustained release delivery system generally includes one or more pharmaceutical diluents in an amount of about 20% to about 80%, about 30% to about 70%, about 40% to about 70%, or about 40% to about 60%. In one embodiment, the sustained release delivery system includes one or more pharmaceutical diluents in an amount of about 20% to about 70% by weight. In one embodiment, the sustained release delivery system includes one or more pharmaceutical diluents in an amount of about 50% to about 85% by weight. In some embodiments, the sustained release delivery system includes one or more pharmaceutical diluents in an amount of about 55%, about 60%, about 65%, about 70%, about 80%, or about 85% by weight. In one embodiment, the sustained release delivery system includes one or more pharmaceutical diluents in an amount of about 20% by weight. In one embodiment, the sustained release delivery system includes one or more pharmaceutical diluents in an amount of about 30% by weight. In one embodiment, the sustained release delivery system includes one or more pharmaceutical diluents in an amount of about 40% by weight. In one embodiment, the sustained release delivery system includes one or more pharmaceutical diluents in an amount of about 50% by weight. In one embodiment, the sustained release delivery system includes one or more pharmaceutical diluents in an amount of about 60% by weight. In one embodiment, the sustained release delivery system includes one or more pharmaceutical diluents in an amount of about 70% by weight.

In a further aspect, the sustained release delivery system includes one or more cationic cross-linking compounds. In some embodiments, the one or more cationic cross-linking compounds are used instead of the cross-linking agent. In some embodiments, the one or more cationic cross-linking compounds are used in addition to the cross-linking agent. In one embodiment, the one or more cationic cross-linking compounds are used in an amount sufficient to cross-link the hydrophilic compound to form a gel matrix in the presence of liquids. In some embodiments, the one or more cationic cross-linking compounds are present in the sustained release delivery system in an amount of about 0.5% to about 30%, about 0.5% to about 25%, about 0.5% to about 20%, about 0.5% to about 15%, about 0.5% to about 10%, or about 0.5% to about 5% by weight. In some embodiments, the one or more cationic cross-linking compounds are present in the sustained release delivery system in an amount of about 5% to about 20%, about 5% to about 15%, about 6% to about 14%, about 7% to about 13%, about 8% to about 12%, or about 9% to about 11% by weight. In some embodiments, the one or more cationic cross-linking compounds are present in the sustained release delivery system in an amount of about 5%, about 6%, about 7%, about 8%, about 9%, about 10%, about 11%, about 12%, about 13%, about 14%, or about 15% by weight. In one embodiment, the cationic cross-linking compound is present in the sustained release delivery system in an amount of about 10% by weight.

Exemplary cationic cross-linking compounds include without limitation monovalent metal cations, multivalent metal cations, and inorganic salts, including alkali metal and/or alkaline earth metal sulfates, chlorides, borates, bromides, citrates, acetates, lactates, and mixtures thereof. For example, the cationic cross-linking compound include without limitation one or more of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures thereof.

When the sustained release delivery system includes at least one hydrophilic compound and at least one cationic cross-linking compound, the weight ratio of hydrophilic compound to cationic cross-linking compound ranges from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In one embodiment, the weight ratio of hydrophilic compound to cationic cross-linking compound ranges from about 1:3 to about 3:1. In some embodiments, the weight ratio of hydrophilic compound to cationic cross-linking compound is about 3:1, about 2.75:1, about 2.5:1, about 2.25:1, about 2:1, about 1.8:1, about 1.6:1, about 1.4:1, about 1.2:1, about 1:1, about 1:1.25, about 1:1.5, or about 1:2. In one embodiment, the weight ratio of hydrophilic compound to cationic cross-linking compound is about 1:1.25. In one embodiment, the weight ratio of hydrophilic compound to cationic cross-linking compound is about 1.2:1. In one embodiment, the weight ratio of hydrophilic compound to cationic cross-linking compound is about 2:1. In one embodiment, the weight ratio of hydrophilic compound to cationic cross-linking compound is about 2.8:1.

In one embodiment, the at least one hydrophilic compound is present in the sustained release delivery system in an amount of about 5% to about 80% by weight; the at least one cationic cross-linking agent is present in the sustained release delivery system in an amount of about 0.5% to about 30% by weight; and the at least one pharmaceutical diluent is present in the sustained release delivery system in an amount of about 20% to about 80% by weight. In another embodiment, the at least one hydrophilic compound is present in the sustained release delivery system in an amount of about 8% to about 30% by weight; the at least one cationic cross-linking agent is present in the sustained release delivery system in an amount of about 10% by weight; and the at least one pharmaceutical diluent is present in the sustained release delivery system in an amount of about 20% to about 70% by weight. In another embodiment, the at least one hydrophilic compound is present in the sustained release delivery system in an amount of about 5% to about 30% by weight; the at least one cationic cross-linking agent is present in the sustained release delivery system in an amount of about 5% to about 20% by weight; and the at least one pharmaceutical diluent is present in the sustained release delivery system in an amount of about 20% to about 85% by weight. In another embodiment, the at least one hydrophilic compound is present in the sustained release delivery system in an amount of about 10% to about 20% by weight; the at least one cationic cross-linking agent is present in the sustained release delivery system in an amount of about 5% to about 15% by weight; and the at least one pharmaceutical diluent is present in the sustained release delivery system in an amount of about 50% to about 85% by weight.

In some embodiments, the at least one hydrophilic compound is present in the sustained release delivery system in an amount of about 8%, about 9%, about 10%, about 11%, about 12%, about 13%, about 14%, about 15%, about 16%, about 17%, about 18%, about 19%, about 20%, about 22%, about 24%, about 26%, about 28%, or about 30% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, about 16%, about 17%, about 18%, about 19%, or about 20%, by weight; and the at least one pharmaceutical diluent is present in the sustained release delivery system in an amount of about 40%, about 45%, about 50%, about 55%, about 60%, about 65%, about 70%, about 80%, or about 85% by weight. In one embodiment, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, by weight; and the at least one pharmaceutical diluent is present in the sustained release delivery system in an amount of about 55%, about 60%, about 65%, about 70%, about 80%, or about 85% by weight. In one embodiment, the at least one hydrophilic compound is present in the sustained release delivery system in an amount of about 8%, about 12%, or about 20% by weight; the at least one cationic cross-linking agent is present in the sustained release delivery system in an amount of about 10%, about 12%, or about 14% by weight; and the at least one pharmaceutical diluent is present in the sustained release delivery system in an amount of about 40%, about 60%, or about 70% by weight.

In one embodiment, the sustained release delivery system includes about 0.5% to about 80% locust bean gum, about 5% to about 80% xanthan gum, about 20% to about 80% mannitol and about 0.5% to 80% calcium sulfate dihydrate. In one embodiment, the sustained release delivery system includes about 12% to about 47% locust bean gum, about 8% to about 31% xanthan gum, about 20% to about 78% mannitol and about 0.5% to 25% calcium sulfate dihydrate. In one embodiment, the sustained release delivery system includes about 15% to about 25% locust bean gum, about 10% to about 20% xanthan gum, about 50% to about 85% mannitol and about 5% to 15% calcium sulfate dihydrate. In one embodiment, the sustained release delivery system includes about 18% locust bean gum, about 12% xanthan gum, about 60% mannitol and about 10% calcium sulfate dihydrate. In one embodiment, the sustained release delivery system includes about 12% locust bean gum, about 8% xanthan gum, about 70% mannitol and about 10% calcium sulfate dihydrate. In one embodiment, the sustained release delivery system includes about 20% locust bean gum, about 30% xanthan gum, about 40% mannitol and about 10% calcium sulfate dihydrate. In one embodiment, the sustained release delivery system includes about 30% locust bean gum, about 20% xanthan gum, about 40% mannitol and about 10% calcium sulfate dihydrate. In one embodiment, the sustained release delivery system includes about 42% locust bean gum, about 28% xanthan gum, about 20% mannitol and about 10% calcium sulfate dihydrate.

Two properties of the components of this sustained release system (e.g., the at least one hydrophilic compound and the at least one cross-linking agent; or the at least one hydrophilic compound and at least one cationic cross-linking compound) are that it forms a gel matrix upon exposure to liquids are fast hydration of the compounds/ agents and the ability to form a gel matrix having a high gel strength. These two properties, which are needed to achieve a slow release gel matrix, are maximized by the particular combination of compounds (e.g., the at least one hydrophilic compound and the at least one cross-linking agent; or the at least one hydrophilic compound and the at least one cationic cross-linking compound). For example, hydrophilic compounds (e.g., xanthan gum) have excellent water-wicking properties that provide fast hydration. The combination of hydrophilic compounds with materials that are capable of cross-linking the rigid helical ordered structure of the hydrophilic compound (e.g., cross-linking agents and/or cationic cross-linking compounds) thereby acts synergistically to provide a higher than expected viscosity (i.e., high gel strength) of the gel matrix.

In some embodiments, the sustained release compositions are further admixed with one or more wetting agents (e.g., polyethoxylated castor oil, polyethoxylated hydrogenated castor oil, polyethoxylated fatty acid from castor oil, polyethoxylated fatty acid from hydrogenated castor oil) one or more lubricants (e.g., magnesium stearate, sodium stearyl fumarate, and the like), one or more buffering agents, one or more colorants, and/or other conventional ingredients.

In some embodiments compositions employed in the present methods can contain additional pharmaceutical excipients. For example, in certain embodiments, fumaric acid can be added to the formulations described herein.

In other embodiments, a non-functional coating, e.g., Opadry®, can be added to the compositions described herein.

In some embodiments, the compositions described herein further include a second hydrophilic compound. In some embodiments, the second hydrophilic compound is a cellulose ether. In some embodiments, the second hydrophilic compound is a hydroxyalkyl cellulose or a carboxyalkyl cellulose. In some embodiments, the second hydrophilic compound is a hydroxyethyl cellulose, a hydroxypropyl cellulose, a hydroxypropylmethyl-cellulose, a carboxy methylcellulose, or a mixture thereof. In some embodiments, the second hydrophilic is an ethyl cellulose or wax (e.g., including without limitation cetyl alcohol, stearyl alcohol, white wax, or carnauba wax). The second hydrophilic compound is present in the formulation in an amount ranging from about 5% to about 45%, about 5% to about 25%, about 10% to about 20%, or 12% to about 18% by weight. In some embodiments, the second hydrophilic compound is present in the formulation in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, or about 45%.

In some embodiments, the weight ratio of the second hydrophilic compound to the nalbuphine or pharmaceutically acceptable salt or ester ranges from about 5:1 to about 1:5, about 4:1 to about 1:4, about 3:1 to about 1:3, about 2:1 to about 1:2, about 1:1 to about 1:3, or about 1:1 to about 1:2. In some embodiments, the weight ratio of the second hydrophilic compound to the nalbuphine or pharmaceutically acceptable salt or ester is about 5:1, about 4:1, about 3:1, about 2:1, about 1:1, about 1:2, about 1:3, about 1:4, or about 1:5.

In some embodiments, the weight ratio of the second hydrophilic compound to the sustained release delivery system ranges from about 10:1 to about 1:10, about 8:1 to about 1:8, about 6:1 to about 1:6, about 4:1 to about 1:4, about 2:1 to about 1:3, about 1:1 to about 1:10, about 1:1 to about 1:6, or about 1:2 to about 1:6. In some embodiments, the weight ratio of the second hydrophilic compound to the sustained release delivery system is about 10:1, about 8:1, about 6:1, about 4:1, about 2:1, about 1:1, about 1:1.5, about 1:2, about 1:2.5, about 1:3, about 1:4, about 1:5, about 1:6, about 1:7, about 1:8, about 1:9 or about 1:10.

In some embodiments, the oral sustained release solid dosage formulations including from about 1 mg to 200 mg nalbuphine hydrochloride and about 10 mg to about 420 mg of a sustained release delivery system. In these embodiments, the sustained release delivery system includes about 12% to about 42% locust bean gum; about 8.0% to about 28% xanthan gum; about 20% to about 70% mannitol; and about 5% to about 20% calcium sulfate dihydrate. In some embodiments, the present methods can employ oral sustained release solid dosage formulations including from about 5 mg to about 80 mg nalbuphine hydrochloride and about 80 mg to about 360 mg of a sustained release delivery system. In some embodiments, the present methods can employ oral sustained release solid dosage formulations including from about 50 mg to about 150 mg nalbuphine hydrochloride and about 100 mg to about 300 mg of a sustained release delivery system.

In some embodiments, the present methods employ oral sustained release solid dosage formulations including about 15 mg nalbuphine hydrochloride, and from about 25 mg to about 225 mg, for example about 195 mg, of a sustained release delivery system. In these embodiments, the sustained release delivery system includes about 14% locust bean gum; about 9% xanthan gum; about 47% mannitol; and about 8% calcium sulfate dihydrate.

In some embodiments, the present methods employ oral sustained release solid dosage formulations including about 30 mg nalbuphine hydrochloride, and from about 25 mg to about 225 mg, for example about 180 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 60 mg nalbuphine hydrochloride, and from about 25 mg to about 225 mg, for example about 120 mg, of a sustained release delivery system. In these embodiments, the sustained release delivery system includes about 10% locust bean gum; about 12% xanthan gum; about 60% mannitol; and about 10% calcium sulfate dihydrate. In some embodiments, the present methods employ oral sustained release solid dosage formulations including from about 5 mg to about 80 mg nalbuphine hydrochloride and about 80 mg to about 360 mg of a sustained release delivery system.

In some embodiments, the present methods employ oral sustained release solid dosage formulations including about 120 mg nalbuphine hydrochloride, and from about 25 mg to about 250 mg, for example about 240 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 30 mg nalbuphine hydrochloride, and from about 25 mg to about 350 mg, for example about 270 mg or about 360 mg, of a sustained release delivery system. In these embodiments, the sustained release delivery system includes about 18% locust bean gum; about 12% xanthan gum; about 60% mannitol; and about 10% calcium sulfate dihydrate.

In some embodiments, the present methods employ oral sustained release solid dosage formulations including about 45 to about 60 mg nalbuphine hydrochloride and from about 100 mg to about 200 mg of a sustained release delivery system. In these embodiments, the sustained release delivery system includes about 15% to about 25% locust bean gum; about 10% to about 20% xanthan gum; about 50% to about 85% mannitol; and about 5% to about 15% calcium sulfate dihydrate.

In some embodiments, the present methods employ oral sustained release solid dosage formulations including about 30 mg nalbuphine hydrochloride, about 32.4 mg locust bean gum; about 21.6 mg xanthan gum; about 108 mg mannitol; about 18 mg calcium sulfate dihydrate, about 35 mg hydroxypropylcellulose, and about 1.9 mg magnesium stearate.

In some embodiments, the present methods employ oral sustained release solid dosage formulations including about 60 mg nalbuphine hydrochloride, about 21.6 mg locust bean gum; about 14.4 mg xanthan gum; about 72 mg mannitol; about 12 mg calcium sulfate dihydrate, about 30 mg hydroxypropylcellulose, and about 1.6 mg magnesium stearate.

In some embodiments, the present methods employ oral sustained release solid dosage formulations including about 120 mg nalbuphine hydrochloride, about 43.2 mg locust bean gum; about 28.8 mg xanthan gum; about 144 mg mannitol; about 24 mg calcium sulfate dihydrate, about 60 mg hydroxypropylcellulose, and about 3.2 mg magnesium stearate.

In some embodiments, the present methods employ oral sustained release solid dosage formulations including about 180 mg nalbuphine hydrochloride, about 64.8 mg locust bean gum; about 43.2 mg xanthan gum; about 216 mg mannitol; about 36 mg calcium sulfate dihydrate, about 90 mg hydroxypropylcellulose, about 5 mg magnesium stearate, and about 25 mg fumaric acid.

In some embodiments, the present methods employ oral sustained release solid dosage formulations including about 180 mg nalbuphine hydrochloride, about 48.6 mg locust bean gum; about 32.4 mg xanthan gum; about 162 mg mannitol; about 27 mg calcium sulfate dihydrate, about 60 mg hydroxypropylcellulose, about 4 mg magnesium stearate, and about 25 mg fumaric acid.

In some embodiments, the present methods employ oral sustained release solid dosage formulations including about 30 mg nalbuphine hydrochloride, about 32.4 mg locust bean gum; about 21.6 mg xanthan gum; about 108 mg mannitol; about 18 mg calcium sulfate dihydrate, about 35 mg hydroxypropylcellulose, about 1.9 mg magnesium stearate, and about 7.4 mg Opadry II White.

The sustained release formulations of nalbuphine are orally administrable solid dosage formulations. Nonlimiting examples of oral solid dosage formulations include tablets, capsules including a plurality of granules, sublingual tablets, powders, granules, syrups, and buccal dosage forms or devices (e.g., buccal patches, tablets, etc.). In some embodiments, tablets have an enteric coating or a hydrophilic coating.

The sustained release delivery system is prepared by dry granulation or wet granulation, before the nalbuphine or pharmaceutically acceptable salt or ester thereof is added, although the components can be held together by an agglomeration technique to produce an acceptable product. In the wet granulation technique, the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules of the sustained release delivery system. Thereafter, the sustained release delivery system is mixed in the desired amounts with the nalbuphine or the pharmaceutically acceptable salt or ester thereof and, optionally, one or more wetting agents, one or more lubricants, one or more buffering agents, one or more coloring agents, one or more second hydrophilic compounds, or other conventional ingredients, to produce a granulated composition. The sustained release delivery system and the nalbuphine can be blended with, for example, a high shear mixer. The nalbuphine is preferably finely and homogeneously dispersed in the sustained release delivery system. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

In some embodiments, the nalbuphine formulation is prepared by dry granulation or wet granulation. The components of the sustained release delivery system are added, along with the nalbuphine or a pharmaceutically acceptable salt or ester thereof. Alternatively, all of the components can be held together by an agglomeration technique to produce an acceptable product. In the wet granulation technique, nalbuphine or pharmaceutically salt or ester thereof and the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules. Optionally, one or more wetting agents, one or more lubricants, one or more buffering agents, one or more coloring agents, one or more second hydrophilic compounds, or other conventional ingredients, are also added to the granulation. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

The average particle size of the granulated composition is from about 50 µm to about 400 gm by weight. In some embodiments, the average particle size by weight is from about 185 µm to about 265 µm. The average density of the granulated composition is from about 0.3 g/mL to about 0.8 g/mL. In some embodiments, the average density is from about 0.5 g/mL to about 0.7 g/mL. The tablets formed from the granulations are generally from about 4 Kp to about 22 Kp hardness. The average flow of the granulations is from about 25 to about 40 g/sec.

In some embodiments, the present methods can employ a multilayer solid dosage form, in which the layers are formulated to release the nalbuphine hydrochloride at different rates. For example, in one embodiment, the second layer is an extended release layer that includes nalbuphine or a pharmaceutically acceptable salt or ester thereof and a sustained release delivery system designed to release the nalbuphine or the pharmaceutically acceptable salt or ester thereof at a controlled rate so that therapeutically beneficial blood levels are maintained over an extended period of time (e.g., from about 8 to about 12 hours). The first layer is an immediate release layer that includes a formulation of nalbuphine or a pharmaceutically acceptable salt or ester thereof designed to release the nalbuphine or the pharmaceutically acceptable salt or ester thereof at a rate that is faster than the rate of the second layer to achieve a therapeutically beneficial blood level in an immediate period of time (e.g., from about 1 to about 2 hours). In some embodiments, the first layer includes a sustained release delivery system. In some embodiments, the first layer does not include a sustained release delivery system.

In some embodiments, the weight ratio of the second layer to the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In one embodiment, the weight ratio of the second layer to the first layer is about 5:1 to about 1:5. In a further embodiment, the weight ratio of the second layer to the first layer is about 1:1 to about 1:2. In some embodiments, the weight ratio of the second layer to the first layer is about 1:1, about 1:1.2, about 1:1.4, about 1:1.6, about 1:1.8, or about 1:2. In one embodiment, the weight ratio of the second layer to the first layer is about 1:2. In one embodiment, the weight ratio of the second layer to the first layer is about 1:1.4. In some embodiments, the weight ratio of the second layer to the first layer is about 3:1, about 2.5:1, about 2:1, about 1.5:1. In one embodiment, the weight ratio of the second layer to the first layer is about 2.5:1.

The sustained release delivery system of the multilayer dosage form includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent. In some embodiments, when the first layer includes a sustained release delivery system, the sustained release delivery system of the first layer includes the same components as the sustained release delivery system of the second layer (e.g., both the first and second layers are one of embodiments (i)-(iii), listed above). In other embodiments, the sustained release delivery system of the first layer includes different components as the sustained release delivery system of the second layer (e.g., the first layer is embodiment (i), listed above, while the second layer is embodiment (iii), listed above). It is recognized that the sustained release delivery system of either layer can be one of embodiments (i)-(iii) listed above. Moreover, it is recognized that in some embodiments, the first layer does not include a sustained release delivery system.

The sustained release delivery system is generally present in the second layer (e.g., extended release layer) in an amount ranging from about 10 mg to about 420 mg. In some embodiments, the sustained release delivery system is present in the second layer in an amount ranging from about 110 mg to about 200 mg. In some embodiments, the sustained release delivery system is present in the second layer in an amount ranging from about 110 mg to about 150 mg. In some embodiments, the sustained release delivery system is present in the second layer in an amount ranging from about 90 mg to about 150 mg. In some embodiments, the sustained release delivery system is present in the second layer in an amount of about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg. In one embodiment, the sustained release delivery system is present in the second layer in an amount of about 123 mg. In one embodiment, the sustained release delivery system is present in the second layer in an amount of about 101 mg. In one embodiment, the sustained release delivery system is present in the second layer in an amount of about 92 mg. In another embodiment, the sustained release delivery system is present in the second layer in an amount of about 112.5 mg. In one embodiment, the sustained release delivery system is present in the second layer in an amount of about 135 mg. In one embodiment, the sustained release delivery system is present in the second layer in an amount of about 150 mg.

Nalbuphine or a pharmaceutically acceptable salt or ester thereof is generally present in the second layer in an amount ranging from about 15 mg to about 60 mg. In some embodiments, nalbuphine or a pharmaceutically acceptable salt or ester thereof is present in the second layer in an amount ranging from about 30 mg to about 60 mg. In some embodiments, nalbuphine or a pharmaceutically acceptable salt or ester thereof is present in the second layer in an amount ranging from about 45 mg to about 60 mg. In one embodiment, nalbuphine or a pharmaceutically acceptable salt or ester thereof is present in the second layer in an amount of about 15 mg. In one embodiment, nalbuphine or a pharmaceutically acceptable salt or ester thereof is present in the second layer in an amount of about 30 mg. In one embodiment, nalbuphine or a pharmaceutically acceptable salt or ester thereof is present in the second layer in an amount of about 45 mg. In one embodiment, nalbuphine or a pharmaceutically acceptable salt or ester thereof is present in the second layer in an amount of about 15 mg, about 30 mg, about 90 mg, about 120 mg, or about 180 mg.

In some embodiments, the weight ratio of nalbuphine or a pharmaceutically acceptable salt or ester thereof to the sustained release delivery system in the second layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2. In one embodiment, the weight ratio of nalbuphine or a pharmaceutically acceptable salt or ester thereof to the sustained release delivery system in the second layer is about 1:2 to about 1:4. In one embodiment, the weight ratio of nalbuphine or a pharmaceutically acceptable salt or ester thereof to the sustained release delivery system in the second layer is about 1:1 to about 1:5. In some embodiments, the weight ratio of nalbuphine or a pharmaceutically acceptable salt or ester thereof to the sustained release delivery system in the second layer is about 1:1, about 1:1.2, about 1:1.4, about 1:1.6, about 1:1.8, about 1:2, about 1:2.5, about 1:3, or about 1:3.5. In one embodiment, the weight ratio of nalbuphine or a pharmaceutically acceptable salt or ester thereof to the sustained release delivery system in the second layer is about 1:2.5. In another embodiment, the weight ratio of nalbuphine or a pharmaceutically acceptable salt or ester thereof to the sustained release delivery system in the second layer is about 1:3.3. In a further embodiment, the weight ratio of nalbuphine or a pharmaceutically acceptable salt or ester thereof to the sustained release delivery system in the second layer is about 1:3. In yet another embodiment, the ratio of nalbuphine or a pharmaceutically acceptable salt or ester thereof to the sustained release delivery system in the second layer is about 1:2.

When the sustained release delivery system is present in the first layer (e.g., immediate release layer), it is generally present in an amount ranging from about 0 mg to about 50 mg. In some embodiments, the sustained release delivery system is present in the first layer in an amount ranging from about 5 mg to about 25 mg or from about 5 mg to about 15 mg. In one embodiment, the sustained release delivery system is present in the first layer in an amount of about 3 mg to about 9 mg. In one embodiment, the sustained release delivery system is present in the first layer in an amount of about 4 mg to about 6 mg. In some embodiments, the sustained release delivery system is present in the first layer in an amount of about 2 mg, about 4 mg, about 6 mg, about 8 mg, about 10 mg, about 12 mg, about 14 mg, about 15 mg, about 16 mg, about 18 mg, about 20 mg about 25 mg, about 30 mg, about 35 mg, about 40 mg, about 45 mg or about 50 mg. In one embodiment, the sustained release delivery system is present in the first layer in an amount of about 6 mg.

In some embodiments, nalbuphine or a pharmaceutically acceptable salt or ester thereof is generally present in the first layer (e.g., immediate release layer) in an amount ranging from about 5 mg to about 180 mg. In some embodiments, nalbuphine or a pharmaceutically acceptable salt or ester thereof is present in the first layer in an amount ranging from about 5 mg to about 25 mg or from about 10 mg to about 20 mg. In some embodiments, the nalbuphine or a pharmaceutically acceptable salt or ester thereof is present in the first layer in an amount of about 5 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg or about 50 mg. In one embodiment, nalbuphine or a pharmaceutically acceptable salt or ester thereof is present in the first layer in an amount of about 15 mg, about 30 mg, about 90 mg, about 120 mg, or about 180 mg.

In some embodiments, when the first layer includes a sustained release delivery system, the ratio of nalbuphine or pharmaceutically acceptable salt or ester thereof to the sustained release delivery system in the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In one embodiment, the ratio of nalbuphine or pharmaceutically acceptable salt or ester thereof to the sustained release delivery system in the first layer is about 2:1 to about 4:1. In some embodiments, the ratio of nalbuphine or pharmaceutically acceptable salt or ester thereof to the sustained release delivery system in the first layer is about 5:1, about 4.5:1, about 4:1, about 3.5:1, about 3:1, about 2.5:1, about 2:1, about 1.5:1, or about 1:1. In one embodiment, the ratio of nalbuphine or pharmaceutically acceptable salt or ester thereof to the sustained release delivery system in the first layer is about 2.5:1. In another embodiment, the ratio of nalbuphine or pharmaceutically acceptable salt or ester thereof to the sustained release delivery system in the first layer is about 3:1.

In some embodiments, the multilayer dosage form further includes a pharmaceutical disintegrant. The disintegrant promotes the dissolution and absorption of nalbuphine or pharmaceutically acceptable salt or ester thereof from the immediate release layer. Nonlimiting examples of pharmaceutical disintegrants include croscarmellose sodium, starch glycolate, crospovidone, and unmodified starch. In one embodiment, the disintegrant is in the first layer (i.e., the immediate release layer), of the dosage form. The disintegrant is generally present in the layer in an amount of about 1.5 mg to about 4.5 mg. In one embodiment, the disintegrant is present in an amount of about 3 mg. In one embodiment, the disintegrant is present in the layer in an amount of about 2-10% by weight. In one embodiment, the disintegrant is present in the layer in an amount of about 5% by weight. When the layer contains a sustained release delivery system, the weight ratio of the sustained release delivery system to the disintegrant is in a range of about 5:1 to about 1:5. In some embodiments, the ratio of the sustained release delivery system to the disintegrant is in a range of about 1:1 to about 3:1. In other embodiments, the ratio of the sustained release delivery system to the disintegrant is in a range of about 2:1.

In some embodiments, the multilayer tablets are prepared by first preparing the immediate release layer and extended release layer blends separately. The extended release layer is prepared as described above. The wet granulation of the extended release layer is then dried and milled to an appropriate size. Magnesium stearate is added and mixed with the milled granulation. The immediate release layer is prepared by first mixing the nalbuphine or the pharmaceutically acceptable salt or ester thereof with one or more diluents (e.g., microcrystalline cellulose). This mix is then optionally mixed with one or more disintegrants. The blend is mixed with magnesium stearate. Finally, the immediate release layer blend and the extended release layer blend are compressed into multi-layer (e.g., bi-layer) tablets.

The invention provides methods for treating pruritus by administering an effective amount, e.g., an effective amount of a sustained release formulation of nalbuphine or a pharmaceutically acceptable salt or ester thereof to a subject, e.g., human or animal patient in need thereof. An effective amount is an amount sufficient to eliminate or significantly reduce pruritus symptoms or to alleviate those symptoms (e.g., reduce the symptoms, such as itching, compared to the symptoms present prior to administration of the nalbuphine sustained release formulation). "Sustained release" or "extended release" means that the nalbuphine or pharmaceutically acceptable salt or ester thereof is released from the formulation at a controlled rate so that therapeutically beneficial blood levels (but below toxic levels) of the nalbuphine or pharmaceutically acceptable salt or ester thereof are maintained over an extended period of time. Alternatively, "sustained release" or "extended release" means that the desired pharmacologic effect is maintained over an extended period of time. Clinical trials of the formulations described herein find that the duration of relief of pruritus symptoms is longer than expected. The half-life of experimental orally administered nalbuphine formulations (i.e., immediate release formulations) has been reported to be relatively short, only about 5-7 hours. Moreover, the published literature suggests that the duration of effect for experimental formulations of immediate release nalbuphine was only about 4 hours. Based on these data, it was expected that a sustained release formulation would provide a duration of anti-pruritic effect for approximately 6-8 hours, i.e., allowing for 2-3 times daily dosing. In the clinical trials described herein, however, nalbuphine sustained release formulations have an anti-pruritic effect of longer than 8 hours. In some cases, the duration of anti-pruritic effect is at least about 12 hours, thus providing the possibility of fewer dosing administrations.

Without wishing to be bound by a particular theory, the longer than expected duration of anti-pruritic effect is attributed to the enterohepatic recirculation of nalbuphine. Nalbuphine forms a glucuronic acid or other type of conjugated metabolite in vivo through enzymatic reaction with an enzyme system such as UDP-glucuronyl transferase. It is also possible that enterohepatic recirculation also occurs when parent drug in the bile is released from the gallbladder into the intestine and reabsorbed. Once formed, the conjugated nalbuphine product is thought to be transported into the gastrointestinal tract via biliary secretion whereby the drug conjugate is cleaved liberating nalbuphine which can be reabsorbed from the intestine. The sustained release formulation can improve the duration of anti-pruritic effect, by more slowly releasing nalbuphine into the in vivo system and allowing more drug to be conjugated and therefore available for recirculation and later reabsorption from the intestine.

In certain embodiments, the chemistry of certain of the components of the formulation, such as the hydrophilic compound (e.g., xanthan gum), is such that the components are considered to be self-buffering agents which are substantially insensitive to the solubility of the nalbuphine and the pH changes along the length of the gastrointestinal tract. Moreover, the chemistry of the components is believed to be similar to certain known muco-adhesive substances, such as polycarbophil. Muco-adhesive properties are desirable for buccal delivery systems. Thus, the sustained release formulation can loosely interact with the mucin in the gastrointestinal tract and thereby provide another mode by which a constant rate of delivery of the nalbuphine is achieved.

The two phenomenon discussed above (buoyancy and muco-adhesive properties) are mechanisms by which the sustained release formulations can interact with the mucin and fluids of the gastrointestinal tract and provide a constant rate of delivery of the nalbuphine.

When measured by USP Procedure Drug Release General Chapter <711> Dissolution, (incorporated by reference herein in its entirety), the sustained release formulations employed in the present methods generally exhibit an in vitro dissolution of about 15% to about 50% by weight nalbuphine after 1 hour, about 45% to about 80% by weight nalbuphine after 4 hours, or at least about 80% by weight nalbuphine after 10 hours. In some embodiments, the in vitro and in vivo release characteristics of the sustained release formulations are modified using mixtures of one or more different water insoluble and/or water soluble compounds, using different plasticizers, varying the thickness of the sustained release film, including providing release-modifying compounds in the coating, and/or by providing passageways through the coating. In some embodiments, the dissolution rate is determined using apparatus USP Type III/250 mL at pH 6.8, 37° C. and 15 dpm. In some embodiments, the dissolution rate is determined using apparatus USP Type III/250 mL performed in pH change (0-1 hours pH 1.2, after hour 1 pH 4.5, after hour 2 pH 6.8) at 37° C. and 15 dpm.

In some embodiments, the sustained release formulation has an in vitro dissolution of about 50% to about 100% by weight nalbuphine after about 6 hours. In some embodiments, the sustained release formulation has an in vitro dissolution of about 75% to about 100% by weight nalbuphine after about 6 hours. In other embodiments, the sustained release formulation has an in vitro dissolution of about 75% to about 100% by weight nalbuphine from about 6 hours to about 8 hours. In further embodiments, the sustained release formulation has an in vitro dissolution of about 80% to about 100% by weight nalbuphine after about 12 hours. In still other embodiments, the sustained release formulation has an in vitro dissolution of about 80% to about 100% by weight nalbuphine from about 12 hours to about 24 hours. In some embodiments, the sustained release formulation has an in vitro dissolution of about 80% to about 100% after about 8 hours to about 12 hours. In yet other embodiments, the sustained release formulation has an in vitro dissolution of about 15% to about 75% by weight nalbuphine after about 1 hour. In still further embodiments, the sustained release formulation has an in vitro dissolution of about 50% by weight nalbuphine after about 1 hour. In some embodiments, the sustained release formulation has an in vitro dissolution of about 50% by weight nalbuphine after about 1 hour and about 75% to about 100% by weight nalbuphine from about 6 hours to about 8 hours. In some embodiments, the sustained release formulation has an in vitro dissolution of about 50% by weight nalbuphine after about 1 hour and about 75% to about 100% by weight nalbuphine from about 8 hours to about 12 hours. In some embodiments, the sustained release formulation has an in vitro dissolution of about 50% by weight nalbuphine after about 1 hour and about 75% to about 100% by weight nalbuphine from about 12 hours to about 24 hours. In some embodiments, the sustained release formulation has an in vitro dissolution of about 50% by weight nalbuphine after about 1 hour and about 80% to about 100% by weight nalbuphine after about 12 hours.

Where the tablet is a multilayer dosage form having a first extended release layer and a second, immediate release, layer, the sustained release formulation has an in vitro dissolution of about 25% to about 75% by weight nalbuphine after about 1 hour. In some embodiments, the multilayer dosage form has an in vitro dissolution of about 25% by weight nalbuphine after about 1 hour. In some embodiments, the multilayer dosage form has an in vitro dissolution of about 50% by weight nalbuphine after about 1 hour. In some embodiments, the multilayer dosage form has an in vitro dissolution of about 75% to about 100% nalbuphine after about 6-8 hours. In some embodiments, the multilayer dosage form has an in vitro dissolution of about 75% to about 100% nalbuphine after about 8-12 hours. In some embodiments, the multilayer dosage form has an in vitro dissolution of about 75% to about 100% nalbuphine after about 12-24 hours. In some embodiments, the multilayer dosage form has an in vitro dissolution of about 75% to about 100% nalbuphine after about 12 hours.

When administered orally to patients having either normal or impaired (e.g., reduced) kidney function, the sustained release formulations described herein exhibit the following in vivo characteristics: (a) a peak plasma level of nalbuphine occurs within about 4 hours to about 6 hours, e.g., for subjects with uremic pruritus or renal impairment, or about 3 hours to about 5 hours, e.g., for subjects without renal impairment after administration; (b) onset of nalbuphine anti-pruritic effect from about 30 minutes of dosing to within about 6 hours of dosing; (c) duration of the nalbuphine anti-pruritic effect is about 2 to about 24 hours; and (d) the relative nalbuphine bioavailability is about 0.5, about 1, about 1.5 or between about 0.5 to about 1.5 compared to an orally administered aqueous solution of nalbuphine. The time of onset for an anti-pruritic effect can depend on at least on dosing and the severity of pruritic symptoms. In some embodiments, the duration of the nalbuphine anti-pruritic effect is at least about 8 hours. In some embodiments, the duration of the nalbuphine anti-pruritic effect is at least about 9 hours. In some embodiments, the duration of the nalbuphine anti-pruritic effect is at least about 10 hours. In some embodiments, the duration of the nalbuphine anti-pruritic effect is at least about 11 hours. In some embodiments, the duration of the nalbuphine anti-pruritic effect is at least about 12 hours. In some embodiments, the duration of nalbuphine anti-pruritic effect is about 6, hours, 8 hours, 10 hours, 12 hours, 15 hours, or 18 hours. In some embodiments, the relative nalbuphine bioavailability is about 0.94 compared to an orally administered aqueous solution of nalbuphine. In some embodiments, the relative nalbuphine bioavailability is about 1.35 compared to an orally administered aqueous solution of nalbuphine.

In some embodiments, the sustained release nalbuphine formulations provide an oral unit dosage form including nalbuphine or a pharmaceutically acceptable salt or ester thereof. The oral dosage form provides an anti-pruritic effect over a period of at least about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours. In some embodiments, the oral dosage form provides an anti-pruritic effect over a period of about 6-18 hours, about 8-16 hours, about 8-12 hours, about 8 to about 24 hours, about 12 to about 24 hours, about 18 to about 24 hours, or about 8-10 hours. The oral dosage form provides an anti-pruritic effect over a period of about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours.

In one embodiment, the oral dosage form provides an anti-pruritic effect as well as breaking the cycle effect, e.g., the itchy sensation does not return after certain treatment period.

In some embodiments, the oral dosage form provides a blood plasma level of nalbuphine characterized by one or more peaks followed by a plateau region. The plateau region is characterized as having a relatively consistent blood plasma level of nalbuphine (e.g., the blood plasma level of nalbuphine does not consistently increase or decrease from time point to time point). In some embodiments, the plateau region is characterized as having a consistent average blood plasma level of nalbuphine. The plateau region is contrasted with the region following the plateau region, in which the blood plasma level of nalbuphine generally decreases from one time point to the next. In some embodiments, the plateau region has a duration of at least about 1 hour, about 2 hours, about 3 hours, about 4 hours, about 5 hours, about 6 hours, about 7 hours, about 8 hours, about 9 hours, about 10 hours, about 11 hours or about 12 hours. In some embodiments, the plateau region has a duration from about 1 hour to about 12 hours, from about 2 hours to about 10 hours, from about 2 hours to about 8 hours, from about 2 hours to about 7 hours or from about 4 hours to about 10 hours, from about 4 hours to about 8 hours, or from about 4 hours to about 6 hours. In some embodiments, the blood plasma level of nalbuphine at each time point in the plateau region ranges from about 75% to about 125% of the mean blood plasma level in the plateau region. In some embodiments, the blood plasma level of nalbuphine at each time point in the plateau region ranges from about 80% to about 120% of the mean blood plasma level in the plateau region. In some embodiments, the blood plasma level of nalbuphine at each time point in the plateau region ranges from about 85% to about 115% of the mean blood plasma level in the plateau region. In some embodiments, the blood plasma level of nalbuphine at each time point in the plateau region ranges from about 90% to about 110% of the mean blood plasma level in the plateau region.

In some embodiments, the minimum blood plasma level of nalbuphine observed during the plateau region is not more than about 25% below the mean blood plasma level for all time points in the plateau region. In some embodiments, the minimum blood plasma level of nalbuphine observed during the plateau region is not more than about 20% below the mean blood plasma level in the plateau region. In some embodiments, the minimum blood plasma level of nalbuphine observed during the plateau region is not more than about 15% below the mean blood plasma level in the plateau region. In some embodiments, the minimum blood plasma level of nalbuphine observed during the plateau region ranges from about 75% to about 100% of the mean blood plasma level in the plateau region. In some embodiments, the minimum blood plasma level of nalbuphine observed during the plateau region ranges from about 80% to about 100% of the mean blood plasma level in the plateau region. In some embodiments, the minimum blood plasma level of nalbuphine observed during the plateau region ranges from about 85% to about 100% of the mean blood plasma level in the plateau region. In some embodiments, the minimum blood plasma level of nalbuphine observed during the plateau region ranges from about 80% to about 95% of the mean blood plasma level in the plateau region.

Co-Therapy

While the compositions can be administered as the sole active pharmaceutical ingredient or sole active anti-pruritus ingredient in the methods described herein, in other embodiments they can also be used in combination with one or more ingredients which are known to be therapeutically effective against pruritus and/or compliment the effect of anti-pruritus ingredient.

For example, in some embodiments, the present methods can employ nalbuphine or a pharmaceutically acceptable salt or ester thereof in conjunction with one or more anti-pruritic agents. In some embodiments, additional compounds combined with the anti-pruritic agent, e.g., nalbuphine, or a pharmaceutically acceptable salt or ester thereof, include antihistamines, anti-inflammatory corticosteroids, topical anti-infectives and antifungals, antibacterials, and antivirals, cytotoxic agents, and counter-irritants/analgesics. Other antipruritic agents include anti-depressants, vitamin D, kappa agonists, irritants such as coal tar derivatives and psoralens, 5-HT3 antagonists such as ondansetron, H2 receptor antagonist such as cimetidine, H1 receptor antagonist such as cetirizine, immunomodulators such as tacrolimus, immunosupressants such as cyclosporine A, µ-antagonists, capsaicin, cannabinoids, latex extracts from various Croton species found in the Amazon jungle (e.g., Zangrado®), or Nk1 antagonists, etc. In some embodiments, nalbuphine or a pharmaceutically acceptable salt or ester thereof is not administered in combination with a second anti-pruritus agent, e.g., co-formulated or administered separately.

Dosing

Formulations employed in the present methods can incorporate nalbuphine in a controlled release formulation such that the formulation provides therapeutically effective blood plasma levels of nalbuphine for the treatment of pruritus. A dosing regimen can be selected for administration of the formulation on a once a day basis, a twice a day basis, thrice a day basis, or four times a day basis. The frequency of dosing can be selected to provide a target plasma concentration of nalbuphine to provide effective relief of the symptoms of pruritus.

In some embodiments, the total daily dose of nalbuphine, either as a single dose or as the sum of two, three or four doses, can range from about 15 mg a day to about 480 mg a day (e.g., about 15 mg a day, about 20 mg a day, about 25 mg a day, about 30 mg a day, about 35 mg a day, about 40 mg a day, about 45 mg a day, about 50 mg a day, about 55 mg a day, about 60 mg a day, about 65 mg a day, about 70 mg a day, about 75 mg a day, about 80 mg a day, about 85 mg a day, about 90 mg a day, about 95 mg a day, about 100 mg a day, about 105 mg a day, about 110 mg a day, about 115 mg a day, about 120 mg a day, about 125 mg a day, about 130 mg a day, about 135 mg a day, about 140 mg a day, about 145 mg a day, about 150 mg a day, about 155 mg a day, about 160 mg a day, about 165 mg a day, about 170 mg a day, about 175 mg a day, about 180 mg a day, about 185 mg a day, about 190 mg a day, about 195 mg a day, about 200 mg a day, about 205 mg a day, about 210 mg a day, about 215 mg a day, about 220 mg a day, about 225 mg a day, about 230 mg a day, about 235 mg a day, about 240 mg a day, about 245 mg a day, about 250 mg a day, about 255 mg a day, about 260 mg a day, about 265 mg a day, about 270 mg a day, about 275 mg a day, about 280 mg a day, about 285 mg a day, about 290 mg a day, about 295 mg a day, about 300 mg a day, about 305 mg a day, about 310 mg a day, about 315 mg a day, about 320 mg a day, about 325 mg a day, about 330 mg a day, about 335 mg a day, about 340 mg a day, about 345 mg a day, about 350 mg a day, about 355 mg a day, about 360 mg a day, about 380 mg, about 400 mg, about 420 mg, about 440 mg, about 460 mg, about 480 mg a day or any other value or range of values therein).

In one embodiment, the total daily dose of nalbuphine, either as a single dose or as the sum of two, three or four doses is 15 mg, 30 mg, 60 mg, 120 mg, 240 mg, 360 mg, or 480 mg. For example, the total daily dose of nalbuphine, either as a single dose or the sum of two doses is 120 mg or 240 mg for the treatment of uremic pruritus. In another example, the total daily dose of nalbuphine, either as a single dose or the sum of two doses is 180 mg or 360 mg for the treatment of a subject who does not have any renal impairment.

In some embodiments, the maximum total daily dose of nalbuphine or a pharmaceutically acceptable salt or ester thereof is about 75 mg to about 180 mg, administered once a day, for example about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, or about 180 mg, administered once a day, including all values or ranges there between.

In some embodiments, the maximum total daily dose of nalbuphine or a pharmaceutically acceptable salt or ester thereof is about 90 mg to about 360 mg, administered once a day, for example about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about to 60 mg, about 270 mg, about 280 mg, about 290 mg, about 300 mg, about 310 mg, about 320 mg, about 330 mg, about 340 mg, about 350 mg, in about 360 mg, including all values or ranges there between.

In some other embodiments, the maximum total daily dose of nalbuphine or a pharmaceutically acceptable salt or ester thereof is about 480 mg for a subject either with renal impairment or without renal impairment.

In some embodiments, the dosing regimen is a twice-daily dose of a controlled release formulation, and the amount of nalbuphine in the controlled release formulation is from about 15 mg to about 180 mg (e.g., about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein). A twice-daily dosage regimen may include a total daily dosage over the two administrations of from about 15 mg a day to about 360 mg a day (e.g., about 15 mg a day, about 20 mg a day, about 25 mg a day, about 30 mg a day, about 35 mg a day, about 40 mg a day, about 45 mg a day, about 50 mg a day, about 55 mg a day, about 60 mg a day, about 65 mg a day, about 70 mg a day, about 75 mg a day, about 80 mg a day, about 85 mg a day, about 90 mg a day, about 95 mg a day, about 100 mg a day, about 105 mg a day, about 110 mg a day, about 115 mg a day, about 120 mg a day, about 125 mg a day, about 130 mg a day, about 135 mg a day, about 140 mg a day, about 145 mg a day, about 150 mg a day, about 155 mg a day, about 160 mg a day, about 165 mg a day, about 170 mg a day, about 175 mg a day, about 180 mg a day, about 185 mg a day, about 190 mg a day, about 195 mg a day, about 200 mg a day, about 205 mg a day, about 210 mg a day, about 215 mg a day, about 220 mg a day, about 225 mg a day, about 230 mg a day, about 235 mg a day, about 240 mg a day, about 245 mg a day, about 250 mg a day, about 255 mg a day, about 260 mg a day, about 265 mg a day, about 270 mg a day, about 275 mg a day, about 280 mg a day, about 285 mg a day, about 290 mg a day, about 295 mg a day, about 300 mg a day, about 305 mg a day, about 310 mg a day, about 315 mg a day, about 320 mg a day, about 325 mg a day, about 330 mg a day, about 335 mg a day, about 340 mg a day, about 345 mg a day, about 350 mg a day, about 355 mg a day, about 360 mg a day, or any other value or range of values therein).

In some embodiments, a twice-daily dosage regimen may include a total daily dosage over the two administrations of from about 60 mg, to about 120 mg, to about 240 mg, to about 360 mg or to about 480 mg.

In some embodiments, a twice-daily dosage regimen may include a total daily dosage over the two administrations of from about 120 mg to 240 mg for subjects with any renal impairment or from about 180 mg to about 360 mg for subject without any renal impairment.

In some embodiments, the dosing regimen is a thrice-daily dose of a controlled release formulation, and the amount of nalbuphine in the controlled release formulation is from about 15 mg to about 180 mg (e.g., about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein). A thrice-daily dosage regimen may include a total daily dosage over the three administrations of from about 15 mg a day to about 360 mg a day (e.g., about 15 mg a day, about 20 mg a day, about 25 mg a day, about 30 mg a day, about 35 mg a day, about 40 mg a day, about 45 mg a day, about 50 mg a day, about 55 mg a day, about 60 mg a day, about 65 mg a day, about 70 mg a day, about 75 mg a day, about 80 mg a day, about 85 mg a day, about 90 mg a day, about 95 mg a day, about 100 mg a day, about 105 mg a day, about 110 mg a day, about 115 mg a day, about 120 mg a day, about 125 mg a day, about 130 mg a day, about 135 mg a day, about 140 mg a day, about 145 mg a day, about 150 mg a day, about 155 mg a day, about 160 mg a day, about 165 mg a day, about 170 mg a day, about 175 mg a day, about 180 mg a day, about 185 mg a day, about 190 mg a day, about 195 mg a day, about 200 mg a day, about 205 mg a day, about 210 mg a day, about 215 mg a day, about 220 mg a day, about 225 mg a day, about 230 mg a day, about 235 mg a day, about 240 mg a day, about 245 mg a day, about 250 mg a day, about 255 mg a day, about 260 mg a day, about 265 mg a day, about 270 mg a day, about 275 mg a day, about 280 mg a day, about 285 mg a day, about 290 mg a day, about 295 mg a day, about 300 mg a day, about 305 mg a day, about 310 mg a day, about 315 mg a day, about 320 mg a day, about 325 mg a day, about 330 mg a day, about 335 mg a day, about 340 mg a day, about 345 mg a day, about 350 mg a day, about 355 mg a day, about 360 mg a day, or any other value or range of values therein).

In some embodiments, the dosing regimen is a once-daily dose, and the amount of nalbuphine in the formulation is from about 15 mg to about 180 mg (e.g., about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein).

In some embodiments, irrespective of the dosing regimen, the controlled release formulation comprises nalbuphine or a pharmaceutically acceptable salt or ester thereof of about 15 mg, about 30 mg, about 60 mg, about 90 mg, about 120 mg, or about 180 mg.

In some embodiments, the daily dose of nalbuphine can be selected as described above, in either a once-daily dose, a twice daily dose, or a thrice-daily dose, and then titrated upward until the patient experiences satisfactory relief from the pruritic condition. Titrating the dose can include administering a baseline daily dose, in either a once-daily dose, a twice daily dose, or a thrice daily dose, then after a period of observation at the baseline daily dose value to determine the efficacy of the baseline first daily dose and/or side effect severity, increasing the first daily dose if the subject does not experience adequate symptom relief. The period of observation at the baseline daily dose before increasing the daily dose can be from about 1 day to about 21 days (e.g., about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days). The daily dose can be titrated in increments ranging from about 5 mg to about 180 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein). The daily dose can be titrated in one or more steps. The daily dosage can be titrated by increasing a single daily dosage, or each dose of a twice-daily dosing regimen. The amount a dosage is stepped, where there are multiple titration steps, can be the same, or can be different. In some embodiments, a dosage in, e.g., a twice-daily or thrice-daily dosing regimen can be titrated downward, while the corresponding second dose (e.g., in a twice-daily regimen) or the corresponding second and third doses (e.g., in a twice-daily regimen) can independently be held constant or increased, to reduce the total number of doses per day while retaining therapeutic efficacy.

In some embodiments, nalbuphine or a pharmaceutically acceptable salt or ester is administered once a day at about 15 mg to about 30 mg, then twice a day at about 30 mg per dose for about 2 to 3 days, and then increased to twice a day at about 60 mg or 120 mg per dose, e.g., for subjects with uremic pruritus or renal impairment. In some other embodiments, nalbuphine or a pharmaceutically acceptable salt or ester is administered once a day at about 15-30 mg, then twice a day at about 30 mg per dose for about 2 to 3 days, and then increased to twice a day at about 90 mg or 180 mg per dose, e.g., for subjects without any renal impairment.

When nalbuphine HCl solution is administered with food, AUC is relatively unchanged whereas Cmax values are about 1.5 fold higher in the fed than the fasted state. Exposure (AUC) following tablets was comparable to that from the solution with a relative bioavailability of 94% under fasted state. On the other hand, with sustained release nalbuphine formulations, Cmax was blunted (~50%) and Tmax prolonged both in the fed and fasted state relative to the nalbuphine HCl solution. Following oral administration of an aqueous solution, nalbuphine was readily absorbed with a median Tmax of 0.5-1 hr and a mean plasma half-life ($T_{1/2}$) ranging between 6.87 and 6.99 hr across studies under fasted conditions.

In some embodiments, the dosing frequency and dose amount per administration are selected to provide therapeutically effective blood plasma levels of nalbuphine for the treatment of pruritus when administered on a once-a-day basis. For example, in certain embodiments, the controlled release formulation, provides a mean $C_{max}$ of from about 1.0 to about 120 ng/mL for example a mean $C_{max}$ of about 1.0, about 1.1, about 1.2, about 1.3, about 1.4, about 1.5, about 1.6, about 1.7, about 1.8, about 1.9, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8, about 5.0, about 5.2, about 5.4, about 5.6, about 5.8, about 6.0, about 6.2, about 6.4, about 6.6, about 6.8, about 7.0, about 7.2, about 7.4, about 7.6, about 7.8, about 8.0, about 8.2, about 8.4, about 8.6, about 8.8, about 9.0, about 9.2, about 9.4, about 9.6, about 9.8, about 10, about 11, about 12, about 13, about 14, about 15, about 16, about 17, about 18, about 19, about 20, about 21, about 22, about 23, about 24, about 25, about 26, about 27, about 28, about 29, about 30, 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, 81, about 82, about 83, about 84, about 85, about 86, about 87, about 88, about 89, about 90, about 91, about 92, about 93, about 94, about 95, about 96, about 97, about 98, about 99, about 100, about 101, about 102, about 1 to 3, about 104, about 105, about 16, about 107, about 108, about 109, about 110, about 111, about 112, about 113, about 114, about 115, about 116, about 117, about 118, about 119, about 120 ng/mL, or any other value or range of values therein.

In one embodiment, the controlled release formulation provides a mean $C_{max}$ of from about 1.9 ng/mL to about 102 ng/mL. In another embodiment, the controlled release formulation provides a mean $C_{max}$ of from about 30 ng/mL to about 60 ng/mL. In yet another embodiment, the controlled release formulation provides a mean $C_{max}$ of from about 2 ng/mL to about 15 ng/mL. In yet another embodiment, the controlled release formulation provides a mean $C_{max}$ of from about 5 ng/mL to about 10 ng/mL. In still other embodiments, the controlled release formulation provides a mean $C_{max}$ of from about 10 ng/mL to about 20 ng/mL. In still other embodiments, the controlled release formulation provides a mean $C_{max}$ of from about 20 ng/mL to about 30 ng/mL. In still other embodiments, the controlled release formulation provides a mean $C_{max}$ of from about 30 ng/mL to about 50 ng/mL. In still other embodiments, the controlled release formulation provides a mean $C_{max}$ of from about 50 ng/mL to about 60 ng/mL.

In one embodiment, the controlled release formulation provides a mean $C_{max}$ of from about 5 ng/mL to about 85 ng/mL, e.g., for subjects with uremic pruritus or renal impairment or from about 5 ng/mL to about 45 ng/mL, e.g., for subjects without any renal impairment. For example, the controlled release formulation provides a mean $C_{max}$ of from about 24 ng/mL to about 71 ng/mL, e.g., for subjects with uremic pruritus or renal impairment or from about 13 ng/mL to about 28 ng/mL, e.g., for subjects without any renal impairment In other embodiments, the present formulations provide a mean Cmax from about 0.088 (ng/mL)/mg to about 0.245 (ng/mL)/mg (e.g., about 0.08 (ng/mL)/mg, about 0.09 (ng/mL)/mg, about 0.1 (ng/mL)/mg, about 0.11 (ng/mL)/mg, about 0.12 (ng/mL)/mg, about 0.13 (ng/mL)/mg, about 0.14 (ng/mL)/mg, about 0.15 (ng/mL)/mg, about 0.16 (ng/mL)/mg, about 0.17 (ng/mL)/mg, about 0.18 (ng/mL)/mg, about 0.19 (ng/mL)/mg, about 0.20 (ng/mL)/mg, about 0.21 (ng/mL)/mg, about 0.22 (ng/mL)/mg, about 0.23 (ng/mL)/mg, about 0.24 (ng/mL)/mg, or any other value or range of values therein). In some embodiments, the present formulations provide a mean Cmax from about 0.15 (ng/mL)/mg to about 0.35 (ng/mL)/mg. For example, according to the present invention the sustained release formulation can have a mean Cmax from about 0.2 (ng/mL)/mg to about 0.3 (ng/mL)/mg.

In one embodiment, the present formulations provide a mean Cmax from about 0.2 (ng/mL)/mg to about 0.6 (ng/mL)/mg, e.g., for subjects with uremic pruritus or renal impairment or from about 0.15 (ng/mL)/mg to about 0.25 (ng/mL)/mg, e.g., for subjects without any renal impairment. For example, the present formulations provide a mean Cmax from about 0.4 (ng/mL)/mg to about 0.6 (ng/mL)/mg, e.g., for subjects with uremic pruritus or renal impairment or from about 0.2 (ng/mL)/mg to about 0.3 (ng/mL)/mg, e.g., for subjects without any renal impairment.

In some embodiments, the dosing frequency and dose amount per administration are selected to provide a mean $C_{min}$ of from about 1 ng/mL to about 20 ng/mL (e.g., about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, or any other value or range of values therein). In certain embodiments, the dosing frequency and dose amount per administration are selected to provide a mean $C_{min}$ of from about 2 ng/mL to about 15 ng/mL. In other embodiments, the dosing frequency and dose amount per administration are selected to provide a mean $C_{min}$ of from about 5 ng/mL to about 10 ng/mL, 10 ng/mL to about 20 ng/mL, 20 ng/mL to about 30 ng/mL, 30 ng/mL to about 40 ng/mL, 40 ng/mL to about 50 ng/mL or 50 ng/mL to about 60 ng/mL.

In one embodiment, the dosing frequency and dose amount per administration are selected to provide a mean $C_{min}$ of from about 2 ng/mL to about 45 ng/mL, e.g., for subjects with uremic pruritus or renal impairment and optionally a pre AM dose or from about 0.5 ng/mL to about 25 ng/mL for subjects without any renal impairment and optionally a pre AM dose. In another embodiment, the dosing frequency and dose amount per administration are selected to provide a mean $C_{min}$ of from about 5 ng/mL to about 60 ng/mL, e.g., for subjects with uremic pruritus or renal impairment and optionally a pre PM dose or from about 2 ng/mL to about 20 ng/mL for subjects without any renal impairment and optionally a pre PM dose.

In certain embodiments, the dosing frequency and dose amount of the controlled release formulation provides a nalbuphine $AUC_{(0-\infty)}$ of from about 30 ng·hr/mL to about 950 ng·hr/mL, for example about 30, about 31, about 32, about 33, about 34, about 35, about 36, about 37, about 38, about 39, about 40, about 45, about 50, about 55, about 60, about 65, 70, 75 about 80, 85, about 90, about 95, about 100, about 105, about 110, about 115, about 120, about 125, about 130, about 135, about 140, about 145, about 150, about 155, about 160, 165, about 170, about 175, about 180, about 185, about 190, about 195, about 200, about 205, about 210, about 215, about 220, about 225, about to 30, about 235, about 240, about 245, about 250 about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 35, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 525, about 530, about 535, about 540, about 545, about 550, about 555, about 560, about 565, about 570, 575, about 580, 585, about 590, about 595, about 600, about 605, about 610, about 615, about 620, about 625, about 630, about 635, about 640 about 645, about 650, about 655, about 670, about 675, about 680, about 685, about 690, about 695, about 700, about 705, about 710, about 715, about 720, about 725, about 730, about 735, about 740, about 745, about 750, about 755, about 760, about 765, about 770, about 775, about 780, about 785, about 790, about 795, about 800, about 805, about 810, about 815, about 820, about 825, about 830, about 835, about 840, about 845, about 850, about 855, about 860, but 865, about 870, about 875, about 880, about 885, about 890, about 895, about 900, about 905, about 910, about 915, about 920, about 925, about 930, about 935, about 940, about 945, about 950 ng·hr/mL, or any other value or range of values therein.

In one embodiment, the dosing frequency and dose amount of the controlled release formulation provides a nalbuphine $AUC_{(0-\infty)}$ of from about 37 ng·hr/mL to about 910 ng·hr/mL. In another embodiment, the controlled release formulation provides a nalbuphine $AUC_{(0-\infty)}$ of from about 200 ng·hr/mL to about 500 ng·hr/mL. In another embodiment, the controlled release formulation provides a nalbuphine $AUC_{(0-\infty)}$ of from about 70 ng·hr/mL to about 210 ng·hr/mL. In yet another embodiment, the controlled release formulation provides a nalbuphine $AUC_{(0-\infty)}$ of from about 50 ng·hr/mL to about 800 ng·hr/mL. In still another embodiment, the controlled release formulation provides a nalbuphine $AUC_{(0-\infty)}$ of from about 60 ng·hr/mL to about 720 ng·hr/mL. In still another embodiment, the controlled release formulation provides a nalbuphine $AUC_{(0-\infty)}$ of from about 60 ng·hr/mL to about 80 ng·hr/mL.

In some embodiments, the dosing frequency and dose amount of the controlled release formulation provides a nalbuphine $AUC_{(0-\infty)}$ of from about 142 ng·hr/mL to about 2640 ng·hr/mL, e.g., for subjects with uremic pruritus or renal impairment or from about 49 ng·hr/mL to about 600 ng·hr/mL, e.g., for subjects without any renal impairment.

In other embodiments, the present formulations provide a nalbuphine $AUC_{(0-inf)}$ from about 1.392 (ng*hr/ml)/mg to about 3.43 (ng*hr/ml)/mg (e.g., about 1.4 (ng*hr/ml), about 1.5 (ng*hr/ml), about 1.6 (ng*hr/ml), about 1.7 (ng*hr/ml), about 1.8 (ng*hr/ml), about 1.9 (ng*hr/ml), about 2.0 (ng*hr/ml), about 2.1 (ng*hr/ml), about 2.2 (ng*hr/ml), about 2.3 (ng*hr/ml), about 2.4 (ng*hr/ml), about 2.5 (ng*hr/ml), about 2.6 (ng*hr/ml), about 2.7 (ng*hr/ml), about 2.8 (ng*hr/ml), about 2.9 (ng*hr/ml), about 3.0 (ng*hr/ml), about 3.1 (ng*hr/ml), about 3.2 (ng*hr/ml), about 3.3 (ng*hr/ml), about 3.4 (ng*hr/ml), or any other value or range of values therein).

In some embodiments, the present formulations provide a nalbuphine $AUC_{(0-inf)}$ from about 20 (ng*hr/ml)/mg to about 500 (ng*hr/ml)/mg. In some other embodiments, the present formulations provide a nalbuphine $AUC_{(0-inf)}$ from about 30 (ng*hr/ml)/mg to about 450 (ng*hr/ml)/mg. In yet some other embodiments, the present formulations provide a nalbuphine $AUC_{(0-inf)}$ from about 30 (ng*hr/ml)/mg to about 150 (ng*hr/ml)/mg.

In some other embodiments, the dosing frequency and dose amount of the controlled release formulation provides a nalbuphine $AUC_{tau}$ of from about 40 ng·hr/mL to about 800 ng·hr/mL (50 ng·hr/mL, 60 ng·hr/mL, 70 ng·hr/mL, 80 ng·hr/mL, 90 ng·hr/mL, 100 ng·hr/mL, 120 ng·hr/mL, 140 ng·hr/mL, 160 ng·hr/mL, 180 ng·hr/mL, 200 ng·hr/mL, 300 ng·hr/mL, 400 ng·hr/mL, 500 ng·hr/mL, 600 ng·hr/mL, 700 ng·hr/mL, 750 ng·hr/mL, or any other value or range of values therein), e.g., for subjects with uremic pruritus or renal impairment or from about 30 ng·hr/mL to about 360 ng·hr/mL (40 ng·hr/mL, 50 ng·hr/mL, 60 ng·hr/mL, 70 ng·hr/mL, 80 ng·hr/mL, 90 ng·hr/mL, 100 ng·hr/mL, 120 ng·hr/mL, 140 ng·hr/mL, 160 ng·hr/mL, 180 ng·hr/mL, 200 ng·hr/mL, 220 ng·hr/mL, 240 ng·hr/mL, 260 ng·hr/mL, 280 ng·hr/mL, 300 ng·hr/mL, 320 ng·hr/mL, 360 ng·hr/mL or any other value or range of values therein), e.g., for subjects without any renal impairment.

In yet some other embodiments, the dosing frequency and dose amount of the controlled release formulation provides a mean $C_{max}$ of about 1.5 ng/mL and $AUC_{(0-inf)}$ of about 20 hr·ng/mL at 30 mg BID, e.g., for subjects with uremic pruritus or renal impairment. In yet some other embodiments, the dosing frequency and dose amount of the controlled release formulation provides a mean $C_{max}$ of about 120 ng/mL and $AUC_{(0-inf)}$ of about 2000 hr·ng/mL at 120 mg BID, e.g., for subjects with uremic pruritus or renal impairment. In yet some other embodiments, the dosing frequency and dose amount of the controlled release formulation provides a mean $C_{max}$ of about 195 ng/mL and $AUC_{(0-inf)}$ of about 4100 hr·ng/mL at 180 mg BID, e.g., for subjects with uremic pruritus or renal impairment. In yet some other embodiments, the dosing frequency and dose amount of the controlled release formulation provides a mean $C_{max}$ of about 60 ng/mL and $AUC_{(0-inf)}$ of about 1600 hr·ng/mL at 240 mg BID, e.g., for subjects with uremic pruritus or renal impairment.

In some embodiments, the dosing frequency and dose amount of the controlled release formulation provides a mean $C_{max}$ of about 1.5 ng/mL and $AUC_{(0-inf)}$ of about 20 hr·ng/mL at 30 mg BID, e.g., for subjects without any renal impairment. In some other embodiments, the dosing frequency and dose amount of the controlled release formulation provides a mean $C_{max}$ of about 22 ng/mL and $AUC_{(0-inf)}$ of about 300 hr·ng/mL at 60 mg BID, e.g., for subjects without any renal impairment. In some embodiments, the dosing frequency and dose amount of the controlled release formulation provides a mean $C_{max}$ of about 60 ng/mL and AUC$_{(0-inf)}$ of about 700 hr·ng/mL at 180 mg BID, e.g., for subjects without any renal impairment.

In certain embodiments, the present methods can further comprise administering a rescue dose comprising nalbuphine to provide breakthrough relief of pruritus. The rescue dose can comprise nalbuphine in an amount of from about 1 mg to about 60 mg (e.g., about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, or any other value or range of values therein). In some embodiments, the rescue dose comprises from about 3 mg to about 30 mg of nalbuphine. In other embodiments, the rescue dose comprises from about 3 mg to about 45 mg of nalbuphine. The rescue dose can be administered parenterally, orally in an immediate release formulation, or as a buccal, sublingual, intranasal, or rectal dosage form. In some embodiments, the rescue dose is a tablet, capsule, a solution, a lozenge, or a suppository. In other embodiments, the rescue dose can be administered via a bilayer tablet which includes a rescue nalbuphine dose in an immediate release layer, and the tablet further comprises a nalbuphine dose in an extended release layer.

In some embodiments, the present methods employ a twice daily dosage regimen, and the first daily dose is less than the second daily dose. For example, in some embodiments, the second daily dose is from about 5 mg to about 180 mg greater than the first daily dose (e.g., about 5 mg greater, about 10 mg greater, about 15 mg greater, about 20 mg greater, about 25 mg greater, about 30 mg greater, about 35 mg greater, about 40 mg greater, about 45 mg greater, about 50 mg greater, about 55 mg greater, about 60 mg greater, about 65 mg greater, about 70 mg greater, about 75 mg greater, about 80 mg greater, about 85 mg greater, about 90 mg greater, about 95 mg greater, about 100 mg greater, about 105 mg greater, about 110 mg greater, about 115 mg greater, about 120 mg greater, about 125 mg greater, about 130 mg greater, about 135 mg greater, about 140 mg greater, about 145 mg greater, about 150 mg greater, about 155 mg greater, about 160 mg greater, about 165 mg greater, about 170 mg greater, about 175 mg greater, about 180 mg greater, or any other value or range of values therein).

In some embodiments, the second daily dose of nalbuphine can be selected as described above, and then titrated upward until the patient experiences satisfactory relief from the pruritic condition. Titrating the dose can include administering a baseline second daily dose, then after a period of observation at the baseline second daily dose value to determine the efficacy and/or side effect severity, of the baseline second daily dose, increasing the second daily dose if the subject does not experience adequate symptom relief. The period of observation at the baseline second daily dose before increasing the second daily dose can be from about 1 day to about 21 days (e.g., about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days). The second daily dose can be titrated in increments ranging from about 5 mg to about 180 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein). The second daily dose can be titrated in one or more steps. The amount a dosage is stepped, where there are multiple titration steps, can be the same, or can be different.

In some embodiments, the present methods employ a twice daily dosage regimen, and the first daily dose is greater than the second daily dose. For example, in some embodiments, the first daily dose is from about 5 mg to about 180 mg greater than the second daily dose (e.g., about 5 mg greater, about 10 mg greater, about 15 mg greater, about 20 mg greater, about 25 mg greater, about 30 mg greater, about 35 mg greater, about 40 mg greater, about 45 mg greater, about 50 mg greater, about 55 mg greater, about 60 mg greater, about 65 mg greater, about 70 mg greater, about 75 mg greater, about 80 mg greater, about 85 mg greater, about 90 mg greater, about 95 mg greater, about 100 mg greater, about 105 mg greater, about 110 mg greater, about 115 mg greater, about 120 mg greater, about 125 mg greater, about 130 mg greater, about 135 mg greater, about 140 mg greater, about 145 mg greater, about 150 mg greater, about 155 mg greater, about 160 mg greater, about 165 mg greater, about 170 mg greater, about 175 mg greater, about 180 mg greater, or any other value or range of values therein).

In some embodiments, the first daily dose of nalbuphine can be selected as described above, and then titrated upward until the patient experiences satisfactory relief from the pruritic condition. Titrating the dose can include administering a baseline first daily dose, then after a period of observation at the baseline first daily dose value to determine the efficacy of the baseline first daily dose and/or side effect severity, increasing the first daily dose if the subject does not experience adequate symptom relief. The period of observation at the baseline first daily dose before increasing the first daily dose can be from about 1 day to about 21 days (e.g., about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days). The first daily dose may be from about 5 mg to about 180 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein).

The titration dose can be in increments ranging from about 5 mg to about 180 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein). The first daily dose can be titrated in one or more steps. The amount a dosage is stepped, where there are multiple titration steps, can be the same, or can be different.

Accordingly, the total daily dose in a once daily dosing regimen with a titration dose, including baseline dose and one or more titration doses, may be from about 5 mg to about 180 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein).

In one embodiment, the initial dose is about 15 mg to about 30 mg once a day for a day or two, then about 30 mg twice a day for 2 to 3 days and then increase to about 60 mg or 120 mg twice a day, e.g., for subjects with uremic pruritus or renal impairment or about 90 mg or 180 mg twice a day, e.g., for subjects without renal impairment.

In one embodiment, the present methods include treating pruritus in a human patient, comprising (a) orally administering to a human patient suffering from pruritus an initial dosing regimen of nalbuphine in a controlled release formulation containing about 15 mg, 30 mg or 60 mg nalbuphine on a once a day or twice-a-day basis; (b) determining the effectiveness of the dosing regimen of nalbuphine in treating the patient's pruritus after at least about 1, 2 or 3 days of treatment; and (c) adjusting the dose and/or dosing interval of the oral controlled release nalbuphine formulation based on the information obtained in step (b) in order to provide improved efficacy of treatment of said patient's pruritus.

In other embodiments, the initial dosing is about 15 mg, 30 mg, or 60 mg once a day or twice a day and an effective dosing is obtained via titration, e.g., based on a pre-determined schedule, e.g., about 15 mg, 30 mg or 60 mg increment after about 2 or 3 days or based on a schedule designed by the physician treating the patient.

In some other embodiments, the maximum daily dose is about 75 mg, 150 mg, 180 mg, or 240 mg once a day, or 240 mg, 360 mg, 480 mg, 600 mg, or 720 mg twice a day. In one embodiment, the maximum daily dose is about 240 mg once a day or 480 mg twice a day, e.g., for subjects with or without renal impairment.

In some embodiments, the effectiveness of a dosage regimen can be determined by evaluation via a Pruritis Visual Analog Scale (VAS) test. In one embodiment, the effectiveness of a dosage regimen can be determined by evaluation via a Numerical Rating Scale (NRS). In yet some other embodiments, the effectiveness of a dosage regimen can be determined by evaluation via a Numerical Rating Scale (NRS) in association with Medical Outcomes Study (MOS), Itch MOS Sleep scale, Hospital Anxiety and Depression Scale (HADS), Patient Assessed Disease Severity Scale, or Skindex-10 or a combination thereof. In still another embodiment, the effectiveness of a dosage regimen can be determined by evaluation via a NRS independently or in association with Patient Global Assessment (PGA) via ItchApp, vPGA, Dermatology Life Quality Index (DLQI), Patient Benefit Index (PBI), MOS Sleep Scale, or HADS or a combination thereof. In still yet another embodiment, the effectiveness of a dosage regimen can be determined by evaluation via a NRS independently or in association with Prurigo Activity Score (PAS), Nocturnal scratching using actigraphy, nerve fiber density and MOR/KOR density.

In other embodiments, determining the effectiveness of the dose of nalbuphine can include evaluation of the patient's pruritus symptoms using an instrument selected from the group consisting of Pruritis Visual Analog Scale (VAS) test, Brief Itching Inventory, Skindex-10, Itch MOS of sleep, Beck Depression Index, and Patient Categorization of Pruritus Disease Severity.

In some embodiments, a subject, e.g., a human or animal patient can be treated initially with a twice-daily dosing regimen, and then after titrating either the first daily dose, the second daily dose, or both to arrive at a total daily dose effective to treat the patient's pruritus symptoms, the dosage regimen can be changed to a once-daily dosage. Each dose of the twice daily dosage can then be further titrated as described hereinabove to provide a therapeutically effective once daily dosage of nalbuphine. Thus, in some embodiments, the dosage regimen is a twice-daily dose, and each of the first and second doses can be titrated to achieve maximum therapeutic effect and/or minimal side effect severity. Accordingly, in some embodiments each of the first and second doses in a twice-daily dosage regimen may be from about 5 mg to about 240 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 190 mg, about 200 mg, about 210 mg, about 220 mg, about 230 mg, about 240 mg or any other value or range of values therein).

In some embodiments, each of the first and second daily doses in a twice daily dosage regimen may be independently titrated in an amount of from about 5 mg to about 240 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 190 mg, about 200 mg, about 210 mg, about 220 mg, about 230 mg, about 240 mg or any other value or range of values therein). The first and second doses in a twice-daily dosage regimen may be independently titrated in one or more steps. The amount a dosage is stepped, where there are multiple titration steps, can be the same, or can be different.

Accordingly, the total daily dose in a twice daily dosing regimen, including baseline dose for each administration and one or more titration doses for each administration independently, may be from about 5 mg a day to about 480 mg a day (e.g., about 15 mg a day, about 20 mg a day, about 25 mg a day, about 30 mg a day, about 35 mg a day, about 40 mg a day, about 45 mg a day, about 50 mg a day, about 55 mg a day, about 60 mg a day, about 65 mg a day, about 70 mg a day, about 75 mg a day, about 80 mg a day, about 85 mg a day, about 90 mg a day, about 95 mg a day, about 100 mg a day, about 105 mg a day, about 110 mg a day, about 115 mg a day, about 120 mg a day, about 125 mg a day, about 130 mg a day, about 135 mg a day, about 140 mg a day, about 145 mg a day, about 150 mg a day, about 155 mg a day, about 160 mg a day, about 165 mg a day, about 170 mg a day, about 175 mg a day, about 180 mg a day, about 185 mg a day, about 190 mg a day, about 195 mg a day, about 200 mg a day, about 205 mg a day, about 210 mg a day, about 215 mg a day, about 220 mg a day, about 225 mg a day, about 230 mg a day, about 235 mg a day, about 240 mg a day, about 245 mg a day, about 250 mg a day, about 255 mg a day, about 260 mg a day, about 265 mg a day, about 270 mg a day, about 275 mg a day, about 280 mg a day, about 285 mg a day, about 290 mg a day, about 295 mg a day, about 300 mg a day, about 305 mg a day, about 310 mg a day, about 315 mg a day, about 320 mg a day, about 325 mg a day, about 330 mg a day, about 335 mg a day, about 340 mg a day, about 345 mg a day, about 350 mg a day, about 355 mg a day, about 360 mg a day, about 390 mg, about 420 mg, about 450 mg, about 480 mg or any other value or range of values therein).

In some embodiments, the present methods employ a thrice daily dosage regimen, and the first daily dose is less than the second and third daily doses. For example, in some embodiments, the second and third daily doses may each independently be from about 5 mg to about 240 mg greater than the first daily dose (e.g., about 5 mg greater, about 10 mg greater, about 15 mg greater, about 20 mg greater, about 25 mg greater, about 30 mg greater, about 35 mg greater, about 40 mg greater, about 45 mg greater, about 50 mg greater, about 55 mg greater, about 60 mg greater, about 65 mg greater, about 70 mg greater, about 75 mg greater, about 80 mg greater, about 85 mg greater, about 90 mg greater, about 95 mg greater, about 100 mg greater, about 105 mg greater, about 110 mg greater, about 115 mg greater, about 120 mg greater, about 125 mg greater, about 130 mg greater, about 135 mg greater, about 140 mg greater, about 145 mg greater, about 150 mg greater, about 155 mg greater, about 160 mg greater, about 165 mg greater, about 170 mg greater, about 175 mg greater, about 180 mg greater, 190 mg, 200 mg, 210 mg, 220 mg, 230 mg, 240 mg or any other value or range of values therein).

In some embodiments, each of the first, second and third doses in a thrice-daily dosing regimen of nalbuphine can be selected as described above, and then titrated upward until the patient experiences satisfactory relief from the pruritic condition. Titrating the dose can include administering a baseline dose, then after a period of observation at the baseline dose value to determine the efficacy and/or side effect severity, of the baseline dose, increasing the dose if the subject does not experience adequate symptom relief. The period of observation at the baseline for any of the first, second and third doses independently can be from about 1 day to about 21 days (e.g., about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days). The dose (e.g., any one of three doses in a thrice daily dosing regimen) can be titrated in increments ranging from about 5 mg to about 180 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, or any other value or range of values therein). The second daily dose can be titrated in one or more steps. The amount a dosage is stepped, where there are multiple titration steps, can be the same, or can be different.

In other embodiments, the present methods employ a thrice daily dosage regimen, and the first daily dose is greater than the second and third daily doses. For example, in some embodiments, the first daily dose is from about 5 mg to about 240 mg greater than the second and third daily doses (e.g., about 5 mg greater, about 10 mg greater, about 15 mg greater, about 20 mg greater, about 25 mg greater, about 30 mg greater, about 35 mg greater, about 40 mg greater, about 45 mg greater, about 50 mg greater, about 55 mg greater, about 60 mg greater, about 65 mg greater, about 70 mg greater, about 75 mg greater, about 80 mg greater, about 85 mg greater, about 90 mg greater, about 95 mg greater, about 100 mg greater, about 105 mg greater, about 110 mg greater, about 115 mg greater, about 120 mg greater, about 125 mg greater, about 130 mg greater, about 135 mg greater, about 140 mg greater, about 145 mg greater, about 150 mg greater, about 155 mg greater, about 160 mg greater, about 165 mg greater, about 170 mg greater, about 175 mg greater, about 180 mg greater, about 190 mg greater, about 200 mg greater, about 210 mg greater, about 220 mg greater, about 230 mg greater, about 240 mg greater, or any other value or range of values therein).

In some embodiments, the each of the first, second and third doses in a thrice-daily dosing regimen can be selected as described above, and then titrated upward until the patient experiences satisfactory relief from the pruritic condition. Titrating the dose can include administering a baseline dose, then after a period of observation at the baseline dose value to determine the efficacy of the baseline dose and/or side effect severity, increasing the dose if the subject does not experience adequate symptom relief. The baseline dose may be from about 5 mg to about 240 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 190 mg, about 200 mg, about 210 mg, about 220 mg, about 230 mg, about 240 mg, or any other value or range of values therein).

The titration dose can be in increments ranging from about 5 mg to about 240 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 190 mg, about 200 mg, about 210 mg, about 220 mg, about 230 mg, about 240 mg, or any other value or range of values therein). Each of the first, second and third doses can be titrated in one or more steps. The amount a dosage is stepped, where there are multiple titration steps, can be the same, or can be different. Accordingly, the total daily dose in a thrice daily dosing regimen with a titration dose, including baseline doses and one or more titration doses, may be from about 5 mg to about 480 mg (e.g., about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 210 mg, about 240 mg, about 270 mg, about 300 mg, about 330 mg, about 360 mg, about 390 mg, about 420 mg, about 450 mg, about 480 mg, or any other value or range of values therein).

Accordingly, the total daily dose in a thrice daily dosing regimen, including baseline dose for each administration and one or more titration doses for each administration independently, may be from about 5 mg a day to about 480 mg a day (e.g., about 15 mg a day, about 20 mg a day, about 25 mg a day, about 30 mg a day, about 35 mg a day, about 40 mg a day, about 45 mg a day, about 50 mg a day, about 55 mg a day, about 60 mg a day, about 65 mg a day, about 70 mg a day, about 75 mg a day, about 80 mg a day, about 85 mg a day, about 90 mg a day, about 95 mg a day, about 100 mg a day, about 105 mg a day, about 110 mg a day, about 115 mg a day, about 120 mg a day, about 125 mg a day, about 130 mg a day, about 135 mg a day, about 140 mg a day, about 145 mg a day, about 150 mg a day, about 155 mg a day, about 160 mg a day, about 165 mg a day, about 170 mg a day, about 175 mg a day, about 180 mg a day, about 185 mg a day, about 190 mg a day, about 195 mg a day, about 200 mg a day, about 205 mg a day, about 210 mg a day, about 215 mg a day, about 220 mg a day, about 225 mg a day, about 230 mg a day, about 235 mg a day, about 240 mg a day, about 245 mg a day, about 250 mg a day, about 255 mg a day, about 260 mg a day, about 265 mg a day, about 270 mg a day, about 275 mg a day, about 280 mg a day, about 285 mg a day, about 290 mg a day, about 295 mg a day, about 300 mg a day, about 305 mg a day, about 310 mg a day, about 315 mg a day, about 320 mg a day, about 325 mg a day, about 330 mg a day, about 335 mg a day, about 340 mg a day, about 345 mg a day, about 350 mg a day, about 355 mg a day, about 360 mg a day, about 390 mg a day, about 420 mg a day, about 450 mg a day, about 480 mg a day, or any other value or range of values therein,).

In some embodiments, a subject, e.g., a human or animal patient can be treated initially with a thrice-daily dosing regimen, and then after titrating either the first daily dose, the second daily dose, and/or the third daily to arrive at a total daily dose effective to treat the patient's pruritus symptoms, the dosage regimen can be changed to either a twice-daily dosage or a once-daily dosage. Each dose of the thrice-daily dosage can be further titrated as described hereinabove to arrive at a therapeutically effective once daily dosage of nalbuphine.

In still other embodiment, the second dose in a thrice-daily dosing regimen may be greater than the first and third doses. In still other embodiments, the third daily dose may be greater than each of the first and second doses. Furthermore, as described above, each of the first, second and third doses in a thrice-daily regimen may be titrated independently of the other two doses, to arrive at a therapeutically efficacious dosing regimen.

In some embodiments, the single daily dosage can be administered in the evening or before bedtime. In other embodiments, the single daily dosage can be administered in the morning. In some embodiments, the single daily dose can be administered around midday (e.g., from about 11 am to about 1 pm). In twice-daily dosing regimens, the two doses may be administered in the morning and evening. In a thrice daily dosing regimen, the three doses may be administered with one dose given in the morning, one dose given at midday and one dose given in the evening.

In some embodiments, the present methods include treating pruritus in a subject, e.g., a human or animal patient, comprising administering to a subject, e.g., a human or animal patient suffering from pruritus an effective amount of a medication consisting of a pharmaceutical compound which is a μ-opioid receptor antagonist and a pharmaceutical compound which is a κ-opioid receptor agonist, or pharmaceutically acceptable salts or esters thereof. In certain embodiments, the pharmaceutical compound which is a μ-opioid receptor antagonist and the pharmaceutical compound which is a κ-opioid receptor agonist are the same. In some embodiments, the compound is nalbuphine or a pharmaceutically acceptable salt or ester thereof.

In certain embodiments, the anti-pruritic agent is nalbuphine, and the metabolites include glucuronides (most likely on the phenol and cyclohexane rings), two hydroxylated nalbuphine metabolites (on the cyclobutane ring) and three ketones (hydroxylation of the cyclobutane ring, followed by oxidation to a carbonyl). In some embodiments, the nalbuphine metabolites include nornalbuphine, 6-ketonalbuphine and nalbuphine 3-glucuronide. In some other embodiments, the nalbuphine metabolites include triple hydroxylated nalbuphine, mono-hydroxylated nalbuphine, or mono-glucuronidated nalbuphine or a combination thereof. In certain embodiments, the one or more metabolites of the anti-pruritus agent do not have detectable anti-pruritus activity. In other embodiments, one or more of the metabolites of the anti-pruritus agent exhibit anti-pruritus activity.

In embodiments wherein one or more metabolites of the anti-pruritus agent exhibit anti-pruritus activity, the dosing regimen of the anti-pruritus agent may be adjusted and/or titrated as described hereinabove depending on the clearance rate of the one or more metabolites exhibiting anti-pruritic activity. Such dosage adjustment and/or titration of the dosage of the anti-pruritic agent can be performed to prevent accumulation of either the anti-pruritic agent and/or one or more metabolites, which can also exhibit anti-pruritic activity, to avoid toxicity effects in a patient treated with the present anti-pruritic agent.

In some embodiments, the anti-pruritus agent is completely metabolized (e.g., about 100% metabolized). In other embodiments, the anti-pruritus agent is not completely metabolized (e.g., less than about 100% metabolized). For example, in some embodiments, the anti-pruritus agent is about 100% metabolized, about 95% metabolized, about 90% metabolized, about 85% metabolized, about 80% metabolized, about 75% metabolized, about 70% metabolized, about 65% metabolized, about 60% metabolized, about 55% metabolized, about 50% metabolized, about 45% metabolized, about 40% metabolized, about 35% metabolized, about 25% metabolized, about 20% metabolized, about 15% metabolized, about 10% metabolized, about 5% metabolized, about 1% metabolized, or about 0% metabolized. In certain embodiments, the amount of dialyzable anti-pruritus agent can be measured or monitored by the level of accumulation, e.g., blood plasma level of the anti-pruritus agent or one or more of its metabolites.

In some embodiments, the present methods can further comprise monitoring the plasma concentration of either an anti-pruritic agent, or one or more metabolites thereof. Such monitoring can be performed via measurement of the concentration of the anti-pruritic agent, or one or more metabolites thereof, in the blood of a patient via routine blood testing. Such testing can be conducted at suitable intervals to determine the peak blood plasma concentration of the anti-pruritic agent, or one or more metabolites thereof. Titration of dosage as described hereinabove can also be conducted via blood testing (in addition to qualitative measures described hereinabove for determining therapeutic levels of pruritus relief) to maintain safe levels of the anti-pruritic agent, or one or more metabolites thereof, in the present methods. Once a clearance rate of the anti-pruritic agent, or one or more metabolites thereof is established, an appropriate dosing regimen can be selected to provide target $C_{max}$ and $AUC_{(0-\infty)}$ ranges as described herein above.

According to some embodiments of the present invention, administering of nalbuphine or a pharmaceutically acceptable salt or ester thereof according to the methods of the present invention provides statistically significant therapeutic effect. In one embodiment, the statistically significant therapeutic effect is determined based on one or more standards or criteria provided by one or more regulatory agencies in the United States, e.g., FDA or other countries. In another embodiments, the statistically significant therapeutic effect is determined based on results obtained from regulatory agency approved clinical trial set up and/or procedure.

In some embodiments, the statistically significant therapeutic effect is determined based on a patient population of at least 100, 200, 300, 400, 500, 600, 700, 800, 900, 1000 or 2000. In some embodiments, the statistically significant therapeutic effect is determined based on data obtained from randomized and double blinded clinical trial set up. In some embodiments, the statistically significant therapeutic effect is determined based on data with a p value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase III clinical trial of the methods provided by the present invention, e.g., by FDA in the US.

In some embodiment, the statistically significant therapeutic effect is determined by a randomized double blind clinical trial of a patient population of at least 300 or 350; treated with nalbuphine or a pharmaceutically acceptable salt or ester thereof and optionally in combination with standard care. In some embodiment, the statistically significant therapeutic effect is determined by a randomized clinical trial of a patient population of at least 300 or 350 and using NRS as primary efficacy parameter and optionally in combination with any other commonly accepted criteria for pruritus assessment.

In general, statistical analysis can include any suitable method permitted by a regulatory agency, e.g., FDA in the US or Europe or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

The following non-limiting examples illustrate various aspects of the present invention.

EXAMPLES

Examples 1 to 3

Three sustained release delivery systems were prepared by dry blending xanthan gum, locust bean gum, calcium sulfate dihydrate, and mannitol in a high speed mixed/granulator for 3 minutes. While running choppers/impellers, water was sprayed to the dry blended mixture, and granulated for another 6 minutes. Then the granulation process was stopped and the mixer/granulation bowl was scraped. While running choppers/impellers, the granulation was mixed for one more minute. After the granulation was checked for consistency, while running choppers/impellers additional water was added to the granulation and granulated for additional 3.5 minutes. The granulation was then dried to LOD (loss on drying) of less than about 4% by weight. The granulation was then milled using screen #1521-0033. The relative quantities of the ingredients are listed in Table 1.

TABLE 1

| Sustained Release Delivery System Excipient | Example 1 % | Example 2 % | Example 3 % |
|---|---|---|---|
| Xanthan Gum, NF | 8.0 | 12.0 | 20.0 |
| Locust Bean Gum, FCC | 12.0 | 18.0 | 30.0 |
| Mannitol, USP | 70.0 | 60.0 | 40.0 |
| Calcium Sulfate Dihydrate, NF | 10.0 | 10.0 | 10.0 |
| Sterile Water for Injection, USP[1] | — | — | — |
| Total | 100.0 | 100.0 | 100.0 |

[1]Sterile Water for Injection, USP is removed during processing

Examples 4 to 7

A series of tablets containing different amounts of gum were prepared using the sustained release delivery system of Example 3. The quantities of ingredients per tablet are listed in Table 2.

TABLE 2

| Component | Ex. 4 Mg | Ex. 5 Mg | Ex. 6 mg | Ex. 7 mg |
|---|---|---|---|---|
| Nalbuphine HCl, USP | 60 | 60 | 60 | 60 |
| Sustained release delivery system | 60[1] | 120[1] | 180[1] | 90[1] |
| Magnesium stearate, NF | 0.5 | 1.8 | 1.2 | 0.75 |
| Total Weight | 120.5 | 181.8 | 241.2 | 150.75 |
| Active:Gum | 1:0.5 | 1:1 | 1:1.5 | 1:0.75 |
| Tooling Size | 0.2812" | 0.2812" | 0.3125" | 0.2812" |
| Hardness (Kp) | 1.2 | 8.8 | 8.9 | 7.2 |

[1]Sustained release system of Example 3

The tablets were prepared by mixing nalbuphine with the sustained release delivery system in a mixer. The magnesium stearate was passed through a #30 mesh screen sieve and then mixed with the dry blend containing nalbuphine and the sustained release delivery system. This lubricated blend was compressed using the tooling as specified in Table 2 to make tablets of the total weight indicated.

The tablets of Examples 4-7 were tested for in vitro % release rate according to USP Procedure Drug Release General Chapter <711> Dissolution, using apparatus USP Type III/250 mL. The test was performed at pH 6.8, 37° C./15 dpm (dips per minute) in 100 mM ammonium phosphate buffer. The results are shown in Table 3.

TABLE 3

| Dissolution Time (hours) | Example 4 pH 6.8 | Example 5 pH 6.8 | Example 6 pH 6.8 | Example 7 pH 6.8 |
|---|---|---|---|---|
| 0 | 0 | 0 | 0 | 0 |
| 1 | 29.3 | 23.8 | 19.5 | 25.0 |
| 2 | 41.8 | 35.1 | 29.4 | 35.9 |
| 4 | 59.2 | 51.7 | 45.0 | 53.0 |
| 6 | 72.9 | 65.6 | 56.4 | 67.1 |
| 8 | 84.2 | 77.8 | 65.3 | 79.6 |
| 12 | 98.1 | 92.9 | 81.0 | 93.9 |
| Remnant | 4.3 | 6.9 | 16.3 | 6.0 |
| % Recovery | 102.4 | 98.8 | 97.3 | 99.9 |

Examples 8 to 10

A series of tablets containing different amounts of gum and different sustained release delivery systems were prepared using the sustained release delivery systems of Examples 1 and 2. The quantities of ingredients per tablet are listed in Table 4.

TABLE 4

| Component | Ex. 8 mg | Ex. 9 Mg | Ex. 10 mg |
|---|---|---|---|
| Nalbuphine HCl, USP | 60 | 60 | 60 |
| Sustained release delivery system | 225[2] | 150[3] | 100[3] |
| Magnesium stearate | 1.43 | 1.1 | 0.8 |
| Total weight | 286.4 | 211.1 | 160.8 |
| Active:Gum | 1:0.75 | 1:0.75 | 1:0.5 |
| Tooling Size | 0.3125" | 0.3125" | 0.2812" |
| Hardness (Kp) | 20 | 17 | 20 |

[2]Sustained release delivery system of Example 1
[3]Sustained release delivery system of Example 2

The tablets were prepared by first mixing nalbuphine with the sustained release delivery system in a mixer for Example 8 and in a high shear granulator for Example 9 and 10. For Examples 9 and 10, the blend was then granulated with water until consistent granulation was achieved, followed by drying in a fluidized bed dryer for 30 minutes at 70° C. The dried granules were then passed through a Fitzmill at 2500 rpm using 1521-0050 screen. The magnesium stearate was passed through a #30 mesh screen sieve, and then mixed with the milled granules for Examples 9 and 10 and with the dry blend for Example 8 for 5 minutes. The lubricated blend was compressed using the tooling as specified in Table 4 to make tablets of the total weight indicated.

The tablets of Examples 8-10 were tested for in vitro % release rate according to USP Procedure Drug Release General Chapter <711> Dissolution, using apparatus USP Type III/250 mL. The test was performed in pH change, at 37° C./15 dpm. The pH change was as follows: pH 1.2 for the first hour, pH 4.5 for the second hour, and pH 6.8 after the second hour and through the duration of the test. The results are shown in Table 5.

TABLE 5

| Dissolution Time (hours) | Example 8 pH change | Example 9 pH change | Example 10 pH change |
|---|---|---|---|
| 0 | 0.0 | 0 | 0 |
| 1 | 19.4 | 18.8 | 22.5 |
| 2 | 36.4 | 39.7 | 45.3 |
| 4 | 59.0 | 66.3 | 73.2 |
| 6 | 72.5 | 82.6 | 89 |
| 8 | 79.4 | 89.8 | 95.9 |
| 12 | 82.1 | 92.3 | 100.1 |
| Remnant | 0.1 | 0.1 | 0.8 |
| % Recovery | 82.2 | 92.4 | 100.9 |

Examples 11 to 16

To determine the effect of the amount of gum in combination with microcrystalline cellulose (Emococel 90M), six batches of tablets were prepared using the sustained release delivery system of Example 3. The range of Active: Gum ratios used in Examples 11-16 varied between 1:0.25 and 1:0.5. Compositions of the tablets are shown in Table 6.

TABLE 6

| Ingredient | Ex. 11 mg/tab | Ex. 12 mg/tab | Ex. 13 mg/tab | Ex. 14 mg/tab | Ex. 15 mg/tab | Ex. 16 mg/tab |
|---|---|---|---|---|---|---|
| Sustained release delivery system | 30[4] | 60[4] | 60[4] | 30[4] | 60[4] | 60[4] |
| Nalbuphine HCl | 60 | 60 | 60 | 60 | 60 | 60 |
| Microcrystalline Cellulose | 30 | 30 | 60 | 60 | 120 | — |
| Magnesium stearate | 0.6 | 0.8 | 0.9 | 0.8 | 1.2 | 0.6 |
| Total Weight (mg) | 120.6 | 150.8 | 180.9 | 150.8 | 241.2 | 120.6 |
| Active:Gum | 1:0.25 | 1:0.5 | 1:0.5 | 1:0.25 | 1:0.5 | 1:0.5 |
| Tooling Size | 0.2500" | 0.2812" | 0.2812" | 0.2812" | 0.3125" | 0.2500" |
| Hardness (Kp) | 10.2 | 10 | 12 | 13 | 22 | 13.2 |

[4]Sustained release delivery system of Example 3

The tablets of Examples 11-15 were prepared by first sifting magnesium stearate through #30 mesh screen sieve. Then blend nalbuphine with the sustained release delivery system, and magnesium stearate in a blender for 5 minutes. The lubricated blend was compressed using the tooling as specified in Table 6 to make tablets of the total weight indicated.

The tablets of Example 16 were prepared by mixing nalbuphine in a high shear granulator with the sustained release delivery system. The blend was then granulated with water until consistent granulation was achieved. The granulation is then dried in a fluidized bed dryer for 40 minutes at 70° C. The dried granules were then passed through a Fitzmill at 2500 rpm using 1521-0050 screen. The magnesium stearate was passed through a 430 mesh screen sieve and then mixed with the milled granules for 5 minutes. The lubricated blend was compressed using the tooling as specified in Table 6 to make tablets of the total weight indicated.

The tablets of Examples 11-16 were tested for in vitro % release rate according to USP Procedure Drug Release General Chapter <711> Dissolution, using apparatus USP Type III/250 mL. The test was performed in pH change, at 37° C./15 dpm, as described above for Examples 8-10. The results are shown in Table 7.

TABLE 7

| Dissolution time (hours) | Ex. 11 pH change | Ex. 12 pH change | Ex. 13 pH change | Ex. 14 pH change | Ex. 15 pH change | Ex. 16 pH change |
|---|---|---|---|---|---|---|
| 0 | 0.0 | 0.0 | 0.0 | 0.0 | 0.0 | 0.0 |
| 1 | 93.2 | 59.4 | 94.5 | 93.4 | 92.1 | 17.1 |
| 2 | 94.4 | 73.0 | 96.0 | 94.8 | 93.4 | 39.7 |
| 4 | 94.5 | 84.5 | 96.0 | 94.8 | 93.5 | 64.4 |
| 6 | 94.5 | 87.4 | 96.0 | 94.8 | 93.5 | 74.6 |
| 8 | 94.5 | 88.7 | 96.0 | 94.8 | 93.5 | 81.5 |
| 12 | 94.5 | 90.2 | 96.0 | 94.8 | 93.5 | 93.1 |
| Remnant | 0.0 | 1.2 | 0.0 | 0.0 | 0.0 | 7.0 |
| % Recovery | 94.5 | 91.5 | 96.0 | 94.8 | 93.5 | 100.1 |

Examples 17 and 18

Two batches of bi-layer tablets were prepared using the sustained release delivery system of Example 2 (Examples 17 and 18). In the bi-layer tablets, the first layer of the tablets was formulated to provide relatively a slow sustained release; the second layer was formulated to provide relatively fast (immediate) release. The in vitro dissolution profiles of the bi-layer tablets were compared to the dissolution profile of single layer tablets that were formulated to provide a sustained release (Example 9). Compositions of the tablets are shown in Table 8.

TABLE 8

| Ingredient | Example 17 mg/tab | Example 18 mg/tab | Example 9 mg/tab |
|---|---|---|---|
| Extended release layer (ER) | | | |
| Sustained release delivery system | 112.5[5] | 112.9[5] | 150 |
| Nalbuphine HCI | 45 | 45 | 60 |
| Magnesium stearate | 0.8 | 0.8 | 1.1 |
| ER weight | 158.3 | 158.3 | 211.1 |
| Immediate release layer (IR) | | | |
| Sustained release delivery system | 6.05 | | N/A |
| Nalbuphine HCI | 15.0 | | N/A |
| Microcrystalline Cellulose, NF (Emcocel 90 M) | 35.7 | | N/A |
| Croscarmellose Sodium, NF (Primellose ®) | 3.0 | | N/A |
| Magnesium stearate, NF | 0.3 | | N/A |
| IR Weight | 60.0 | | N/A |
| Total Weight | 218.3 | 218.3 | 211.1 |
| Active:Gum | 1:0.6 | 1:0.6 | 1:0.75 |
| Tooling Size | 0.2812" | 0.2812" | 0.3125" |
| Hardness | N/A | N/A | 17 |

[5]Sustained release delivery system of Example 2

For the extended release layer, the nalbuphine was mixed with the sustained release delivery system in a high shear granulator for 3 minutes. The mixture was granulated with water until consistent granulation was achieved, then the wet mass was dried in a fluidized bed dryer for 20 minutes at 70° C. The dried granules were then passed through a Fitzmill at 2500 rpm using 1521-0050 screen. For the immediate release layer, the nalbuphine was blended with the sustained release delivery system, microcrystalline cellulose (Emcocel® 90M), and croscarmellose sodium, NF (Primellose®) in a V-Blender for 10 minutes. The magnesium stearate was passed through a #30 mesh screen sieve. The milled granules of the slow release layer was mixed with the sieved magnesium stearate in a V-blender for 5 minutes and the dry blend of the immediate release layer was mixed with the sieved magnesium stearate in a V-blender for 5 minutes, separately. This lubricated blend of the extended release layer and the immediate release layer were then compressed into bi-layer tablets using the tooling specified in Table 8, to make the tablets of the total weight indicated.

The tablets of Examples 17-18 were tested for in vitro % release rate according to USP Procedure Drug Release USP General Chapter <711> Dissolution, using apparatus USP Type III/250 mL. The test was performed in pH change as described above for Examples 8-10, at 37° C./15 dpm, as described above for Examples 8-10. The results are shown in Table 9. For purposes of comparing the dissolution profiles of the bi-layer tablets with a single-layer tablet, the dissolution data for Example 9 is also shown in Table 9.

TABLE 9

| Dissolution time (hours) | Ex. 17 pH change | Ex. 18 pH change | Ex. 9 pH change |
|---|---|---|---|
| 0 | 0 | 0.0 | 0 |
| 1 | 44.5 | 42.6 | 18.0 |
| 2 | 62.8 | 62.7 | 39.7 |
| 4 | 83.1 | 84.3 | 66.3 |
| 6 | 92.3 | 92.3 | 82.6 |
| 8 | 94.0 | 93.7 | 89.8 |
| 12 | 94.0 | 93.9 - | 92.3 |
| Remnant | 0.0 | 0 | 0.1 |
| % Recovery | 94.1 | 93.9 | 92.4 |

Examples 19 and 20

For a clinical study, one batch of bi-layer tablets and one batch of single layer tablets were prepared using the sustained release delivery system of Example 2. The first layer of the tablets was formulated to provide relatively a slow sustained release; the second layer was formulated to provide relatively fast (immediate release). Compositions of the tablets are shown in Table 10.

TABLE 10

| Component | Amount mg/tablet (%) | |
|---|---|---|
| Ingredient | Example 19(F-2) | Example 20(F-1) |
| Extended release player (ER) | | |
| Sustained Release Excipient (30%) | 112.5[6] | 150.0[6] |
| Nalbuphine HCI | 45.00 | 60.00 |
| Magnesium stearate, NF | 0.8 | 1.10 |
| Sterile Water for Injection, USP • | • | • |
| Mg/tablet weight (ER portion) | 158.3 | 211.1 |

TABLE 10-continued

| Component | Amount mg/tablet (%) | |
|---|---|---|
| Ingredient | Example 19(F-2) | Example 20(F-1) |
| Immediate release layer (IR) | | |
| Nalbuphine HCl | 15.0 | |
| Microcrystalline Cellulose, NF | 41.7 | |
| Croscarmellose Sodium, NF | 3.0 | |
| Magnesium stearate, NF | 0.3 | |
| Mg/tablet weight (IR portion) | 60.0 | |
| Total Weight (mg/tablet) | 218.3 | 211.1 |
| Type of tablet | Bi-layer(ER/IR) | Single layer (ER) |
| Active to Gum Ratio | 1:0.75 | 1:0.75 |
| Tooling Size | 0.3125 | 0.3125 |
| Hardness | ~11 Kp | ~11 Kp |

* Sterile Water for Injection, USP is removed during process
[6]Sustained release delivery system of Example 2

For the extended release layer of Example 19 and 20, the nalbuphine was mixed with the sustained release delivery system in a high shear granulator (6-liter Diosna-Pharma Mixer ⅙) for 5 minutes with the impeller speed at 300 rpm and the chopper off. After the mixer stopped, the bowl was scraped and sample was taken for LOD. While the impeller and the chopper are running at 300 rpm, the mixture was granulated with water for 2 minutes. After the mixer stopped, the bowl was scraped. While impeller speed is running at 500 rpm and the chopper speed at 300 rpm, the granulation was continued by mixing for an additional 1 minute. At the end of mixing the bowel was scraped. While the impeller and chopper were running at 300 rpm, additional of water (about 50.0 g) was added and granulated for 2 minutes in Example 19 and for 1 minute in Example 20. To achieve consistent granules, the granulation was mixed for additional 3 minutes in Example 19 and 1 minute in Example 20, while the impeller and chopper were running at 500 and 300 rpm, respectively. Then the wet mass was dried in a Uni-Glatt fluid bed dryer for 30 minutes at 70° C. The dried granules were then passed through a Fitzmill, knives forward, with the speed of 2200-2700 rpm using 1521-0033 screen. The magnesium stearate was passed through a #30 mesh screen sieve. The milled granules of the extended release layer for Example 19 and 20 were mixed separately with the sieved magnesium stearate in a V-blender with a 4-quart stainless steel shell for 5 minutes.

For Example 20, the lubricated blend of the extended release layer was compressed into single layer tablets with the Piccola tablet press using the tooling specified in Table 11, to make the tablets of the total weight indicated.

In the immediate release layer portion of Example 19, the nalbuphine was blended with the microcrystalline cellulose (Emcocel 90M) in a P-K Blend Master V-Blender for 5 minutes. To the mixture, croscarmellose sodium, NF (Primellose®) was added and mixed for 5 minutes. The magnesium stearate was passed through a #30 mesh screen sieve. The milled granules of the extended release layer portion of Example 19 was mixed with the sieved magnesium stearate in a V-blender with a 4-quart stainless steel shell for 5 minutes and the dry blend of the immediate release layer portion was mixed with the sieved magnesium stearate in a V-blender with a 4-quart stainless steel shell for 5 minutes, separately. This lubricated blend of the extended release layer portion and the immediate release layer portion were then compressed into bi-layer tablets with the Piccola tablet press using the tooling specified in Table 10, to make the tablets of the total weight indicated.

The tablets of Examples 19-20 were tested for in vitro % release rate according to USP Procedure Drug Release USP General Chapter <711> Dissolution, using apparatus USP Type III/250 mL. The test was performed in pH 6.8, at 37° C./15 dpm. The results are shown in Table 11.

TABLE 11

| Dissolution Time (h) | Example 19(F-2) | Example 20(F-1) |
|---|---|---|
| 0 | 0 | 0 |
| 1 | 47 | 26 |
| 3 | 69 | 51 |
| 4 | 77 | 61 |
| 6 | 88 | 76 |
| 8 | 95 | 86 |
| 12 | 99 | 96 |
| Remnant | 0 | 2 |
| Recovery | 99 | 98 |

These data demonstrate that the dissolution rate from the bi-layer (ER/IR) formulation (Example 19(F-2)) was about 21% and 16% faster than the rate from the single layer (ER) formulation (Example 20(F-1)) at 1 and 4 hours time point, respectively.

Clinical Study

A Phase I, open label, five treatment arm, single dose escalation study under fasting conditions was conducted and pharmacokinetic data were obtained with the following formulations: a) the sustained delivery system-nalbuphine 60 mg bi-layer tablet (IR/ER) (Example 19 (F-2)), b) the sustained delivery system-nalbuphine 60 mg single layer tablet (ER) (Example 20(F-1)), c) two tablets of the 60 mg single layer tablet (ER, 120 mg total dose), d) three tablets of the 60 mg single layer tablet (ER, 180 mg total dose) and e) a dose of nalbuphine immediate release 60 mg oral solution (control). Eleven healthy volunteers were initially enrolled with six subjects completing all five treatments. The pharmacokinetic data are summarized below both as arithmetic and geometric mean results. The mean blood level ("plasma") concentration of nalbuphine for each time point is shown in Table 16. A logarithmic graph of the mean nalbuphine plasma concentration versus time for each formulation is shown in FIG. 1.

TABLE 12

Pharmacokinetic Parameters
Arithmetic Mean Values

| Formulation | Cmax ng/mL | •Tmax (h) | AUC(0-t) (ng · h/mL) | AUC(0-∞) (ng · h/mL) |
|---|---|---|---|---|
| 60 mg (F-2) | 8.58 | 1.5 | 75.95 | 83.87 |
| 60 mg (F-1) | 7.17 | 3.5 | 78.73 | 90.70 |
| 120 mg (F-1) | 12.87 | 6.0 | 154.63 | 170.75 |
| 180 mg (F-1) | 15.59 | 8.0 | 200.63 | 213.22 |
| 60 mg oral solution (IR) | 13.75 | 1.0 | 61.85 | 68.50 |

•Median Tmax values reported

TABLE 13

Relative Bioavailability
(based on dose normalized arithmetic mean values)

| | Cmax ratio | AUC (0-t) ratio | AUC (0-∞) ratio |
|---|---|---|---|
| 60 mg (F-2)/ER | 0.62 | 1.23 | 1.22 |
| 60 mg (F-1)/ER | 0.52 | 1.27 | 1.32 |
| 120 mg (F-1)/ER | 0.47 | 1.25 | 1.25 |
| 180 mg (F-1)/ER | 0.38 | 1.08 | 1.04 |

TABLE 14

Pharmacokinetic Parameters
Geometric Mean Values

| Formulation | Cmax ng/mL | AUC(0-t) (ng · h/mL) | AUC(0-∞) (ng · h/mL) |
|---|---|---|---|
| 60 mg (F-2) | 7.58 | 68.72 | 77.85 |
| 60 mg (F-1) | 6.28 | 69.95 | 85.65 |
| 120 mg (F-1) | 12.24 | 140.61 | 158.62 |
| 180 mg (F-1) | 13.67 | 175.73 | 189.32 |
| 60 mg oral solution (IR) | 12.48 | 56.29 | 63.14 |

TABLE 15

Relative Bioavailability
(based on dose normalized arithmetic mean values)

| | Cmax ratio | AUC (0-t) ratio | AUC (0-∞) ratio |
|---|---|---|---|
| 60 mg (F-2)/ER | 0.62 | 1.22 | 1.23 |
| 60 mg (F-1)/ER | 0.50 | 1.24 | 1.36 |
| 120 mg (F-1)/ER | 0.49 | 1.25 | 1.26 |
| 180 mg (F-1)/ER | 0.37 | 1.04 | 1.00 |

TABLE 16

Nalbuphine Plasma Concentration
Concentration (ng/mL)

| Time Point (hrs) | 60 mg IR | 60 mg (F-1) | 60 mg (F-2) | 120 mg (F-1) | 180 mg (F1) |
|---|---|---|---|---|---|
| 0 | 0 | 0 | 0 | 0 | 0 |
| 0.25 | 10.57 | 1.83 | 0.79 | 1.01 | 1.00 |
| 0.5 | 14.81 | 4.69 | 1.71 | 2.94 | 3.55 |
| 1 | 13.53 | 7.57 | 3.33 | 6.51 | 7.87 |
| 1.5 | 11.20 | 7.42 | 3.63 | 8.81 | 10.59 |
| 2 | 9.77 | 6.89 | 5.88 | 9.41 | 11.40 |
| 3 | 6.58 | 6.18 | 4.96 | 9.04 | 11.90 |
| 4 | 4.65 | 5.36 | 4.77 | 8.20 | 10.71 |
| 6 | 3.29 | 5.31 | 6.18 | 10.45 | 14.01 |
| 8 | 1.76 | 4.00 | 4.76 | 8.55 | 10.59 |
| 12 | 1.67 | 2.83 | 3.32 | 6.77 | 9.20 |
| 16 | 1.01 | 1.87 | 2.24 | 4.27 | 5.14 |
| 20 | 0.76 | 1.13 | 1.51 | 2.96 | 3.27 |
| 24 | 0.68 | 0.84 | 1.11 | 2.02 | 2.46 |
| 36 | NT* | 0.57 | 0.54 | 0.94 | 0.98 |
| 48 | NT | NT | NT | NT | 0.75 |

*Not tested

In general, the F-1 (Example 20) and F-2 (Example 19) formulations had higher AUCs (0-t and 0-∞) and lower Cmax values (for both arithmetic and geometric mean values) compared to the immediate release oral solution. These differences were moderate for AUCs (0-t and 0-∞) and moderate to significant for Cmax and were based on dose-normalized comparisons of the F-1 and F-2 formulations with the immediate release oral solution. Minimal differences in AUCs (0-t and 0-∞) were seen between the F-1 and F-2 formulations at a comparative dose of 60 mg.

These data demonstrate that the oral bioavailability for the sustained release nalbuphine formulations was greater than that of the immediate release control formulation. Specifically, the oral availability of formulation F-2 was 23% greater than that of the immediate release oral solution, based on the geometric mean values for the area under the plasma concentration time curve. Similarly, the oral bioavailability of Formulation F-1 was 36% greater than that of the immediate release oral solution, based on the geometric mean values for the area under the plasma concentration time curve.

The $C_{max}$ values for the sustained release formulations were approximately 60% of the $C_{max}$ observed with the immediate release oral solution. These data suggest that the potential for adverse events (i.e., side effects) could be decreased with the sustained release formulation compared to immediate release formulations.

Median $T_{max}$ values reported were 1.0, 1.5 and 3.5 hours for the oral solution, F-2 and F-1 formulations, respectively. Longer $T_{max}$ values were observed for the 2 higher doses of the F-1 formulation (6.0 and 8.0 hours for the 120 and 180 mg doses, respectively).

Dose linearity was observed for all three doses of the F-1 formulation (60, 120 and 180 mg.

As shown in FIG. 1, the blood plasma concentration of nalbuphine for the extended release formulations increases quickly to one or more peaks shortly following administration, followed by a plateau region. The duration of the plateau period varies based on the dose strength and type of formulation, but is generally in the range from about 1.5 hours to about 10 hours. In contrast, the blood plasma level for the immediate release formulation quickly maximizes, followed by an immediate decrease in nalbuphine concentration from time point to time point. Following the plateau period, there is a decrease in the nalbuphine blood plasma concentration from one time point to the next.

Example 21

Nalbuphine 60 mg Extended Release Tablets

The 60 mg extended release nalbuphine tablets of Example 21 were prepared as follows: Nalbuphine HCl and TIMERx M30A were added to a high shear mixer and dry mixed at low speed. A granulating solution (water for injection or purified water) was then introduced to the mixer at low speed. The subsequent mixture was granulated at high speed and dried in a fluid bed processor. The dried granules were milled and sized via a conventional mill. The milled granulation was then transferred into a diffusion (tumble) mixer. Magnesium stearate was added to the diffusion mixer and blended. The final blend was compressed using a rotary tablet press. The resulting tablets were then coated with the non-functional coating using a conventional coating pan.

TABLE 17

60 mg Extended Release Nalbuphine
Tablet with Non-Functional Coating

| Ingredient | mg/tablet |
|---|---|
| Nalbuphine HCl | 60.0 |
| TIMERx M30A[1] | 150.0 |
| (Mannitol) | (90.0) |
| (Locust bean gum) | (27.0) |

TABLE 17-continued 60 mg Extended Release Nalbuphine
Tablet with Non-Functional Coating

| Ingredient | mg/tablet |
| --- | --- |
| (Xanthan Gum) | (18.0) |
| (Calcium sulfate dihydrate) | (15.0) |
| Magnesium stearate | 1.1 |
| Opadry II Purple | 6.3 |
| Water for injection or | QS |
| Purified water | |
| Total: | 217.4 |

[1] Sustained release excipient of Example 2

The formulation of Example 21 is identical to the tablet formulation of Examples 9 and 20, except with the addition of a non-functional coating.

Example 22

Nalbuphine 60 mg Extended Release Tablets

The 60 mg extended release nalbuphine tablets of Example 22 were prepared as follows: Nalbuphine HCl and TIMERx M30A were added to a high shear mixer and dry mixed at low speed. A granulating solution (water for injection or purified water) was then introduced to the mixer at low speed. The subsequent mixture was granulated at high speed and dried in a fluid bed processor. The dried granules were milled and sized via a conventional mill. The milled granulation was then transferred into a diffusion (tumble) mixer. Hydroxypropyl cellulose was added to the diffusion mixer and blended. Thereafter, magnesium stearate was added to the diffusion mixer and blended. The final blend was compressed using a rotary tablet press. The resulting tablets were then coated with the non-functional coating using a conventional coating pan.

TABLE 18

60 mg Extended Release Nalbuphine Tablet with Addition of
Hydroxypropyl Cellulose and Reduction of TimeRx Excipient

| Ingredient | mg/tablet |
| --- | --- |
| Nalbuphine HCl | 60.0 |
| TIMERx M30A[1] | 120.0 |
| (Mannitol) | (72.0) |
| (Locust bean gum) | (21.6) |
| (Xanthan Gum) | (14.4) |
| (Calcium sulfate dihydrate) | (12.0) |
| Hydroxypropylcellulose | 30.0 |
| Magnesium stearate | 1.6 |
| Water for injection or | QS |
| Purified water | |
| Total: | 211.6 |

[1] Sustained release excipient of Example 2

Examples 23-28

The nalbuphine tablets of Examples 23-28 were prepared as follows: Nalbuphine HCl, mannitol, xanthan gum, locust bean gum and calcium sulfate dihydrate were added to a high shear mixer and dried mix at low speed. A granulating solution (water for injection or purified water) was introduced into the mixer at low speed. The wet granulation was granulated at high speed and dried in a fluid bed processor. The dried granules were milled and sized using a conventional mill. The milled granulation was transferred into a diffusion (tumble) mixer. Hydroxypropylcellulose and, when applicable, fumaric acid (180 mg formulations only) were added to the diffusion mixer and blended. Thereafter, magnesium stearate was added to the diffusion mixer and blended. The final blend was compressed using a rotary tablet press.

TABLE 19

(Example 23)
30 mg Extended Release Nalbuphine Tablet

| Ingredient | mg/tablet |
| --- | --- |
| Nalbuphine HCl | 30.0 |
| Mannitol | 108.0 |
| Hydroxypropylcellulose | 35.0 |
| Locust bean gum | 32.4 |
| Xanthan gum | 21.6 |
| Calcium sulfate dehydrate | 18.0 |
| Magnesium stearate | 1.9 |
| Water for injection or | QS |
| Purified water | |
| Total: | 246.9 |

TABLE 20

(Example 24)
60 mg Extended Release Nalbuphine Tablet

| Ingredient | mg/tablet |
| --- | --- |
| Nalbuphine HCl | 60.0 |
| Mannitol | 72.0 |
| Hydroxypropylcellulose | 30.0 |
| Locust bean gum | 21.6 |
| Xanthan gum | 14.4 |
| Calcium sulfate dehydrate | 12.0 |
| Magnesium stearate | 1.6 |
| Water for injection or | QS |
| Purified water | |
| Total: | 211.6 |

TABLE 21

(Example 25)
120 mg Extended Release Nalbuphine Tablet

| Ingredient | mg/tablet |
| --- | --- |
| Nalbuphine HCl | 120.0 |
| Mannitol | 144.0 |
| Hydroxypropylcellulose | 60.0 |
| Locust bean gum | 43.2 |
| Xanthan gum | 28.8 |
| Calcium sulfate dehydrate | 24.0 |
| Magnesium stearate | 3.2 |
| Water for injection or | QS |
| Purified water | |
| Total: | 423.2 |

TABLE 22

(Example 26)
180 mg Extended Release Nalbuphine Tablet (release 1

| Ingredient | mg/tablet |
| --- | --- |
| Nalbuphine HCl | 180.0 |
| Mannitol | 216.0 |
| Hydroxypropylcellulose | 90.0 |

TABLE 22-continued (Example 26)
180 mg Extended Release Nalbuphine Tablet (release 1

| Ingredient | mg/tablet |
|---|---|
| Locust bean gum | 64.8 |
| Xanthan gum | 43.2 |
| Fumaric acid | 25.0 |
| Calcium sulfate dehydrate | 36.0 |
| Magnesium stearate | 5.0 |
| Water for injection or Purified water | QS |
| Total: | 660.0 |

TABLE 23

(Example 27) 180 mg Extended Release Nalbuphine Tablet (release 2

| Ingredient | mg/tablet |
|---|---|
| Nalbuphine HCl | 180.0 |
| Mannitol | 162.0 |
| Hydroxypropylcellulose | 60.0 |
| Locust bean gum | 48.6 |
| Xanthan gum | 32.4 |
| Fumaric acid | 25.0 |
| Calcium sulfate dehydrate | 27.0 |
| Magnesium stearate | 4.0 |
| Water for injection or Purified water | QS |
| Total: | 539.0 |

TABLE 24

(Example 28) 15 mg Extended Release Nalbuphine Tablet

| Ingredient | mg/tablet |
|---|---|
| Nalbuphine HCl | 15.0 |
| Mannitol | 117.0 |
| Hydroxypropylcellulose | 35.0 |
| Locust bean gum | 35.1 |
| Xanthan gum | 23.4 |
| Calcium sulfate dehydrate | 19.5 |
| Magnesium stearate | 1.9 |
| Water for injection or Purified water | QS |
| Total: | 246.9 |

Example 29

A Phase II, randomized, double-blind, single-dose, placebo-controlled, multi-center, parallel group study of the safety and efficacy of the nalbuphine bi-layer tablet formulation of Example 19 was conducted. Study subjects were randomized to active agent received either a single 60 mg extended release dose of nalbuphine or a single 120 mg (2×60 mg tablets) dose of nalbuphine. Tables 25A-B provides a summary of the observed pharmacokinetic parameters.

TABLE 25A (60 mg single dose)

| Statistic | Cmax (ng/mL) | Tmax (hr) | AUC (ng · hr/ml) |
|---|---|---|---|
| N | 65 | 65 | 65 |
| Mean | 8.1 | 4.5 | 75.2 |
| SD | 4.9 | 2.2 | 45.2 |
| Minimum | 3.0 | 0.5 | 23.6 |
| Median | 6.6 | 6 | 65.3 |
| Maximum | 22.3 | 12 | 256.6 |
| % CV | 60.4% | 48.5% | 60.1% |
| Geometric mean | 6.9 | 3.9 | 64.8 |

TABLE 25B (120 mg single dose)

| Statistic | Cmax (ng/mL) | Tmax (hr) | AUC (ng · hr/ml) |
|---|---|---|---|
| N | 66 | 66 | 66 |
| Mean | 16.4 | 4.3 | 149.2 |
| SD | 10.6 | 2.7 | 77.0 |
| Minimum | 4.6 | 0.5 | 33.2 |
| Median | 13.2 | 3 | 128.3 |
| Maximum | 77.4 | 12 | 450.2 |
| % CV | 64.9% | 63.8% | 51.6% |
| Geometric mean | 14.1 | 3.4 | 133.1 |

Example 30

A Phase I, randomized single dose, four period cross-over study to evaluate the effect of food on two nalbuphine extended release tablet formulations (bi-layer formulation of Example 19 and extended release formulation of Example 20) administered orally to healthy subjects under fed and fasted conditions was conducted. The total single dose administered to each study subject was 120 mg (2×60 mg tablets). Table 25 provides a summary of the observed pharmacokinetic parameters.

TABLE 26

| Treatment | Statistics | $C_{max}$ (ng/mL) | $T_{max}$ (hr) | $AUC_{(0-last)}$ (ng · hr/mL) | $AUC_{(0-\infty)}$ (ng · hr/mL) |
|---|---|---|---|---|---|
| Formula of Example 20 120 mg Fast | N | 9 | 9 | 9 | 9 |
| | Mean | 14.1 | — | 170 | 183 |
| | SD | 6.23 | — | 59.7 | 62.9 |
| | Min | 4.57 | 1.50 | 56.7 | 61.6 |
| | Median | 15.1 | 6.00 | 179 | 195 |
| | Max | 23.6 | 12.00 | 245 | 256 |
| Formula of Example 20 120 mg Fed | N | 9 | 9 | 9 | 9 |
| | Mean | 22.4 | — | 201 | 211 |
| | SD | 12.7 | — | 67.2 | 68.3 |
| | Min | 8.77 | 3.00 | 70.2 | 73.9 |
| | Median | 21.0 | 6.00 | 219 | 227 |
| | Max | 48.6 | 10.00 | 295 | 307 |
| Formula of Example 19 120 mg Fast | N | 9 | 9 | 9 | 9 |
| | Mean | 18.5 | — | 160 | 170 |
| | SD | 7.40 | — | 55.6 | 54.7 |
| | Min | 6.33 | 1.00 | 81.5 | 87.7 |
| | Median | 18.6 | 2.00 | 178 | 186 |
| | Max | 28.7 | 6.00 | 239 | 250 |
| Formula of Example 19 120 mg Fed | N | 9 | 9 | 9 | 9 |
| | Mean | 28.0 | — | 204 | 214 |
| | SD | 16.6 | — | 68.6 | 71.0 |
| | Min | 11.0 | 2.00 | 98.2 | 111 |
| | Median | 24.0 | 6.00 | 227 | 237 |
| | Max | 63.7 | 6.00 | 279 | 295 |

Example 31

A Phase I, randomized, single dose, four period, cross-over study to evaluate the intra-subject variability of two nalbuphine extended release formulations (bi-layer formulation of Example 19 [ERF-2] and extended release formulation of Example 20 [ERF-1]) administered orally to healthy subjects under fasted conditions was conducted. The total single dose administered to each study subject was 120 mg (2×60 mg tablets). Table 27 provides a summary of the observed pharmacokinetic parameters.

TABLE 27

| Treatment | Statistics | $C_{max}$ (ng/mL) | $T_{max}$ (hr) | $AUC_{(0\text{-}last)}$ (ng·hr/mL) | $AUC_{(0\text{-}\infty)}$ (ng·hr/mL) |
|---|---|---|---|---|---|
| ERF-1 (A1) | N | 7 | 7 | 7 | 7 |
| | Mean | 11.3 | — | 139 | 162 |
| | SD | 7.17 | — | 75.0 | 78.8 |
| | Minimum | 3.08 | 2.00 | 39.0 | 47.0 |
| | Median | 12.1 | 6.00 | 157 | 173 |
| | Maximum | 20.5 | 12.00 | 257 | 279 |
| ERF-1 (A2) | N | 7 | 7 | 7 | 6 |
| | Mean | 13.4 | — | 152 | 167 |
| | SD | 8.81 | — | 73.5 | 80.9 |
| | Minimum | 3.70 | 1.50 | 44.7 | 57.3 |
| | Median | 12.3 | 6.00 | 128 | 156 |
| | Maximum | 30.2 | 8.00 | 252 | 263 |
| ERF-2 (C1) | N | 7 | 7 | 7 | 6 |
| | Mean | 14.2 | — | 148 | 170 |
| | SD | 8.87 | — | 78.3 | 78.2 |
| | Minimum | 4.41 | 1.50 | 39.7 | 51.5 |
| | Median | 8.57 | 6.00 | 123 | 176 |
| | Maximum | 26.6 | 8.00 | 259 | 265 |
| ERF-2 (C2) | N | 7 | 7 | 7 | 6 |
| | Mean | 12.5 | — | 137 | 155 |
| | SD | 8.02 | — | 77.5 | 78.9 |
| | Minimum | 4.88 | 1.00 | 44.6 | 49.8 |
| | Median | 9.17 | 2.00 | 142 | 161 |
| | Maximum | 26.3 | 10.00 | 270 | 277 |

Example 32

A phase I, randomized, single-blind, placebo-controlled, multiple ascending dose tolerance trial of nalbuphine extended release tablets (of Example 21) in healthy adult subjects in the fasted state. Table 28 and 29 provides a summary of the observed pharmacokinetic parameters.

TABLE 28

Single Dose Administration Pharmacokinetic Data

| Parameter | Statistics | 60 mg Period 1 | 120 mg Period 2 | 180 mg Period 3 | 180 mg Period 4 |
|---|---|---|---|---|---|
| Cmax | N | 3 | 5 | 3 | 5 |
| (ng/mL) | Mean | 7.920 | 15.574 | 27.800 | 23.420 |
| | SD | 1.4722 | 8.4070 | 9.9000 | 10.6302 |
| | Min | 7.360 | 14.900 | 27.800 | 21.600 |
| | Median | 6.81 | 5.47 | 17.90 | 10.30 |
| | Max | 9.59 | 27.80 | 37.70 | 39.80 |
| Tmax (hr) | N | 3 | 5 | 3 | 5 |
| | Mean | 5.67 | 3.60 | 5.67 | 3.00 |
| | SD | 1.155 | 2.074 | 0.577 | 2.000 |
| | Min | 5.00 | 4.00 | 6.00 | 3.00 |
| | Median | 5.0 | 1.0 | 5.0 | 1.0 |
| | Max | 7.0 | 6.0 | 6.0 | 5.0 |

TABLE 29

Multiple Doses Pharmacokinetic Data

| Treatment | Statistics | 60 mg Period 1 | 120 mg Period 2 | 180 mg Period 3 | 180 mg Period 4 |
|---|---|---|---|---|---|
| Cmax, ss | N | 3 | 5 | 3 | 5 |
| (ng/mL) | Mean | 12.10 | 18.76 | 32.17 | 29.58 |
| | SD | 1.217 | 1.806 | 8.810 | 11.107 |
| | Median | 11.50 | 19.00 | 29.10 | 27.40 |
| | Min | 11.3 | 15.9 | 25.3 | 18.4 |
| | Max | 13.5 | 20.6 | 42.1 | 46.7 |
| Tmax, ss (hr) | N | 3 | 5 | 3 | 5 |
| | Mean | 5.00 | 3.40 | 4.33 | 5.60 |
| | SD | 1.000 | 2.074 | 3.215 | 0.894 |
| | Median | 5.00 | 3.00 | 3.00 | 5.00 |
| | Min | 4.0 | 1.0 | 2.0 | 5.0 |
| | Max | 6.0 | 6.0 | 8.0 | 7.0 |
| Cmin, ss | N | 3 | 5 | 3 | 5 |
| (ng/mL) | Mean | 3.263 | 5.974 | 12.067 | 7.232 |
| | SD | 0.7966 | 0.9232 | 1.6653 | 2.1101 |
| | Median | 3.450 | 6.300 | 12.600 | 7.440 |
| | Min | 2.39 | 4.85 | 10.20 | 4.84 |
| | Max | 3.95 | 7.08 | 13.40 | 10.20 |

Example 33

A phase I, randomized, single dose, five-period cross-over study in healthy subjects to evaluate the intra-subject variability of a nalbuphine extended release tablet formulation (of Example 22). Table 30 provides a summary of the observed pharmacokinetic parameters.

TABLE 30

| Parameter | Statistics | Treatment A1 | Treatment A2 | 120 mg (Fast) Treatment A | 120 mg (Fed) Treatment B | Oral Solution Treatment C | Oral Solution Treatment D |
|---|---|---|---|---|---|---|---|
| Cmax | N | 12 | 12 | 12 | 12 | 12 | 12 |
| (ng/mL) | Mean | 12.498 | 12.903 | 12.700 | 18.549 | 18.503 | 16.863 |
| | SD | 7.1308 | 5.4062 | 5.7697 | 10.6560 | 7.8579 | 6.7619 |
| | Median | 12.100 | 13.300 | 11.370 | 15.950 | 17.100 | 14.950 |
| | Min | 4.03 | 3.83 | 3.93 | 5.79 | 8.53 | 8.62 |
| | Max | 32.30 | 20.30 | 26.30 | 41.90 | 36.30 | 31.40 |
| Tmax (hr) | N | 12 | 12 | 12 | 12 | 12 | 12 |
| | Mean | 5.250 | 5.167 | 5.208 | 4.625 | 0.750 | 2.817 |
| | SD | 3.4411 | 2.6572 | 2.3400 | 2.0352 | 0.3371 | 0.8055 |
| | Median | 3.500 | 6.000 | 5.750 | 6.000 | 0.500 | 1.900 |
| | Min | 2.00 | 1.00 | 2.00 | 1.50 | 0.50 | 1.00 |
| | Max | 12.00 | 8.00 | 10.00 | 6.00 | 1.50 | 4.00 |

TABLE 30-continued

| Parameter | Statistics | Treatment A1 | Treatment A2 | 120 mg (Fast) Treatment A | 120 mg (Fed) Treatment B | Oral Solution Treatment C | Oral Solution Treatment D |
|---|---|---|---|---|---|---|---|
| AUC (0-last) (ng · hr/mL) | N | 12 | 12 | 12 | 12 | 12 | 12 |
| | Mean | 159.450 | 154.391 | 156.921 | 169.723 | 83.793 | 103.154 |
| | SD | 60.2859 | 59.9296 | 54.7635 | 70.0775 | 24.1551 | 27.2275 |
| | Median | 155.720 | 151.944 | 158.828 | 168.859 | 84.097 | 101.217 |
| | Min | 56.97 | 54.32 | 55.65 | 56.76 | 51.24 | 63.89 |
| | Max | 260.41 | 274.17 | 267.29 | 282.63 | 143.74 | 147.43 |
| AUC (0-∞) (ng · hr/mL) | N | 8 | 8 | 8 | 8 | 8 | 8 |
| | Mean | 160.790 | 161.532 | 161.161 | 170.590 | 85.926 | 103.053 |
| | SD | 61.1655 | 54.6973 | 51.8638 | 69.3711 | 13.6623 | 29.5312 |
| | Median | 152.985 | 166.487 | 167.257 | 162.708 | 90.056 | 96.558 |
| | Min | 64.80 | 63.01 | 63.91 | 66.16 | 63.66 | 70.24 |
| | Max | 238.44 | 258.27 | 213.18 | 272.16 | 104.20 | 151.97 |

Example 34

A phase I, open-label, single dose, five-period cross-over study to determine the dose proportionality of 30, 60 120 and 180 mg nalbuphine extended release tablet formulations (of Examples 24-28). Table 31A-E provides a summary of the observed pharmacokinetic parameters for the 60 mg, 120 mg and 180 mg formulations of Examples 25, 26, 27 and 28, respectively.

TABLE 31A

| Treatment Description | Parameter | $T_{max}$(hr) N = 22 | $C_{max}$ (ng/mL) N = 22 | $AUC_{last}$ (hr · ng/mL) N = 22 | $AUC_{INF}$ (hr · ng/mL) N = 19 |
|---|---|---|---|---|---|
| 30 mg nalbuphine HCl ER tablet | Mean | 4.159 | 4.130 | 42.988 | 54.993 |
| | SD | 1.996 | 2.338 | 20.135 | 20.681 |
| | Min | 1.50 | 1.95 | 21.26 | 27.35 |
| | Median | 3.00 | 3.82 | 39.99 | 53.13 |
| | Max | 8.00 | 12.70 | 110.41 | 117.08 |

TABLE 31B

| Treatment Description | Parameter | $T_{max}$(hr) N = 24 | $C_{max}$ (ng/mL) N = 24 | $AUC_{last}$ (hr · ng/mL) N = 24 | $AUC_{INF}$ (hr · ng/mL) N = 23 |
|---|---|---|---|---|---|
| 60 mg nalbuphine HCl ER tablet | Mean | 7.417 | 7.750 | 94.496 | 108.798 |
| | SD | 2.962 | 6.034 | 40.001 | 38.737 |
| | Min | 3.00 | 2.84 | 37.56 | 50.73 |
| | Median | 6.00 | 6.07 | 89.31 | 103.12 |
| | Max | 12.00 | 29.90 | 186.60 | 196.41 |

TABLE 31C

| Treatment Description | Parameter | $T_{max}$(hr) N = 19 | $C_{max}$ (ng/mL) N = 19 | $AUC_{last}$ (hr · ng/mL) N = 19 | $AUC_{INF}$ (hr · ng/mL) N = 18 |
|---|---|---|---|---|---|
| 120 mg nalbuphine HCl ER tablet | Mean | 6.316 | 13.265 | 192.434 | 208.312 |
| | SD | 2.709 | 6.458 | 82.867 | 90.778 |
| | Min | 1.00 | 6.54 | 81.41 | 105.82 |
| | Median | 6.00 | 12.80 | 197.01 | 205.96 |
| | Max | 12.00 | 34.80 | 463.17 | 503.93 |

TABLE 31D

| Treatment Description | Parameter | $T_{max}$(hr) N = 15 | $C_{max}$ (ng/mL) N = 15 | $AUC_{last}$ (hr · ng/mL) N = 15 | $AUC_{INF}$ (hr · ng/mL) N = 15 |
|---|---|---|---|---|---|
| 180 mg nalbuphine HCl ER tablet (release 1) | Mean | 7.600 | 21.559 | 297.460 | 327.842 |
| | SD | 3.043 | 23.526 | 154.701 | 164.674 |
| | Min | 2.00 | 5.89 | 138.35 | 148.67 |
| | Median | 6.00 | 16.30 | 274.64 | 288.86 |
| | Max | 12.00 | 102.00 | 722.79 | 760.86 |

TABLE 31E

| Treatment Description | Parameter | $T_{max}$(hr) N = 19 | $C_{max}$ (ng/mL) N = 19 | $AUC_{last}$ (hr · ng/mL) N = 19 | $AUC_{INF}$ (hr · ng/mL) N = 18 |
|---|---|---|---|---|---|
| 180 mg nalbuphine HCl ER tablet (release 2) | Mean | 8.000 | 19.182 | 318.759 | 339.507 |
| | SD | 4.604 | 11.007 | 167.371 | 117.176 |
| | Min | 1.00 | 8.25 | 151.52 | 156.52 |
| | Median | 6.00 | 17.60 | 280.56 | 291.71 |
| | Max | 16.00 | 56.40 | 877.38 | 909.86 |

Example 35

The tablet of Example 28 was tested for % release according to USP Procedure Drug Release General Chapter <711> Dissolution, using apparatus USP Type 111/250 mL. The test was performed at pH 6.8 and pH 6.8, 37° C./15 dpm (dips per minute) in 100 mM ammonium phosphate buffer. The results are shown in Table 32.

TABLE 32

| Dissolution Time (hours) | pH 4.5 (% dissolution) | pH 6.8 (% dissolution) |
|---|---|---|
| 0 | 0 | 0 |
| 1 | 30 | 41 |
| 3 | 58 | 64 |
| 4 | 68 | 71 |
| 6 | 81 | 84 |
| 8 | 89 | 92 |
| 12 | 97 | 101 |

Example 36

The tablet of Example 23 was coated with a non-functional coat and was tested in a clinical trial in renally impaired patients on hemodialysis and healthy subjects with normal kidney function and pK data were collected following multiple ascending increasing doses.

TABLE 33

Nalbuphine HCl ER Tablets, 30 mg Composition

| Component | Tablet (mg/tablet) |
|---|---|
| Nalbuphine HCl | 30.0 |
| Mannitol | 108.0 |
| Hydroxypropylcellulose | 35.0 |
| Locust bean gum | 32.4 |
| Xanthan gum | 21.6 |
| Calcium sulfate dihydrate | 18.0 |
| Magnesium stearate[1] | 1.9 |
| Opadry II White | 7.4 |
| Sterile water for irrigation[2] | QS |
| | 254.3 |

TABLE 34

Summary of PK Parameters following multiple ascending oral doses of nalbuphine HCl ER tablets in hemodialysis (HD) patients and healthy subjects (TREVI Clinical Study TR01)

| Parameter | Descriptive Statistics | HD Patients | | | | | | Healthy Subjects | | | | |
|---|---|---|---|---|---|---|---|---|---|---|---|---|
| | | 30 mg QD (Day 1) | 30 mg BID (Day 4) | 60 mg BID (Day 6) | 120 mg BID (Day 9) | 180 mg BID (Day 13) | 240 mg BID (Day 15) | 30 mg QD (Day 1) | 30 mg BID (Day 4) | 60 mg BID (Day 6) | 120 mg BID (Day 9) | 180 mg BID (Day 13) |
| AUCinf (h*ng/mL) | n | 4 | . | . | . | 4 | 2 | 7 | . | . | . | 8 |
| | Mean | 142.5 | . | . | . | 2635.38 | 1524.3 | 49.53 | . | . | . | 588.4 |
| | SD | 33.28 | . | . | . | 2038.01 | 121.38 | 30.04 | . | . | . | 214.08 |
| | CV % | 23.4 | . | . | . | 77.3 | 8 | 60.7 | . | . | . | 36.4 |
| | Minimum | 107.51 | . | . | . | 299.8 | 1438.48 | 17.01 | . | . | . | 211.06 |
| | Maximum | 177 | . | . | . | 4543.71 | 1610.13 | 84.27 | . | . | . | 886.68 |
| AUCtau (h*ng/mL) | n | 15 | 14 | 10 | 10 | 9 | 3 | 9 | 9 | 9 | 9 | 8 |
| | Mean | 43.2 | 117.97 | 221.68 | 621.79 | 760.87 | 769.99 | 31.53 | 50.88 | 106.11 | 240.37 | 351.15 |
| | SD | 24.97 | 76.41 | 145.04 | 415.94 | 538.28 | 509.88 | 16.93 | 27.54 | 50.49 | 93.68 | 118.21 |
| | CV % | 57.8 | 64.8 | 65.4 | 66.9 | 70.7 | 66.2 | 53.7 | 54.1 | 47.6 | 39 | 33.7 |
| | Minimum | 2.58 | 15.08 | 24.1 | 78.75 | 130.53 | 420.03 | 13.37 | 18.51 | 34.42 | 122.53 | 139.51 |
| | Maximum | 95.79 | 274.33 | 509.9 | 1233.92 | 1689.9 | 1355 | 57.06 | 96.94 | 192.34 | 369.78 | 523.25 |
| Cmax (ng/mL) | n | 15 | 14 | 10 | 10 | 9 | 4 | 9 | 9 | 9 | 9 | 8 |
| | Mean | 6.28 | 13.44 | 24.78 | 70.33 | 82.78 | 61.42 | 5.2 | 6.45 | 13.46 | 28 | 44.21 |
| | SD | 3.36 | 8.31 | 17.38 | 48.81 | 55.81 | 56.9 | 2.78 | 3.58 | 6.43 | 11.49 | 14.54 |
| | CV % | 53.5 | 61.8 | 70.1 | 69.4 | 67.4 | 92.6 | 53.5 | 55.5 | 47.8 | 41 | 32.9 |
| | Minimum | 0.65 | 1.65 | 2.63 | 9 | 14.7 | 4.28 | 2.56 | 2.53 | 4.9 | 17.1 | 25.2 |
| | Maximum | 12.5 | 29.9 | 62.5 | 155 | 188 | 140 | 9.3 | 12.9 | 24.1 | 46.9 | 68.6 |
| T½ (h) | n | 4 | . | . | . | 4 | 2 | 7 | . | . | . | 8 |
| | Mean | 10.49 | . | . | . | 14.23 | 20.32 | 6.81 | . | . | . | 8.58 |
| | SD | 2.22 | . | . | . | 3.24 | 0.41 | 2.79 | . | . | . | 2.05 |
| | CV % | 21.1 | . | . | . | 22.7 | 2 | 41 | . | . | . | 23.9 |
| | Minimum | 8.1 | . | . | . | 10.02 | 20.03 | 3.92 | . | . | . | 4.84 |
| | Maximum | 13.46 | . | . | . | 17.77 | 20.61 | 11.64 | . | . | . | 11.88 |
| Tmax (h) | n | 15 | 14 | 10 | 10 | 9 | 4 | 9 | 9 | 9 | 9 | 8 |
| | Minimum | 1 | 0 | 0 | 3 | 2 | 0 | 2 | 2 | 2 | 3 | 2 |
| | Median | 5 | 4 | 5 | 6 | 5 | 6.03 | 3 | 2 | 3 | 5 | 4 |
| | Maximum | 18 | 9 | 9 | 9 | 7.1 | 12 | 5 | 6 | 6 | 9 | 6 |

TABLE 35

Trough (or Cmin) nalbuphine concentrations (ng/mL) as a function of dose and dosing day in hemodialysis patients and healthy subjects (Clinical Study TR01)

| Timepoint | Descriptive Statistics | HD Subjects | | | | | | | | Healthy Subjects | | | |
|---|---|---|---|---|---|---|---|---|---|---|---|---|---|
| | | 30 mg (Day 2) | 30 mg (Day 3) | 60 mg (Day 5) | 60 mg (Day 6) | 120 mg (Day 8) | 120 mg (Day 10) | 180 mg (Day 11) | 240 mg (Day 13) | 30 mg (Day 2) | 60 mg (Day 5) | 120 mg (Day 8) | 180 mg (Day 11) |
| PRE AM DOSE | n | 15 | 4 | 14 | 4 | 14 | 4 | 13 | 4 | 9 | 9 | 9 | 8 |
| | Mean | 2.06 | 6 | 12.6 | 11.46 | 22.2 | 35.75 | 38.94 | 36.03 | 0.43 | 5.29 | 11.3 | 20.4 |
| | SD | 1.34 | 4.3 | 8.75 | 7.13 | 14.47 | 26.81 | 28.12 | 20.1 | 0.54 | 2.96 | 4.71 | 11.71 |
| | CV % | 65 | 71.6 | 69.4 | 62.3 | 65.2 | 75 | 72.2 | 55.8 | 125.4 | 56 | 41.7 | 57.4 |
| | Minimum | 0 | 2.63 | 2.06 | 7.34 | 3.12 | 16.1 | 5.87 | 23.4 | 0 | 1.6 | 3.89 | 6.51 |
| | Maximum | 4.86 | 12.1 | 31.2 | 22.1 | 43 | 75.3 | 94.7 | 65.9 | 1.31 | 9.2 | 17.2 | 42.6 |
| PRE PM DOSE | n | 15 | 4 | 14 | 4 | 14 | 4 | 12 | 4 | 9 | 9 | 9 | 8 |
| | Mean | 5.25 | 5.57 | 11.86 | 10.92 | 26.73 | 21.63 | 50.82 | 41.85 | 2.14 | 5.89 | 11.59 | 18.18 |
| | SD | 2.78 | 2.2 | 8.15 | 5.88 | 17.03 | 6.6 | 37.16 | 22.08 | 1.06 | 2.56 | 4.97 | 6.05 |
| | CV % | 53 | 39.5 | 68.7 | 53.8 | 63.7 | 30.5 | 73.1 | 52.8 | 49.6 | 43.6 | 42.9 | 33.3 |
| | Minimum | 0.752 | 3.48 | 1.03 | 6.18 | 2.2 | 16.1 | 5.31 | 28.2 | 0.868 | 2.07 | 4.67 | 7.37 |
| | Maximum | 10.1 | 8.63 | 25.4 | 19.5 | 61.2 | 29.4 | 109 | 74.5 | 3.65 | 9.35 | 18.7 | 27.3 |

The embodiments described herein and illustrated by the foregoing examples should be understood to be illustrative of the present invention, and should not be construed as limiting. On the contrary, the present disclosure embraces alternatives and equivalents thereof, as embodied by the appended claims. Each reference disclosed herein is incorporated by reference herein in its entirety.

What is claimed is:

1. A method of treating prurigo nodularis comprising orally administering an effective amount of an anti-pruritus agent to a human subject in need of such treatment, wherein the anti-pruritus agent is nalbuphine or a pharmaceutically acceptable salt or ester thereof.

2. The method of claim 1, wherein the administration provides in the subject a mean $AUC_{tau}$ from about 40 ng·hr/mL to about 800 ng·hr/mL.

3. The method of claim 1, wherein the administration provides in the subject a mean $AUC_{tau}$ from about 40 ng·hr/mL to about 200 ng·hr/mL.

4. The method of claim 1, wherein the administration provides in the subject a mean $AUC_{tau}$ from about 180 ng·hr/mL to about 320 ng·hr/mL.

5. The method of claim 1, wherein the administration provides in the subject a mean $AUC_{tau}$ from about 100 ng·hr/mL to about 400 ng·hr/mL.

6. The method of claim 1, wherein the administration provides in the subject a mean $AUC_{tau}$ from about 200 ng·hr/mL to about 500 ng·hr/mL.

7. The method of claim 1, wherein the administration provides in the subject a mean $AUC_{tau}$ from about 300 ng·hr/mL to about 600 ng·hr/mL.

8. The method of claim 1, wherein the administration provides in the subject a mean $AUC_{tau}$ from about 400 ng·hr/mL to about 700 ng·hr/mL.

9. The method of claim 1, wherein the administration provides in the subject a mean $AUC_{tau}$ from about 500 ng·hr/mL to about 800 ng·hr/mL.

10. The method of claim 1, wherein the administration provides in the subject a mean $AUC_{tau}$ from about 100 ng·hr/mL to about 300 ng·hr/mL.

11. The method of claim 1, wherein the administration provides in the subject a mean $AUC_{tau}$ from about 200 ng·hr/mL to about 400 ng·hr/mL.

12. The method of claim 1, wherein the administration provides in the subject a mean $AUC_{tau}$ from about 300 ng·hr/mL to about 500 ng·hr/mL.

13. The method of claim 1, wherein the administration provides in the subject a mean $AUC_{tau}$ from about 400 ng·hr/mL to about 600 ng·hr/mL.

14. The method of claim 1, wherein the administration provides in the subject a mean $AUC_{tau}$ from about 500 ng·hr/mL to about 700 ng·hr/mL.

15. The method of claim 1, wherein the administration provides in the subject a mean $AUC_{tau}$ from about 600 ng·hr/mL to about 800 ng·hr/mL.

16. The method of claim 1, wherein the anti-pruritus agent is an extended release oral dosage form and the administration provides in the subject a mean $C_{max}$ of from about 1 ng/mL to about 90 ng/mL, from about 5 ng/mL to about 85 ng/mL, from about 5 ng/ml to about 45 ng/ml, from about 25 ng/mL to about 72 ng/mL, or from about 13 ng/mL to about 28 ng/mL.

17. The method of claim 1, wherein the anti-pruritus agent is an extended release oral dosage form and the administration provides in the subject a mean $C_{max}$ of from about 5 ng/ml to about 45 ng/ml.

18. The method of claim 1, wherein the anti-pruritus agent is administered about 180 mg twice daily.

19. The method of claim 1, wherein the total daily dose of the anti-pruritus agent is about 360 mg.

20. The method of claim 1, wherein the anti-pruritus agent is in an extended release oral dosage form.

21. The method of claim 1, wherein the anti-pruritus agent is administered at an initial oral dose of from about 15 mg to about 30 mg twice a day and then titrated to an effective dose.

22. The method of claim 1, wherein the anti-pruritus agent is administered at an initial dose of from about 15 mg to about 30 mg once a day and then titrated to an effective dose.

23. The method of claim 1, wherein the anti-pruritus agent is administered in a formulation comprising nalbuphine hydrochloride, mannitol, hydroxypropyl cellulose, locust bean gum, xanthan gum, calcium sulfate dihydrate and magnesium stearate.

* * * * *